US011685711B2

(12) United States Patent
De La Cruz et al.

(10) Patent No.: US 11,685,711 B2
(45) Date of Patent: Jun. 27, 2023

(54) CARBON MONOXIDE-RELEASING MOLECULES TRIGGERED BY PHYSIOLOGICAL STIMULI

(71) Applicant: Georgia State University Research Foundation, Inc., Atlanta, GA (US)

(72) Inventors: Ladie Kimberly c. De La Cruz, Atlanta, GA (US); Xingyue Ji, Atlanta, GA (US); Zhixiang Pan, Atlanta, GA (US); Binghe Wang, Atlanta, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 297 days.

(21) Appl. No.: 16/637,737

(22) PCT Filed: Aug. 9, 2018

(86) PCT No.: PCT/US2018/046080
§ 371 (c)(1),
(2) Date: Feb. 7, 2020

(87) PCT Pub. No.: WO2019/032879
PCT Pub. Date: Feb. 14, 2019

(65) Prior Publication Data
US 2020/0283382 A1 Sep. 10, 2020

Related U.S. Application Data

(60) Provisional application No. 62/543,304, filed on Aug. 9, 2017.

(51) Int. Cl.
| | | |
|---|---|---|
| C07C 323/65 | (2006.01) | |
| C07C 49/757 | (2006.01) | |
| C07C 62/38 | (2006.01) | |
| C07C 323/22 | (2006.01) | |
| C07D 335/04 | (2006.01) | |

(52) U.S. Cl.
CPC .......... *C07C 323/65* (2013.01); *C07C 49/757* (2013.01); *C07C 62/38* (2013.01); *C07C 323/22* (2013.01); *C07D 335/04* (2013.01); *C07C 2602/42* (2017.05)

(58) Field of Classification Search
CPC ..... C07C 323/65; C07C 49/757; C07C 62/38; C07C 323/22; C07C 2602/42; C07D 335/04
See application file for complete search history.

(56) References Cited

U.S. PATENT DOCUMENTS

| | | | |
|---|---|---|---|
| 10,300,069 | B2 | 5/2019 | Wang et al. |
| 10,751,344 | B2 | 8/2020 | Wang et al. |
| 2017/0128456 | A1 | 5/2017 | Wang et al. |
| 2020/0115360 | A1 | 4/2020 | Wang et al. |
| 2021/0221835 | A1 | 7/2021 | Wang et al. |

FOREIGN PATENT DOCUMENTS

| | | | | |
|---|---|---|---|---|
| EP | 2319518 A1 | 5/2011 | | |
| WO | 2017095237 A1 | 6/2017 | | |
| WO | WO-2017095237 A1 | * 6/2017 | ............. | A61P 11/00 |
| WO | 2018/093924 A1 | 5/2018 | | |
| WO | 2018/231841 A1 | 12/2018 | | |

OTHER PUBLICATIONS

Ji et al. Chem. Commun. 2017, 53, 9628-9631 (Year: 2017).*
Pan et al. Org Lett. 2018, 20, 8-11 (Year: 2017).*
Paquette et al. J. Am. Chem. Soc. 1978, 100, 1597-1599 (Year: 1978).*
Sasaki et al. J. Org. Chem. 1976, 41, 1105-1112 (Year: 1976).*
Botov, et al. "Synthesis and Performance of Acyloxy-diene-Fe(CO)₃ Complexes with Variable Chain Lengths as Enzyme-Triggered Carbon Monoxide-Releasing Molecules." Organometallics. 2013; 32:3587-3594.
Heinemann, et al. "Carbon monoxide-physiology, detection and controlled release." Chem Commun. 2014;50:3644-3660.
Moiierlini et al., "CORM-A1: a new pharmacologically active carbon monoxide releasing molecule." FASEB J. Feb. 2005, vol. 19, 284-286.
Peng, et al. "Visible-light activatable organic CO-releasing molecules (photoCORMs) that simultaneously generate fluorophores." Org Biomol Chem. 2013;11:6671-6674.
Romanski, et al. "Iron Dienylphosphate Tricarbonyl Complexes as Water-SolubleEnzyme-Triggered CO-Releasing Molecules (ET-CORMs)." Organometallics. 2012; 31:5800-5809.
Schatzschneider. "Novel lead structures and activation mechanisms for CO-releasing molecules (CORM)." British Journal of Pharmacology. 2015; 172:1638-1650.
Stamellou, et al. "Different design of enzyme-triggered CO-releasing molecules (ET-CORMs) reveals quantitative differences in biological activities in terms of toxicity and inflammation." Redox Biology. 2014; 2: 739-748.
Wang, et al. "3,6-substituted-1,2,4,5-tetrazines: tuning reaction rates for staged labeling applications." Org Biomol Chem. 2014;12: 3950-3955.
Wang et al., "A Click-and-Release Approach to CO Prodrugs", Chemical Communications, vol. 50, No. 100, Oct. 31, 2014, pp. 15890-15893.
PubChem , "1,2,3,4,5-Pentaphenylbicyclo[2.2.1]Hept-2-En-7-One", PubChem, CID 3089169, Available online at https://pubchem.ncbi.nlm.nih.gov/compound/3089169, Aug. 9, 2005, pp. 1-11, p. 3, formula.

(Continued)

*Primary Examiner* — Matthew P Coughlin
(74) *Attorney, Agent, or Firm* — Kilpatrick Townsend & Stockton LLP

(57) ABSTRACT

The present invention generally relates to carbon monoxide releasing compounds and compositions, and their use as carbon monoxide prodrugs.

18 Claims, 10 Drawing Sheets

(56) References Cited

OTHER PUBLICATIONS

International Bureau; International Search Report and Written Opinion; dated Dec. 3, 2018, received in PCT/US2018/046080; filed Aug. 9, 2018; 13 pages.
International Bureau, Invitation to Pay additional Fees with Partial Search Report; dated Sep. 24, 2018; received in International, application No. PCT/US2018/046080; filed Aug. 9, 2018; 2 pages.
International Bureau; International Preliminary Report on Patentability; dated Feb. 20, 2020, received in International Application No. PCT/US2018/046080; filed Aug. 9, 2018; 9 pages.

* cited by examiner

CARBON MONOXIDE-RELEASING MOLECULES TRIGGERED BY PHYSIOLOGICAL STIMULI

CROSS-REFERENCES TO RELATED APPLICATIONS

The present application is a 35 U.S.C. 371 national stage application of International Pat. Appl. No. PCT/US2018/046080, filed on Aug. 9, 2018, which claims priority to U.S. Provisional Pat. Appl. No. 62/543,304, filed on Aug. 9, 2017, which applications are incorporated herein by reference in their entirety.

STATEMENT AS TO RIGHTS TO INVENTIONS MADE UNDER FEDERALLY SPONSORED RESEARCH AND DEVELOPMENT

This invention was made with government support under Grant No. CA 180519 awarded by the National Institutes of Health. The government has certain rights in the invention.

BACKGROUND OF THE INVENTION

Carbon monoxide, generated by heme oxygenase-mediated heme degradation, is an endogenous signaling molecule with strong cytoprotective and anti-inflammatory effects. One widely studied application of CO is in treating ulcerative colitis (UC), which is a progressive, chronic and relapsing inflammatory disorder of digestive tract, leading to various complications including abscesses, stenosis, extraintestinal manifestations and colitis-associated neoplasia and cancer. Additional evidence of CO's effect comes from population-based studies that saw a lower level of incidents of UC in smokers than in non-smokers, with the belief that CO is the connection. In addition, the dysbiosis of gut microbiota is believed to contribute to the development of UC, and CO is reported to play vital roles in maintaining the gut microbiota hemostasis, indicating significant benefits of using CO against UC. Therefore, there have been remarkable efforts in delivering CO for the treatment of experimental UC. For example, much effect has been devoted to the search for CO-releasing molecules (CO-RMs) with either spontaneous release upon dissolution or controllable release in response to various stimulus, including photo-, enzyme-, and oxidation-sensitive and encapsulated CO-RMs. The present inventors have recently developed a successful series of metal-free CO prodrugs by using inter-, or intra-molecular Diels-Alder (DA) reactions to trigger CO release. Among all the successes, pH-sensitive CO release is considered as a very important method for achieving local delivery of CO, e.g., local gastric delivery. Among CO's therapeutic indications, cancer, bacterial infection and inflammation are the most widely investigated, and CO has been firmly established as a promising therapeutic agent against these diseases. Notably, these diseases are all associated with elevated levels of reactive oxygen species (ROS). Therefore, it is highly desirable to devise CO prodrugs with an ROS trigger for targeted delivery to these disease sites. However, ROS-sensitive CO delivery is a severely under-explored area, especially in ROS-triggered metal-free CO release. Therefore, there is a need for compounds that can controllably release CO in vivo and in vitro with little or no toxicity in response to physiological stimuli such as reactive oxygen species and/or changes in pH, among others. The present invention addresses this and other needs.

BRIEF SUMMARY OF THE INVENTION

In one aspect, the invention provides compounds comprising a cyclopentenone moiety and a reactive moiety, wherein exposure of compound to physiological conditions results in elimination of the reactive moiety and release of carbon monoxide.

In some embodiments, the invention provides compounds according to Formula I:

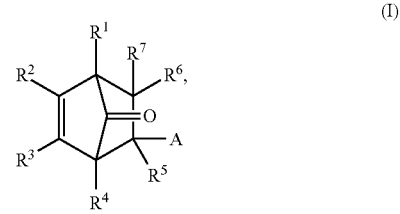

(I)

and pharmaceutically acceptable salts thereof, wherein:
  $R^1$, $R^2$, $R^3$, and $R^4$ are independently selected from the group consisting of hydrogen (i.e., "H"), $C_{1-8}$ alkyl, $C_{3-8}$ cycloalkyl, $C_{6-10}$ aryl, 3- to 8-membered heterocyclyl, 5- to 12-membered heteroaryl, and —$C(O)OR^8$;
  $R^2$ and $R^3$ are optionally taken together to form a fused bicyclic moiety or a fused tricyclic moiety;
  $R^5$ is selected from the group consisting of H, $C_{1-8}$ alkyl, —CN, —$C(O)OR^9$, —$C(O)R^{10}$, —$C(O)N(R^{11})_2$, and a targeting moiety;
  $R^6$ and $R^7$ are independently selected from the group consisting of H, $C_{1-8}$ alkyl, —CN, —$C(O)OR^9$, —$C(O)R^{10}$, —$C(O)N(R^{11})_2$, —$S(O)R^{12}$, and $S(O)_2R^{12}$;
  A is the reactive moiety, which is selected from the group consisting of —$SeR^{13}$, —$OS(O)_2R^{14}$, —$SR^{14}$, —$S(O)R^{14}$, —$S(O)_2R^{14}$, —$OR^{15}$, —$OP(O)(OR^{15})_2$, —$OC(O)R^{16}$, —$OC(O)N(R^{17})_2$, —$N^+(R^{17})_3$, and halogen;
  $R^8$ is selected from the group consisting of H and $C_{1-6}$ alkyl;
  each $R^9$, $R^{10}$, $R^{11}$, and $R^{12}$ is independently selected from the group consisting of H, $C_{1-8}$ alkyl, $C_{2-8}$ acyl, $C_{6-10}$ aryl, and a targeting moiety;
  each $R^{13}$, $R^{14}$, $R^{15}$, $R^{16}$, and $R^{17}$ are selected from the group consisting of $C_{1-8}$ alkyl, $C_{3-8}$ cycloalkyl, $C_{6-10}$ aryl, and 5- to 12-membered heteroaryl;
  in $R^6$ or $R^7$, one of $R^9$, $R^{10}$, $R^{11}$, and $R^{12}$ is optionally taken together with one of $R^{13}$, $R^{14}$, $R^{15}$, $R^{16}$, and $R^{17}$ to form a monocyclic moiety;
  each of $R^1$-$R^7$ and $R^{13}$-$R^{17}$ is optionally and independently substituted with one or more substituents independently selected from the group consisting of halogen, $C_{1-4}$ alkyl, $C_{1-4}$ haloalkyl, —CN, —$NO_2$, —$OR^a$, —$C(O)R^b$, —$C(O)OR^a$, —$OC(O)R^b$, —$N(R^a)_2$, —$NR^aC(O)R^b$, —$C(O)N(R^a)_2$, —$S(O)R^b$, —$S(O)_2R^b$, —$S(O)_2OR^a$, —$S(O)_2N(R^a)_2$, and —$NR^aS(O)_2R^b$;
  each $R^a$ is independently selected from the group consisting of H, $C_{1-4}$ alkyl, a solubilizing moiety, and a targeting moiety; and
  each $R^b$ is independently selected from the group consisting of $C_{1-4}$ alkyl, a solubilizing moiety, and a targeting moiety.

Pharmaceutical compositions and methods of treating diseases with carbon monoxide prodrugs are also described.

DETAILED DESCRIPTION OF THE INVENTION

I. General

Figure 1:
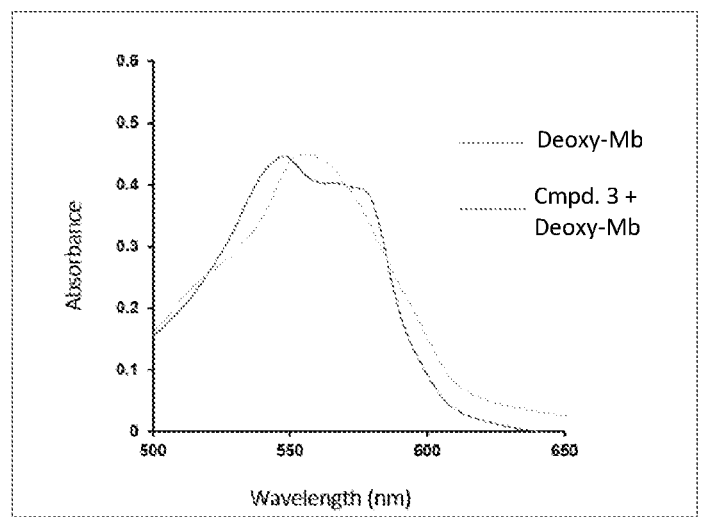
FIG. 1 shows spectroscopic data recorded using a CO-myoglobin assay.

Described herein are molecules that can controllably and selectively release CO in vivo and in vitro with little or no toxicity in response to endogenous biological stimuli, without the need for external stimuli. Methods for treating diseases and conditions using the carbon monoxide releasing compounds (also referred to as "CO prodrugs") are also described. Metal-free, pH-sensitive CO prodrugs are provided. In certain embodiments, the pH-sensitive prodrugs are stable under acidic conditions but release CO at pH values above around 4. The tunable and predictable release rates exhibited by the compounds provides for lower gastrointestinal (GI) delivery. In addition, metal-free, oxidation-sensitive CO prodrugs are provided. The oxidation-sensitive CO prodrugs can selectively deliver CO to cells with elevated ROS level (e.g., cancer cells and inflammatory cells) and can sensitize cancer cells to other therapeutic agents (e.g., doxorubicin). This sensitization can reduce the required dosage of chemotherapeutic drugs, and thereby alleviate chemotherapy-related side effects.

II. Definitions

As used herein, the terms "compound" and "compound of the invention" are used interchangeably and refer to a molecule of the present invention comprising a cyclopentenone moiety and a reactive moiety, wherein the reactive moiety can be eliminated to provide carbon monoxide release.

As used herein, the term "carbon monoxide" refers to $:C\equiv\overset{+}{O}:$ and $:C=\overset{..}{O}:$ as well as other forms of carbon monoxide formed under physiological conditions.

As used herein, the term "cyclopentenone moiety" refers to a moiety of a compound of the invention having the structure

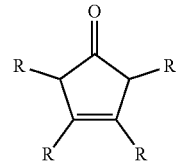

wherein R is H or another substituent as described herein. In some embodiments, R is $R^1$, $R^2$, and $R^3$ as defined below; R groups can also be taken together to form fused polycyclic ring systems (e.g., bicyclo[2.2.1]hept-2-en-7-one and the like).

As used herein, the term "physiological conditions" refers to one or more of physiological temperature, pH, and tonicity. Body temperature is typically from about 33° C. to about 40° C., preferably from about 35° C. to about 38° C., such as about 37° C. Physiological pH is typically from about 6.8 to 8, preferably 6.8 to about 7.5, such as about 7.0. However, the pH may be lower or higher at specific sites and/or due to a particular disease state. For example, the pH of gastric acid ranges from around 1.5 to around 3.5 in the human stomach lumen, and lower pH is often associated with diseased tissue such as tumor tissue.

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to, heptyl, octyl, nonyl, decyl, etc. Alkyl groups can be substituted or unsubstituted. Unless otherwise specified, "substituted alkyl" groups can be substituted with one or more groups selected from halo, hydroxy, amino, alkylamino, amido, acyl, nitro, cyano, and alkoxy.

As used herein, the term "alkoxy," by itself or as part of another substituent, refers to a group having the formula —OR, wherein R is alkyl as described above.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. Unless otherwise specified, "substituted cycloalkyl" groups can be substituted with one or more groups selected from halo, hydroxy, amino, alkylamino, amido, acyl, nitro, cyano, and alkoxy.

As used herein, the term "alkylene" refers to an alkyl group, as defined above, linking at least two other groups (i.e., a divalent alkyl radical). The two moieties linked to the alkylene group can be linked to the same carbon atom or different carbon atoms of the alkylene group.

As used herein, the terms "halo" and "halogen," by themselves or as part of another substituent, refer to a fluorine, chlorine, bromine, or iodine atom.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "aryl," by itself or as part of another substituent, refers to an aromatic ring system having any suitable number of carbon ring atoms and any suitable number of rings. Aryl groups can include any suitable number of carbon ring atoms, such as $C_6$, $C_7$, $C_8$, $C_9$, $C_{10}$, $C_{11}$, $C_{12}$, $C_{13}$, $C_{14}$, $C_{15}$ or $C_{16}$, as well as $C_{6-10}$, $C_{6-12}$, or $C_{6-14}$. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. Unless otherwise specified, "substituted aryl" groups can be substituted with one or more groups selected from halo, hydroxy, amino, alkylamino, amido, acyl, nitro, cyano, and alkoxy.

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of heteroatoms can be included in the heteroaryl groups, such as 1, 2, 3, 4; or 5, or 1 to 2, 1 to 3, 1 to 4, 1 to 5, 2 to 3, 2 to 4, 2 to 5, 3 to 4, or 3 to 5. For example, heteroaryl groups can be $C_{5-8}$ heteroaryl, wherein 1 to 4 carbon ring atoms are replaced with heteroatoms; or $C_{5-8}$ heteroaryl, wherein 1 to 3 carbon ring atoms are replaced with heteroatoms; or $C_{5-6}$ heteroaryl, wherein 1 to 4 carbon ring atoms are replaced with heteroatoms; or $C_{5-6}$ heteroaryl, wherein 1 to 3 carbon ring atoms are replaced with heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. Unless otherwise specified, "substituted heteroaryl" groups can be substituted with one or more groups selected from halo, hydroxy, amino, alkylamino, amido, acyl, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein, the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of carbon ring atoms can be replaced with heteroatoms in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. Unless otherwise specified, "substituted heterocyclyl" groups can be substituted with one or more groups selected from halo, hydroxy, amino, oxo, alkylamino, amido, acyl, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "protecting group" (or "PG") refers to a chemical moiety that renders a functional group (e.g., an amino group) unreactive, but is also removable so as to restore the amino group. Examples of protecting groups include, but are not limited to, ethers (e.g., methoxymethyl ether, p-methoxybenzyl ether, and the like); silyl ethers (e.g., trimethylsilyl ether, tert-butyldiphenylsilyl ether, and the like); benzyloxycarbonyl (Z or Cbz); 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other protecting groups are known to those of skill in the art including, for example, those described by Green and Wuts (*Protective Groups in Organic Synthesis*, 4$^{th}$ Ed. 2007, Wiley-Interscience, New York).

As used herein, the term "carbonyl," by itself or as part of another substituent, refers to —C(O)—, i.e., a carbon atom double-bonded to oxygen and bound to two other groups in the moiety having the carbonyl.

As used herein, the term "amino" refers to a moiety —NR$_2$, wherein each R group is H or alkyl. An amino moiety can be ionized to form the corresponding ammonium cation. "Dialkylamino" refers to an amino moiety wherein each R group is alkyl.

As used herein, the term "sulfonyl" refers to a moiety —SO$_2$R, wherein the R group is alkyl, haloalkyl, or aryl. An amino moiety can be ionized to form the corresponding ammonium cation. "Alkylsulfonyl" refers to an amino moiety wherein the R group is alkyl.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "acyl" refers to a moiety-C(O)R, wherein each R group is $C_{1-8}$ alkyl, $C_{3-8}$ cycloalkyl, or $C_{6-10}$ aryl as defined herein.

As used herein, the term "amido" refers to a moiety —NRC(O)R or —C(O)NR$_2$, wherein each R group is H or alkyl.

As used herein, the term "nitro" refers to the moiety —NO$_2$.

As used herein, the term "oxo" refers to an oxygen atom that is double-bonded to a compound (i.e., O═).

As used herein, the term "solubilizing moiety" refers to a moiety used to increase the solubility of a compounds of the invention in a solvent (e.g., water or an organic solvent).

Examples of solubilizing moieties include, but are not limited to, sugars (monosaccharides, oligosaccharides, and polysaccharides); polyols (e.g., glycerol, propylene glycol, and the like), synthetic polymers (e.g., hydrophilic polymers such as oligo (ethylene glycol), poly(ethylene glycols) (PEGs), poly-trimethylene glycols, poly(N-isopropylacrylamides) (NIPAMs), polyvinylpyrrolidones, polyoxyethylene-polyoxypropylene block copolymers, and the like) and biopolymers (e.g., proteins, starch, cellulose, heparin, hyaluronic acid, and the like).

As used herein, the term "monosaccharide" refers to a sugar having a five-membered carbon backbone (i.e., a pentose) or a six-membered carbon backbone (i.e., a hexose). Examples of monosaccharides include, but are not limited to, glucose, ribose, fucose, xylose, arabinose, galactose, mannose, glucuronic acid, and iduronic acid. Monosaccharides also include pentoses and hexoses substituted with hydroxy groups, oxo groups, amino groups, acetylamino groups, and other functional groups.

As used herein, the term "oligosaccharide" refers to a compound containing at least two monosaccharides covalently linked together. Oligosaccharides include disaccharides, trisaccharides, tetrasaccharides, pentasaccharides, hexasaccharides, heptasaccharides, octasaccharides, and the like. Covalent linkages for linking sugars generally consist of glycosidic linkages (i.e., C—O—C bonds) formed from the hydroxyl groups of adjacent sugars. Linkages can occur between the 1-carbon (the anomeric carbon) and the 4-carbon of adjacent sugars (i.e., a 1-4 linkage), the 1-carbon and the 3-carbon of adjacent sugars (i.e., a 1-3 linkage), the 1-carbon and the 6-carbon of adjacent sugars (i.e., a 1-6 linkage), or the 1-carbon and the 2-carbon of adjacent sugars (i.e., a 1-2 linkage). Other linkages can be present in the oligosaccharide, depending on the particular sugar subunits present. Those of skill in the art will appreciate that a sugar can be linked within an oligosaccharide such that the glycosidic bond at the anomeric carbon is in the α- or β-configuration.

As used herein, the term "polysaccharide" generally refers to a compound containing 10 or more sugars linked together as described for oligosaccharides.

As used herein, the term "salt" refers to acid or base salts of the compounds of the invention. Illustrative examples of pharmaceutically acceptable salts include mineral acid salts (salts of hydrochloric acid, hydrobromic acid, phosphoric acid, and the like), organic acid salts (salts of acetic acid, propionic acid, glutamic acid, citric acid and the like) salts, and quaternary ammonium salts (salts of methyl iodide, ethyl iodide, and the like). It is understood that the pharmaceutically acceptable salts are non-toxic. Additional information on suitable pharmaceutically acceptable salts can be found in *Remington: The Science & Practice of Pharmacy,* 20th ed., Lippincott Williams & Wilkins, Philadelphia, Pa., 2000, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Compounds of the present invention include all tautomers and stereoisomers thereof, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Any compound or formula given herein, is intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}$Cl, $^{123}$I and $^{125}$I, respectively. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^3$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

As used herein, the term "pharmaceutical composition" is intended to encompass a product comprising the specified ingredients in the specified amounts, as well as any product, which results, directly or indirectly, from combination of the specified ingredients in the specified amounts.

As used herein, the term "pharmaceutically acceptable excipient" refers to a substance that aids the administration of an active agent to a subject. By "pharmaceutically acceptable," it is meant that the excipient is compatible with the other ingredients of the formulation and is not deleterious to the recipient thereof. Pharmaceutical excipients useful in the present invention include, but are not limited to, binders, fillers, disintegrants, lubricants, glidants, coatings, sweeteners, flavors and colors.

As used herein, the terms "treat", "treating," and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter, including, e.g., the result of a physical examination.

As used herein, the terms "effective amount" and "therapeutically effective amount" refer to a dose of a compound, such as a carbon monoxide releasing compound, that brings about a result, e.g., a therapeutic effect, for which the compound was administered. When "effective amount" is used to describe an in vivo method, the desired result can refer to a therapeutic effect. When "effective amount" is used to describe an ex vivo method the desired results can refer to a detectable level of carbon monoxide. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); Goodman & Gilman's The Pharmacological Basis of Therapeutics, 11$^{th}$ Edition, 2006, Brunton, Ed., McGraw-Hill; and Remington: The Science and Practice of Pharmacy, 21$^{st}$ Edition, 2005, Hendrickson, Ed., Lippincott, Williams & Wilkins).

The terms "about" and "around," as used herein to modify a numerical value, indicate a close range surrounding that explicit value. If "X" were the value, "about X" or "around X" would indicate a value from 0.9X to 1.1X. "About X" thus includes, for example, a value from 0.95X to 1.05X, or from 0.98X to 1.02X, or from 0.99X to 1.01X. Any reference to "about X" or "around X" specifically indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.07X, 1.08X, 1.09X, and 1.10X. Accordingly, "about X" and "around X" are intended to teach and provide written description support for a claim limitation of, e.g., "0.98X."

III. Carbon Monoxide Releasing Compounds

The carbon monoxide releasing compounds of the invention include a cyclopentenone moiety (e.g., a bicyclo[2.2.1]hept-2-en-7-one) and a reactive moiety. Exposure of the reactive moiety to a change in pH, to reactive oxygen species, or to enzymatic activity, such as would occur upon exposure of the compound to physiological conditions upon administration to a subject, results in elimination of the reactive moiety and formation of an unstable dienone intermediate (e.g., a bicyclo[2.2.1]hepta-2,5-dien-7-one) which undergoes a pericyclic fragmentation process to release carbon monoxide.

In certain embodiments, the invention provides a compound according to Formula I:

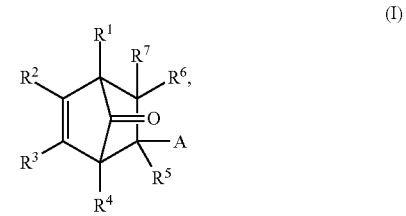

or a pharmaceutically acceptable salt thereof, wherein:
$R^1$, $R^2$, $R^3$, and $R^4$ are independently selected from the group consisting of H, $C_{1-8}$ alkyl, $C_{3-8}$ cycloalkyl, $C_{6-10}$ aryl, 3- to 8-membered heterocyclyl, 5- to 12-membered heteroaryl, and —C(O)OR$^8$;

$R^2$ and $R^3$ are optionally taken together to form a fused bicyclic moiety or a fused tricyclic moiety;

$R^5$ is selected from the group consisting of H, $C_{1-8}$ alkyl, —CN, —C(O)OR$^9$, —C(O)R$^{10}$, —C(O)N(R$^{11}$)$_2$, and a targeting moiety;

$R^6$ and $R^7$ are independently selected from the group consisting of H, $C_{1-8}$ alkyl, —CN, —C(O)OR$^9$, —C(O)R$^{10}$, —C(O)N(R$^{11}$)$_2$, —S(O)R$^{12}$, and S(O)$_2$R$^{12}$;

A is the reactive moiety, which is selected from the group consisting of —SeR$^{13}$, —OS(O)$_2$R$^{14}$, —SR$^{14}$, —S(O)R$^{14}$, —S(O)$_2$R$^{14}$, —OR$^{15}$, —OP(O)(OR$^{15}$)$_2$, —OC(O)R$^{16}$, —OC(O)N(R$^{17}$)$_2$, —N$^+$(R$^{17}$)$_3$, and halogen;

$R^8$ is selected from the group consisting of H and $C_{1-6}$ alkyl;

each $R^9$, $R^{10}$, $R^{11}$, and $R^{12}$ is independently selected from the group consisting of H, $C_{1-8}$ alkyl, $C_{2-8}$ acyl, $C_{6-10}$ aryl, and a targeting moiety;

each $R^{13}$, $R^{14}$, $R^{15}$, $R^{16}$, and $R^{17}$ are selected from the group consisting of $C_{1-8}$ alkyl, $C_{3-8}$ cycloalkyl, $C_{6-10}$ aryl, and 5- to 12-membered heteroaryl;

in $R^6$ or $R^7$, one of $R^9$, $R^{10}$, $R^{11}$, and $R^{12}$ is optionally taken together with one of $R^3$, $R^{14}$, $^R$, $R^{16}$, and $R^{17}$ to form a monocyclic moiety;

each of $R^1$-$R^7$ and $R^{13}$-$R^{17}$ is optionally and independently substituted with one or more substituents independently selected from the group consisting of halogen, $C_{1-4}$ alkyl, $C_{1-4}$ haloalkyl, —CN, —NO$_2$, —OR$^a$, —C(O)R$^b$, —C(O)OR$^a$, —OC(O)R$^b$, —N(R$^a$)$_2$, —NR$^a$C(O)R$^b$, —C(O)N(R$^a$)$_2$, —S(O)R$^b$, —S(O)$_2$R$^b$, —S(O)$_2$OR$^a$, —S(O)$_2$N(R$^a$)$_2$, and —NR$^a$S(O)$_2$R$^b$;

each $R^a$ is independently selected from the group consisting of H, $C_{1-4}$ alkyl, a solubilizing moiety, and a targeting moiety; and each $R^b$ is independently selected from the group consisting of $C_{1-4}$ alkyl, a solubilizing moiety, and a targeting moiety.

In some embodiments, compounds of Formula I are provided wherein:

$R^1$, $R^2$, $R^3$, and $R^4$ are independently selected from the group consisting of H, $C_{1-8}$ alkyl, $C_{3-8}$ cycloalkyl, $C_{6-10}$ aryl, 3- to 8-membered heterocyclyl, 5- to 12-membered heteroaryl, and —C(O)OR$^8$;

$R^2$ and $R^3$ are optionally taken together to form a fused bicyclic moiety or a fused tricyclic moiety;

$R^5$ is selected from the group consisting of H, $C_{1-8}$ alkyl, —CN, —C(O)OR$^9$, —C(O)R$^{10}$, —C(O)N(R$^{11}$)$_2$, and a targeting moiety;

$R^6$ and $R^7$ are independently selected from the group consisting of H, $C_{1-8}$ alkyl, —CN, —C(O)OR$^9$, —C(O)R$^{10}$, —C(O)N(R$^{11}$)$_2$, —S(O)R$^{12}$, and S(O)$_2$R$^{12}$;

A is selected from the group consisting of —SeR$^{13}$, —SR$^{14}$, —OS(O)$_2$R$^{14}$, —S(O)R$^{14}$, —S(O)$_2$R$^{14}$, —OR$^{15}$, —OP(O)(OR$^{15}$)$_2$, —OC(O)R$^{16}$, —OC(O)N(R$^{17}$)$_2$, —N$^+$(R$^{17}$)$_3$, and halogen;

$R^8$ is selected from the group consisting of H and $C_{1-6}$ alkyl;

each $R^9$, $R^{10}$, $R^{11}$, and $R^{12}$ is independently selected from the group consisting of H, $C_{1-6}$ alkyl, and a targeting moiety;

each $R^{13}$, $R^{14}$, $R^{15}$, $R^{16}$, and $R^{17}$ are selected from the group consisting of $C_{1-8}$ alkyl, $C_{3-8}$ cycloalkyl, and $C_{6-10}$ aryl;

each of $R^1$-$R^7$ and $R^{13}$-$R^{17}$ is optionally and independently substituted with one or more substituents independently selected from the group consisting of halogen, $C_{1-4}$ alkyl, $C_{1-4}$ haloalkyl, —CN, —NO$_2$, —OR$^a$, —C(O)R$^b$, —C(O)OR$^a$, —OC(O)R$^b$, —N(R$^a$)$_2$, —NR$^a$C(O)R$^b$, —C(O)N(R$^a$)$_2$, —S(O)R$^b$, —S(O)$_2$R$^b$, —S(O)$_2$OR$^a$, —S(O)$_2$N(R$^a$)$_2$, and —NR$^a$S(O)$_2$R$^b$;

each $R^a$ is independently selected from the group consisting of H, $C_{1-4}$ alkyl, a solubilizing moiety, and a targeting moiety; and each $R^b$ is independently selected from the group consisting of $C_{1-4}$ alkyl, a solubilizing moiety, and a targeting moiety.

$R^1$ and $R^4$ in compounds of Formula I are generally selected from H, $C_{1-8}$ alkyl, $C_{3-8}$ cycloalkyl, $C_{6-10}$ aryl, 3- to 8-membered heterocyclyl, 5- to 12-membered heteroaryl, and —C(O)OR$^8$. For example, $R^1$ and/or $R^4$ can be H, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, or branched octyl. In some embodiments, $R^1$ and/or $R^4$ is selected from cyclopropyl, cyclobutyl, cyclopentyl, cyclohexyl, cycloheptyl, and cyclooctyl. In some embodiments, $R^1$ and/or $R^4$ is selected from cyclobutyl, cyclopentyl, and cyclohexyl. In some embodiments, $R^1$ and/or $R^4$ is selected from phenyl, naphthyl, and biphenyl. In some embodiments, $R^1$ and/or $R^4$ is selected from piperazinyl, pyrrolidinyl, dioxanyl, morpholinyl, and tetrahydrofuranyl. In some embodiments, $R^1$ and/or $R^4$ is selected from pyrrolyl, pyridinyl, imidazolyl, pyrazolyl, triazolyl, pyrazinyl, triazinyl, indolyl, isoindolyl, and quinolinyl.

In some embodiments, $R^1$ is —C(O)R$^8$. $R^8$ in compounds of Formula I is generally selected from H and $C_{1-8}$ alkyl. For example, $R^8$ can be H, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, or branched octyl.

In some embodiments, $R^2$ and $R^3$ are taken together to form a fused bicyclic moiety or a fused tricyclic moiety. In some embodiments, the fused bicyclic moiety is an unsaturated aliphatic hydrocarbon moiety containing 5 to 12 carbon ring atoms. Examples of fused bicyclic moieties include, but are not limited to, bicyclopentenediyl (e.g., bicyclo[1.1.1]pent-1-en-1,2-diyl or bicyclo[2.1.0]pent-2-en-2,3-diyl), bicyclohexenediyl (e.g., bicyclo[2.1.1]hex-2-en-2,3-diyl), bicycloheptenediyl (e.g., bicyclo[2.2.1]hept-2-en-2,3-diyl), and bicyclooctenediyl (e.g., bicyclo[2.2.2]oct-2-en-2,3-diyl).

In some embodiments, the fused tricyclic moiety is a saturated or unsaturated aliphatic hydrocarbon moiety containing 6 to 12 carbon ring atoms. Examples of fused tricyclic moieties include, but are not limited to, tricyclodecenediyl (e.g., adamantenediyl, also referred to as tricyclo[3.3.1.1$^{3,7}$]decenediyl, such as tricyclo[3.3.1$^{3,7}$]dec-1-en-1,2-diyl) and tricycloundecenediyl (e.g., tricyclo[4.3.1.1$^{3,8}$]undec-4-en-4,5-diyl). In some embodiments, $R^2$ and $R^3$ are taken together to form the fused tricyclic moiety tricyclo[4.3.1.1$^{3,8}$]undec-4-en-4,5-diyl, having the structure:

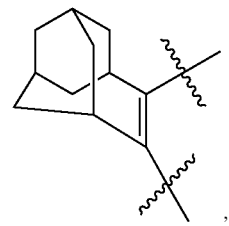 [SMILES: *C1=C(*)C2CC3CC(CC1C3)C2]

wherein the wavy lines represent the points of attachment to Formula I, or to Formula Ia, Formula Ib, or Formula Ic as described below.

In some embodiments, $R^2$ is selected from the group consisting of H, $C_{1-8}$ alkyl, $C_{3-8}$ cycloalkyl, $C_{6-10}$ aryl, 3- to 8-membered heterocyclyl, 5- to 12-membered heteroaryl, and —C(O)OR$^8$, and $R^3$ is selected from the group consisting of H, $C_{1-8}$ alkyl, $C_{3-8}$ cycloalkyl, $C_{6-10}$ aryl, 3- to 8-membered heterocyclyl, 5- to 12-membered heteroaryl, and —C(O)OR$^8$. Each $R^8$ is independently selected from the group consisting of H and $C_{1-6}$ alkyl.

In some embodiments, $R^2$ and/or $R^3$ is selected from H, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, and branched octyl. In some embodiments, $R^2$ and/or $R^3$ is selected from cyclopropyl, cyclobutyl, cyclopentyl, cyclohexyl, cycloheptyl, and cyclooctyl. In some embodiments, $R^2$ and/or $R^3$ is selected from cyclobutyl, cyclopentyl, and cyclohexyl. In some embodiments, $R^2$ and/or $R^3$ is selected from phenyl, naphthyl, and biphenyl. In some embodiments, $R^2$ and/or $R^3$ is selected from piperazinyl, pyrrolidinyl, dioxanyl, morpholinyl, and tetrahydrofuranyl. In some embodiments, $R^2$ and/or $R^3$ is selected from pyrrolyl, pyridinyl, imidazolyl, pyrazolyl, triazolyl, pyrazinyl, triazinyl, indolyl, isoindolyl, and quinolinyl.

In some embodiments, $R^2$ is —C(O)R$^8$ and/or $R^3$ is —C(O)R$^8$. $R^8$ in compounds of Formula I is generally selected from H and CL-s alkyl. For example, $R^8$ can be H, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, or branched octyl.

$R^5$ in compounds of Formula I is generally selected from the group consisting of H, $C_{1-8}$ alkyl, —CN, —C(O)OR$^9$, —C(O)R$^{10}$, —C(O)N(R$^{11}$)$_2$, and a targeting moiety, and each $R^9$, $R^{10}$, and $R^{11}$ are independently selected from the group consisting of H, $C_{1-6}$ alkyl, and a targeting moiety. $R^6$ and $R^7$ are generally selected from the group consisting of H, $C_{1-8}$ alkyl, —CN, —C(O)OR$^9$, —C(O)R$^{10}$, —C(O)N(R$^{11}$)$_2$, and a targeting moiety, and each $R^9$, $R^{10}$, and $R^{11}$ are independently selected from the group consisting of H, $C_{1-6}$ alkyl, and a targeting moiety.

In some embodiments, $R^5$ and/or $R^6$ is selected from H, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, or branched octyl. In some embodiments, $R^5$ and/or $R^6$ is —CN. In some embodiments, $R^5$ is selected from —C(O)OR$^9$ and —C(O)R$^{10}$ and/or $R^6$ is selected from —C(O)OR$^9$ and —C(O)R$^{10}$. In some embodiments, $R^5$ is —C(O)N(R$^{11}$)$_2$ and/or $R^6$ is —C(O)N(R$^{11}$)$_2$.

In some embodiments, each $R^9$, $R^{10}$, and $R^{11}$ is independently selected from H and $C_{1-6}$ alkyl. For example, $R^9$, $R^{10}$, and $R^{11}$ can be H, methyl, ethyl, n-propyl, isopropyl, n-butyl, isobutyl, tert-butyl, n-pentyl, branched pentyl, n-hexyl, or branched hexyl.

In some embodiments, any one $R^9$, $R^{10}$, and $R^{11}$, or any combination thereof, is a targeting moiety. Generally, the targeting moieties will be able to associate with a target of interest, such as a target associated with an organ, tissues, cell, extracellular matrix, or intracellular region. In certain embodiments, a target can be associated with a particular disease state, such as a cancerous condition. In some embodiments, the targeting moiety can be specific to only one target, such as a receptor. Suitable targets include, but are not limited to, a nucleic acid, such as a DNA, RNA, or modified derivatives thereof. Suitable targets can also include proteins, such as an extracellular protein, a receptor, a cell surface receptor, a tumor-marker, a transmembrane protein, an enzyme, or an antibody. Suitable targeting moieties can include a carbohydrate, such as a monosaccharide, disaccharide, or polysaccharide that can be, for example, present on the surface of a cell.

In certain embodiments, a targeting moiety can include a target ligand (e.g., an RGD-containing peptide) or a small molecule mimic of a target ligand (e.g., a peptide mimetic ligand). In some embodiments, a targeting moiety can further include folic acid derivatives, B-12 derivatives, integrin RGD peptides, NGR derivatives, somatostatin derivatives or peptides that bind to the somatostatin receptor, e.g., octreotide and octreotate, and the like.

In some embodiments, the targeting moiety is a mitochondrial targeting moiety. In certain embodiments, the mitochondria are targeted with a targeting moiety containing a positively-charged functional group that can be taken up by the mitochondria due to the electrochemical gradient built across the inner mitochondrial membrane by respiratory chain complexes. Examples of positively-charged mitochondrial targeting moieties include, but are not limited to, phosphonium moieties, quinolizinium moieties, and benzoxazolium moieties.

The "A" moiety in compounds of Formula I is selected from the group consisting of —SeR$^{13}$, —SR$^{14}$, —OS(O)$_2$R$^{14}$, —S(O)R$^{14}$, —S(O)$_2$R$^{14}$, —OR$^{15}$, —OP(O)(OR$^{15}$)$_2$, —OC(O)R$^{16}$, —OC(O)N(R$^7$)$_2$, —N$^+$(R$^{17}$)$_3$, and halogen. In some embodiments, A is selected from —SeR$^{13}$, —SR$^{14}$, —OS(O)$_2$R$^{14}$, —S(O)R$^{14}$, —S(O)$_2$R$^{14}$, —OR$^{15}$, —OP(O)(OR$^{15}$)$_2$, —OC(O)R$^{16}$, —OC(O)N(R$^{17}$)$_2$, and —N$^+$(R$^{17}$)$_3$.

In some embodiments, $R^{13}$, $R^{14}$, and/or $R^{15}$ is selected from the group consisting of $C_{1-8}$ alkyl, $C_{3-8}$ cycloalkyl, and $C_{6-10}$ aryl. For example, $R^{13}$, $R^{14}$, and/or $R^{15}$ can be methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, or branched octyl. In some embodiments, $R^{13}$, $R^{14}$, and/or $R^{15}$ is selected from cyclopropyl, cyclobutyl, cyclopentyl, cyclohexyl, cycloheptyl, and cyclooctyl. In some embodiments, $R^{13}$, $R^{14}$, and/or $R^{15}$ is selected from phenyl, naphthyl, and biphenyl.

Each of the $R^1$-$R^7$ and $R^{13}$-$R^{17}$ substituents of Formula I are optionally and independently substituted with one or substituents independently selected from the group consisting of $C_{1-4}$ alkyl, halogen, —CN, —OR$^a$, —C(O)R$^b$, —C(O)OR$^a$, —OC(O)R$^b$, —N(R$^a$)$_2$, —NR$^a$C(O)R$^b$, —C(O)N(R$^a$)$_2$, —S(O)R$^b$, —S(O)$_2$R$^b$, —S(O)$_2$OR$^a$, —S(O)$_2$N(R$^a$)$_2$, and —NR$^a$S(O)$_2$R$^b$ Generally, each $R^a$ substituent is independently selected from the group consisting of H, $C_{1-4}$ alkyl, a solubilizing moiety, and a targeting moiety. Each $R^b$ substituent is an independently-selected $C_{1-4}$ alkyl group, a solubilizing moiety, or a targeting moiety. For example, $R^a$ and/or $R^b$ can be methyl, ethyl, n-propyl, isopropyl, n-butyl, sec-butyl, isobutyl, or tert-butyl.

Alternatively, $R^a$ and/or $R^b$ can be a targeting moiety as described above or a solubilizing moiety. A number of suitable solubilizing moieties can be use in compounds of the invention. For example, $R^a$ and/or $R^b$ can be propylene glycol, an oligo (ethylene glycol), a poly(ethylene glycol), a poly(N-isopropylacrylamide), a polyvinylpyrrolidone, or a monosaccharide.

In some embodiments, the invention provides compounds of Formula I wherein $R^2$ and $R^3$ are independently selected from the group consisting of $C_{3-8}$ cycloalkyl, $C_{6-10}$ aryl, 3- to 8-membered heterocyclyl, and 5- to 12-membered heteroaryl.

In some embodiments, the invention provides compounds according to Formula Ia:

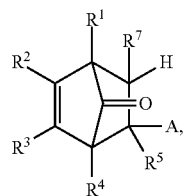

wherein A is selected from the group consisting of —SeR$^{13}$ and —SR$^{14}$. In some embodiments, A is in the cis configuration with respect to proton H. In some embodiments, A is in the trans configuration with respect to proton H.

In some embodiments, the invention provides compounds of Formula I or Formula Ia, wherein R$^1$ and R$^4$ are independently selected from the group consisting of C$_{1-8}$ alkyl, C$_{6-10}$ aryl, and —C(O)OR$^8$. In some embodiments, R$^5$ in compounds of Formula I or Ia is selected from the group consisting of H, —C(O)OR$^9$, and —C(O)N(R$^{11}$)$_2$. In some embodiments, R$^9$ is H or methyl. In some embodiments, each R$^{11}$ is independently selected from the group consisting of H and a targeting moiety. In some such embodiments, the targeting moiety is a mitochondrial targeting moiety. In some such embodiments, the mitochondrial targeting moiety comprises a phosphonium group.

In some embodiments, the invention provides compounds of Formula I or Formula Ia, wherein R$^1$ and R$^4$ are independently selected from methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, and branched octyl. In some embodiments, R$^1$ and R$^4$ are methyl. In some embodiments, R$^1$ and R$^4$ are methyl and R$^5$ is H. In some embodiments, R$^1$ and R$^4$ are methyl and R$^5$ is selected from H and —C(O)OR$^9$. In some such embodiments, R$^9$ is selected from H, methyl, ethyl, n-propyl, isopropyl, n-butyl, sec-butyl, isobutyl, and tert-butyl. In some such embodiments, R$^9$ is selected from H and methyl. In some embodiments, the invention provides compounds of Formula Ia, wherein R$^1$ and R$^4$ are methyl, R$^5$ is H, and R$^7$ is H. In some embodiments, the invention provides compounds of Formula Ia, wherein R$^1$ and R$^4$ are methyl, R$^5$ is —C(O)OR$^9$, R$^9$ is selected from H and methyl, and R$^6$ and R$^7$ are H. In some embodiments, R$^1$ and R$^4$ are methyl, R$^5$ is H, R$^7$ is —C(O)R$^{10}$, and R$^{10}$ is H.

In some embodiments, the invention provides compounds of Formula I or Formula Ia, wherein R$^1$ and R$^4$ are independently selected from phenyl and naphthyl. In some embodiments, R$^1$ and R$^4$ are phenyl. In some embodiments, R$^1$ and R$^4$ are phenyl and R$^5$ is H. In some embodiments, R$^1$ and R$^4$ are phenyl and R$^5$ is selected from H and —C(O)OR$^9$. In some such embodiments, R$^9$ is selected from H, methyl, ethyl, n-propyl, isopropyl, n-butyl, sec-butyl, isobutyl, and tert-butyl. In some such embodiments, R$^9$ is selected from H and methyl. In some embodiments, the invention provides compounds of Formula Ia, wherein R$^1$ and R$^4$ are phenyl, R$^5$ is H, and R$^6$ and R$^7$ are H. In some embodiments, the invention provides compounds of Formula Ia, wherein R$^1$ and R$^4$ are phenyl, R$^5$ is —C(O)OR$^9$, R$^9$ is selected from H and methyl, and R$^6$ and R$^7$ are H.

In some embodiments, the invention provides compounds of Formula I or Formula Ia, wherein R$^1$ and R$^4$ are —C(O)OR$^8$, and each R$^8$ is independently selected from H, methyl, ethyl, n-propyl, isopropyl, n-butyl, sec-butyl, isobutyl, and tert-butyl. In some embodiments, R$^1$ and R$^4$ are independently selected from —C(O)OH and —C(O)OCH$_3$. In some embodiments, R$^1$ and R$^4$ are independently selected from —C(O)OH and —C(O)OCH$_3$ and R$^5$ is H. In some embodiments, R$^1$ and R$^4$ are independently selected from —C(O)OH and —C(O)OCH$_3$ and R$^5$ is selected from H and —C(O)OR$^9$. In some such embodiments, R$^9$ is selected from H, methyl, ethyl, n-propyl, isopropyl, n-butyl, sec-butyl, isobutyl, and tert-butyl. In some such embodiments, R$^9$ is selected from H and methyl. In some embodiments, the invention provides compounds of Formula Ia, wherein R$^1$ and R$^4$ are selected from —C(O)OH and —C(O)OCH$_3$, R$^5$ is H, and R$^6$ and R$^7$ are H. In some embodiments, the invention provides compounds of Formula Ia, wherein R$^1$ and R$^4$ are —C(O)OCH$_3$, R$^5$ is —C(O)OR$^9$, R$^9$ is selected from H and methyl, and R$^6$ and R$^7$ are H.

In some embodiments, the invention provides compounds of Formula I or Formula Ia, wherein R$^1$ and R$^4$ are independently selected from the group consisting of C$_{1-8}$ alkyl, C$_{6-10}$ aryl, and —C(O)OR$^8$, and R$^5$ is —C(O)NHR$^{11}$, wherein R$^{11}$ is a targeting moiety. In some such embodiments, R$^{11}$ is —C$_{1-6}$ alkylene-P$^+$(R)$_3$, wherein each R is selected from the group consisting of C$_{1-8}$ alkyl and C$_{6-10}$ aryl. In some such embodiments, R$^{11}$ is —C$_{1-6}$ alkylene-P$^+$(Ph)$_3$ wherein each Ph is an optionally substituted phenyl group.

In some embodiments, R$^{13}$ or R$^{14}$ in compounds of Formula I or Formula Ia is selected from the group consisting of C$_{1-8}$ alkyl and C$_{6-10}$ aryl. R$^{13}$ or R$^{14}$ can be, for example, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, branched octyl, phenyl, naphthyl, or biphenyl.

In some embodiments, the compound is selected from the group consisting of:

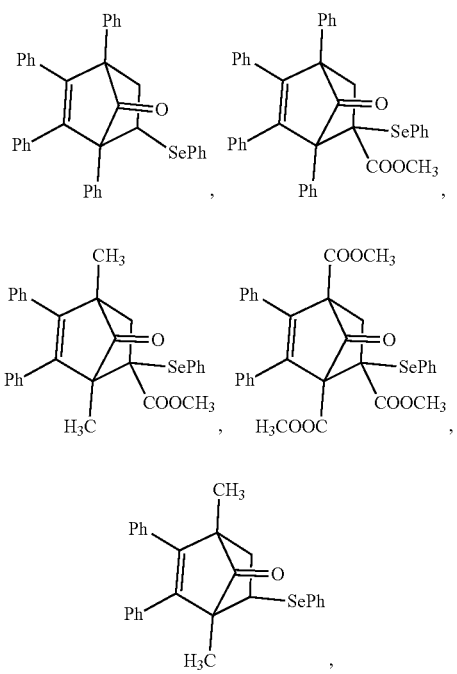

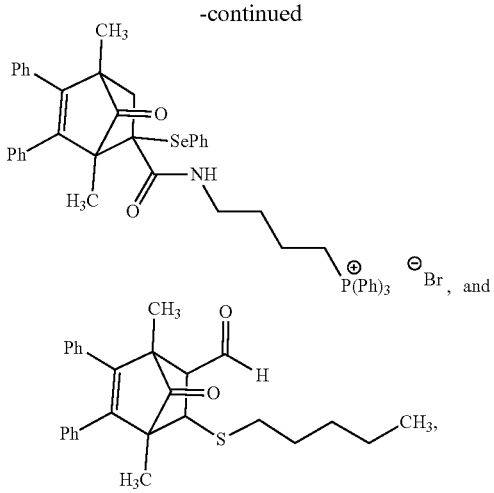

wherein Ph represents phenyl.

In some embodiments, the invention provides compounds having a structure according to Formula Ib:

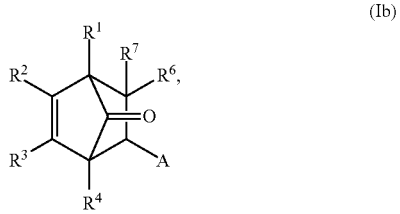

(Ib)

wherein A is selected from the group consisting of —SR$^{14}$, —S(O)R$^{14}$, —S(O)$_2$R$^{14}$, and —OR$^{15}$. In some embodiments, R$^7$ is H, which is in the trans configuration with respect to A. In some embodiments, A is selected from the group consisting of —S(O)R$^{14}$, —S(O)$_2$R$^{14}$, and —OR$^{15}$, and R$^7$ is H.

In some embodiments, R$^7$ is H, R$^6$ is —C(O)R$^{10}$, and R$^{10}$ is H in compounds of Formula I or Formula Ib. In some embodiments, R$^7$ is H and R$^6$ is —S(O)R$^{12}$ or —S(O)$_2$R$^{12}$ in compounds of Formula I or Formula Ib. In some embodiments, R$^6$ is —S(O)$_2$R$^{12}$ and R$^{12}$ is C$_{6-10}$ aryl. R$^{12}$ can be, for example, unsubstituted phenyl, halophenyl, cyanophenyl, nitrophenyl, alkylphenyl, unsubstituted naphthyl, halonaphthyl, cyanonaphthyl, nitronaphthyl, alkylnaphthyl, unsubstituted biphenyl, halobiphenyl, cyanobiphenyl, nitrobiphenyl, or alkylbiphenyl.

In some embodiments, R$^7$ is H and R$^6$ is taken together with one of R$^{13}$, R$^{14}$, R$^{15}$, R$^{16}$, and R$^{17}$ in reactive moiety A to form a monocyclic moiety (e.g., a 5-, 6-, 7-, or 8-membered saturated or unsaturated ring). When R$^6$ is alkyl, for example, R$^6$ can be taken together with R$^{13}$ to form a fused selenopyran moiety or a fused selenophene moiety. Alternatively, R$^6$ can be taken together with R$^{14}$ to form a fused thiopyran moiety, a fused thiophene moiety, or an oxidized form thereof (e.g., a fused thiophene 1,1-dioxide). By way of further example, when R$^6$ is —C(O)R$^{10}$, R$^6$ can be taken together with R$^{13}$ or R$^{14}$ to form an oxo-substituted fused selenopyran moiety, an oxo-substituted fused selenophene moiety, an oxo-substituted fused thiopyran moiety, or an oxo-substituted fused thiophene moiety. In some embodiments, R$^6$ in compounds of Formula I or Formula Ib is —C(O)R$^{10}$, and R$^{10}$, is taken together with R$^{14}$ or R$^{15}$ A to form a monocyclic moiety. For example, R$^{10}$ and R$^{14}$ can be taken together to form a fused thiopyran moiety, e.g., a fused tetrahydro-4H-thiopyran-4-one moiety, or an oxidized form such as a tetrahydro-4H-thiopyran-4-one 1,1-dioxide moiety. Similarly, R$^{10}$ and R$^{15}$ can be taken together to form a fused pyran moiety, e.g., a fused tetrahydro-4H-pyran-4-one moiety.

In some embodiments, the invention provides compounds having a structure according to Formula Ic:

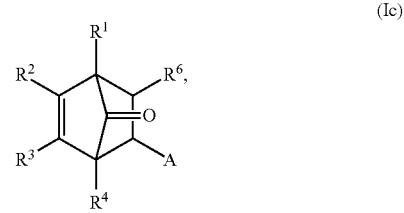

(Ic)

wherein R$^6$ is selected from the group consisting of —CH(OR$^{10}$)$_2$ and —CH(SR$^{10}$)$_2$; and A is selected from the group consisting of —SR$^{14}$, —S(O)R$^{14}$, —S(O)$_2$R$^{14}$, and —OR$^{15}$.

In some embodiments, the invention provides compounds of Formula I, Formula Ib, or Formula Ic, wherein R$^1$ and R$^4$ are independently selected from the group consisting of C$_{1-8}$ alkyl, C$_{6-10}$ aryl, and —C(O)OR$^8$. In some embodiments, R$^{14}$ or R$^{15}$ in compounds of Formula I, Formula Ib, or Formula Ic, is selected from the group consisting of optionally substituted phenyl and optionally substituted 5- to 12-membered heteroaryl. For example, R$^{14}$ or R$^{15}$ can be unsubstituted phenyl, halophenyl, cyanophenyl, nitrophenyl, alkylphenyl, pyrrolyl, pyridinyl, imidazolyl, pyrazolyl, thiazolyl, triazolyl, pyrazinyl, triazinyl, benzothiazolyl, benzimidazolyl, benzoxazolyl, benzisoxazolyl, indazolyl, indolyl, isoindolyl, or quinolinyl. In some embodiments, R$^{14}$ or R$^{15}$ in compounds of Formula I, Formula Ib, or Formula Ic is optionally substituted phenyl. In some embodiments, R$^{14}$ or R$^{15}$ is selected from the group consisting of halophenyl, cyanophenyl, nitrophenyl, and alkylphenyl. In some embodiments, R$^{14}$ or R$^{15}$ is selected from the group consisting of 4-fluorophenyl, 4-chlorophenyl, 4-nitrophenyl, and 4-methylphenyl. In some embodiments, R$^{14}$ or R$^{15}$ is unsubstituted phenyl. In some embodiments, R$^{14}$ or R$^{15}$ is benzothiazolyl (e.g., benzo[d]thiazol-2-yl), benzimidazolyl (e.g., benzo[d]imidazol-2-yl), benzoxazolyl (e.g., benzo[d]oxazol-2-yl), benzisoxazolyl (e.g., benzo[d]isoxazol-3-yl), indazolyl (e.g., 1H-idazol-3-yl), indolyl (e.g., 1H-indol-3-yl), isoindolyl (e.g., 1H-isoindol-3-yl), or quinolinyl (e.g., quinolin-2-yl). In some embodiments R$^{14}$ or R$^{15}$ is benzo[d]thiazol-2-yl.

In some embodiments, the invention provides compound of Formula I, Formula Ib, or Formula Ic, wherein R$^1$ and R$^4$ are selected from the group consisting of methyl, ethyl, n-propyl, isopropyl, n-butyl, sec-butyl, isobutyl, and tert-butyl and R$^{14}$ or R$^{15}$ is optionally substituted phenyl. In some such embodiments, R$^5$ is H. In some such embodiments, R$^6$ is —C(O)H and R$^7$ is H.

In some embodiments, the invention provides compounds of Formula Ib wherein R$^1$ and R$^4$ are methyl and R$^{14}$ or R$^{15}$ is optionally substituted phenyl. In some such embodiments, R$^5$ is H. In some such embodiments, R$^6$ is —C(O)H and R$^7$ is H.

In some embodiments, the invention provides compounds of Formula Ib wherein R$^1$ and R$^4$ are independently selected from the group consisting of methyl, ethyl, n-propyl, isopropyl, n-butyl, sec-butyl, isobutyl, and tert-butyl, and $R^{14}$ or $R^{15}$ is unsubstituted phenyl, 4-fluorophenyl, 4-chlorophenyl, 4-nitrophenyl, and 4-methylphenyl. In some such embodiments, $R^5$ is H. In some such embodiments, $R^6$ is —C(O)H and one $R^7$ is H.

In some embodiments, the compound selected from the group consisting of:

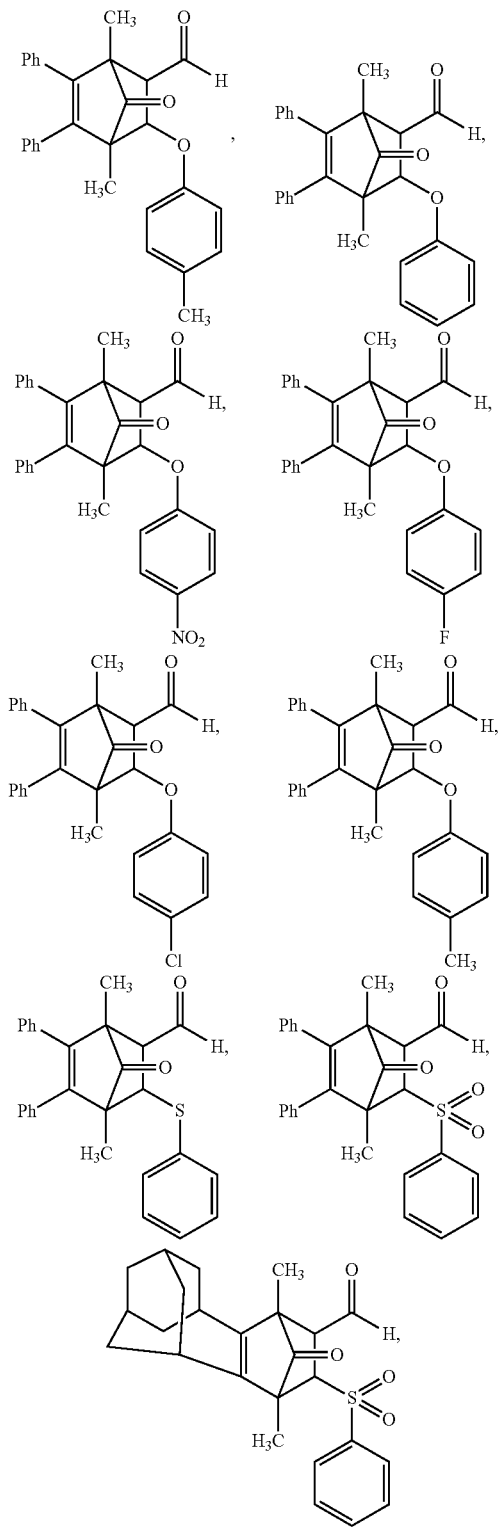

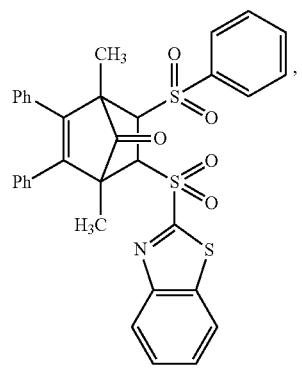

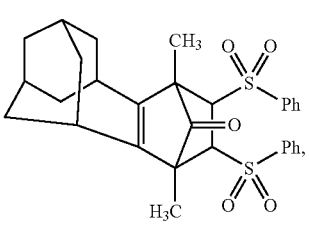

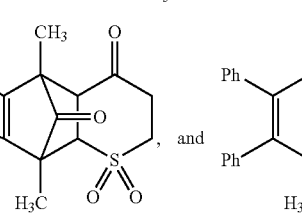

wherein Ph represents phenyl.

In some embodiments, the compound selected from the group consisting of:

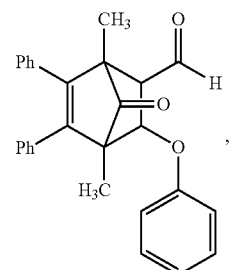
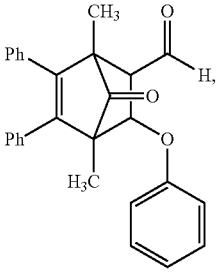
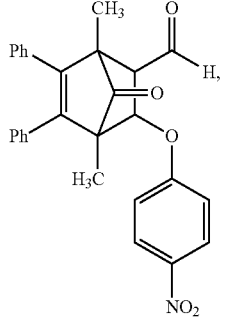
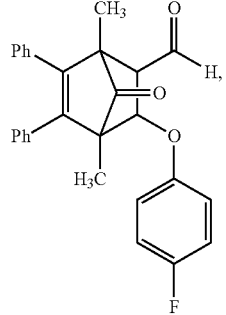

-continued

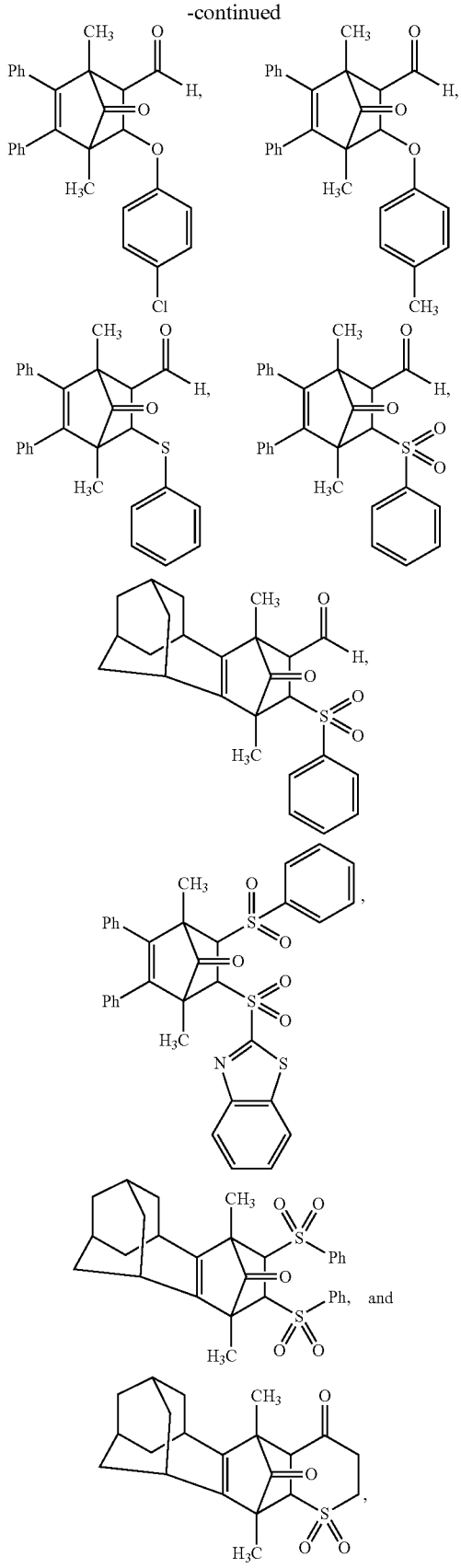

wherein Ph represents phenyl.

In some embodiments, the invention provides compound of Formula Ic wherein A is selected from the group consisting of —S(O)$R^{14}$, —S(O)$_2R^{14}$, and O$R^{15}$. In some embodiments, the invention provides compound of Formula Ic wherein $R^{10}$ is $C_{1-8}$ alkyl which is optionally substituted with —C(O)O$R^a$. For example, each $R^{10}$ can be methyl, ethyl, isopropyl, methyl, ethyl, n-propyl, isopropyl, n-butyl, sec-butyl, or isobutyl, each of which is optionally substituted with COOH or COOCH$_3$. In some embodiments, the compound of Formula Ic is:

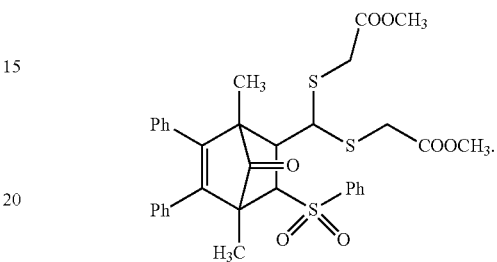

In some embodiments, $R^{10}$ is $C_{2-8}$ acyl in compounds of Formula Ic such that $R^6$ is a geminal diester or a geminal dithioester. $R^{10}$ can be, for example, acetyl, propanoyl, butanoyl, (cyclopropyl)carbonyl, (cyclobutyl)carbonyl, (cyclopentyl)carbonyl or the like. In some embodiments, the compound of Formula Ic is selected from:

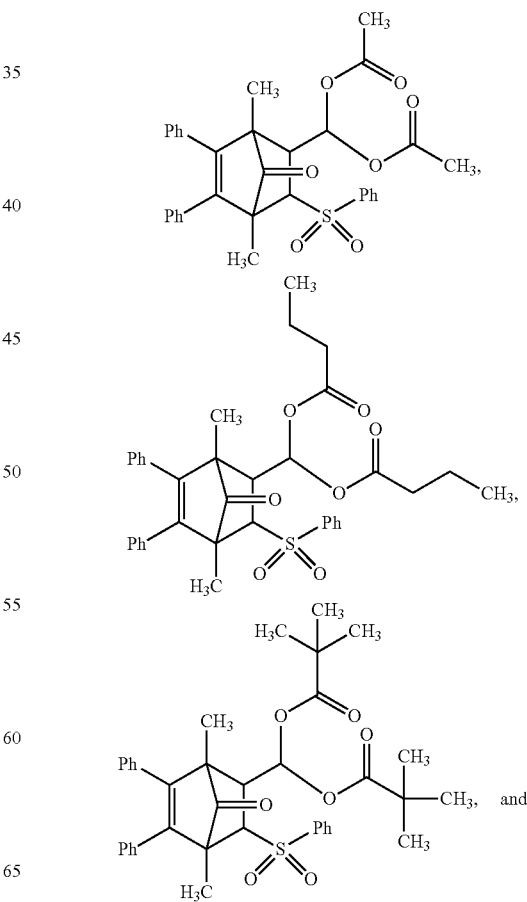

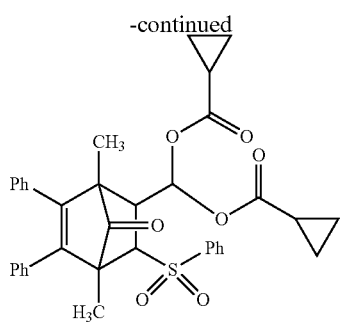

The compounds described herein may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. It will be appreciated that where typical or preferred process conditions (e.g., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). *Greene's protective groups in organic synthesis*. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$_{th}$ Edition, 2001), and Larock's Comprehensive Organic Transformations (VCH Publishers Inc., 1989).

The terms "solvent," "inert organic solvent," or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

Carbon monoxide-releasing compounds can be prepared, for example, according to the general route depicted in Scheme 1. Alochol/thiol/selenol A can be alkylated with acetylene B in the presence of a base (e.g., potassium carbonate) to form ether/thioether/selenoether-substituted alkyne C. Alkyne C and cyclopentadienone D can be reacted via a Diels Alder-type reaction to provide cyclopentenone E, i.e., a compound of Formula I where reactive moiety A is a leaving group —SeR$^{13}$, —SR$^{14}$, or —OR$^{15}$. A sulfonic acid or sulfonate salt can be used in place of the thiol for the preparation of compounds with leaving groups —S(O)R$^{14}$ or —S(O)$_2$R$^{14}$. In certain instances, the acetylene starting material will contain a functional group R$^{6a}$ which is converted to R$^6$ in one or more steps before or after the alkylation step or the Diels Alder step. For example, an ester group R$^{6a}$ (e.g., —COOMe) can be reduced to the corresponding alcohol (—CH$_2$OH) and oxidized to provide an aldehyde group R$^6$ (—C(O)H). The reduction and oxidation steps can be conducted before or after the Diels Alder reaction, and alcohol protecting groups can be used if an alcohol intermediate is carried through one or more reactions.

Scheme 1

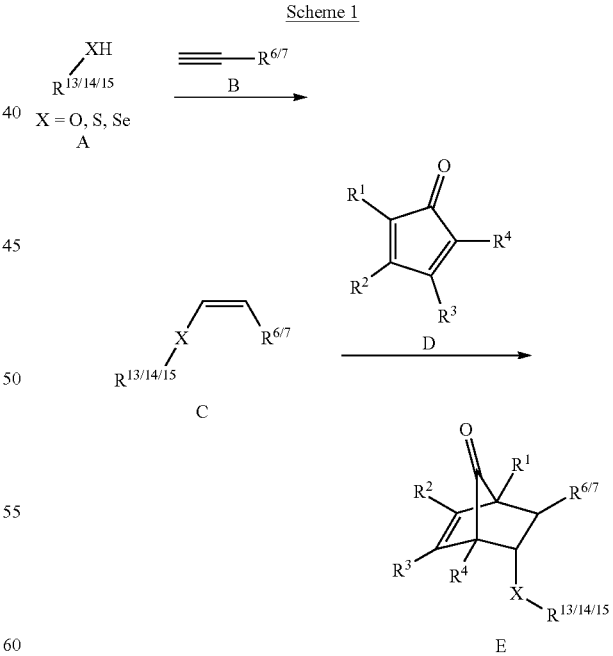

IV. Methods of Forming and Releasing Carbon Monoxide

In another aspect, the invention provides methods for forming and/or releasing carbon monoxide. The methods include exposing a carbon monoxide releasing compound as described to physiological conditions, wherein the compound comprises a cyclopentenone moiety and a leaving group precursor. Changes in pH (e.g., a decrease in pH) and/or exposure to reactive oxygen species in the physiological milieu results in elimination of the reactive moiety, formation of a bicyclo[2.2.1]hepta-2,5-dien-7-one intermediate, and subsequent fragmentation to release carbon monoxide.

In some embodiments, the invention provides carbon monoxide releasing compounds which function by a mechanism shown in Scheme 2A.

Scheme 2A

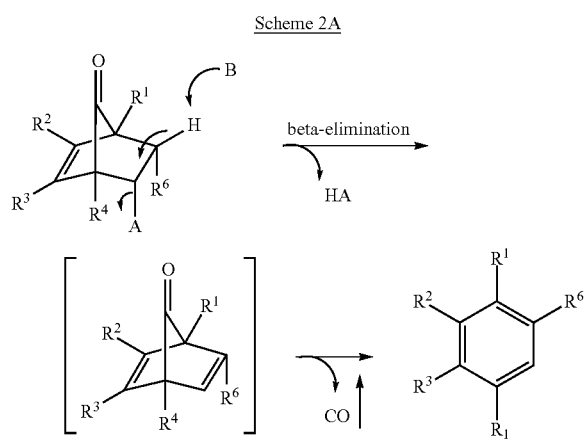

In some embodiments, the reactive moiety in the carbon monoxide releasing compound is a leaving group and a change in pH upon exposure to physiological conditions results in elimination of the leaving group. In some embodiments, increasing the pH from below 4 to around 7.2 (or higher) results in elimination of the leaving group. For example, the pH can be increased from below 7 to around 7.2 or higher, or from below 6 to around 7.2 or higher, or from below 5 to around 7.2 or higher, or from below 4 to around 7.2 or higher, or from below 3 to around 7.2 or higher.

In some embodiments, the invention provides carbon monoxide releasing compounds which function by a mechanism shown in Scheme 2B.

Scheme 2B

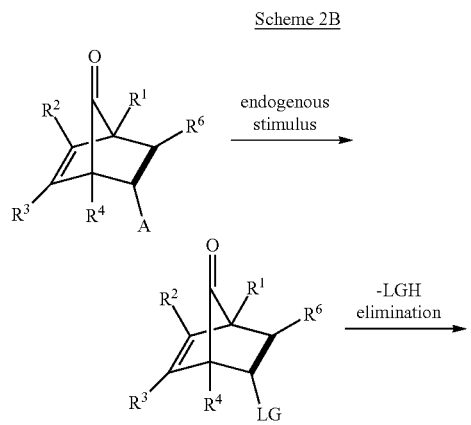

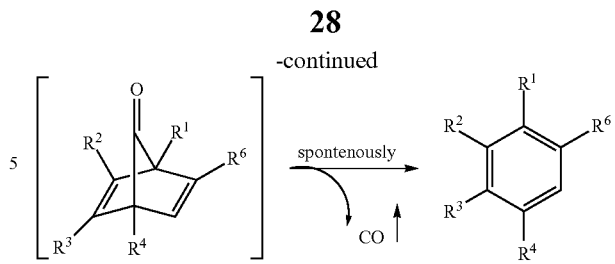

In certain embodiments, the reactive moiety in the carbon-monoxide releasing compound is a leaving group precursor. Exposure of the leaving group precursor to reactive oxygen species upon exposure to physiological conditions results in formation of a leaving group. and elimination of the leaving group. In certain embodiments, the leaving group precursor is a phenylselenyl group, which is sensitive to reactive oxygen species (ROS) such as peroxides, superoxide, hydroxyl radicals, and singlet oxygen in physiological environments. Elevated levels of ROS are frequently present in cells and tissues affected by cancer, bacterial infection, and inflammation.

In some embodiments, the invention provides carbon monoxide releasing compounds which function by a mechanism shown in Scheme 3.

Scheme 3

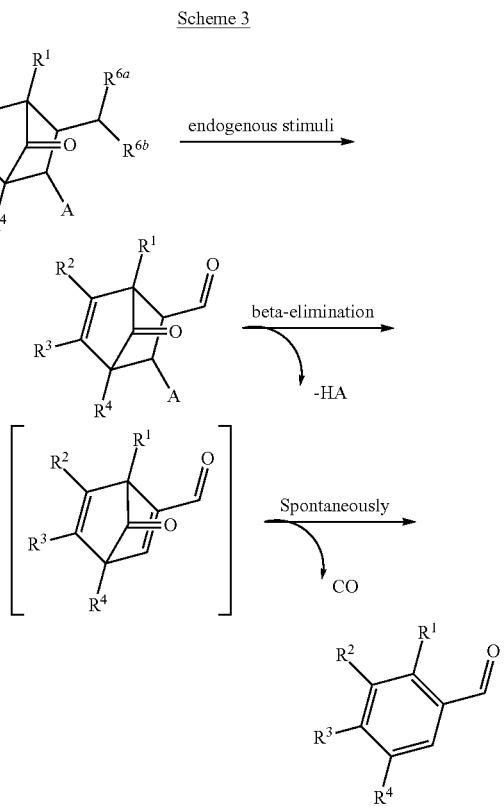

In some embodiments, the aldehyde group is masked by an acetal or thioacetal group to deactivate the beta-elimination for CO release. In some such embodiments, $R^{6a}$ and $R^{6b}$ as shown in Scheme 3 are $OR^{10}$ or $SR^{11}$, wherein $R^{10}$ and $R^{11}$ are optionally substituted $C_{1-6}$ alkyl. In the presence of endogenous stimuli, such as a change in pH or exposure to reactive oxygen species (ROS) and/or enzymes, the acetal or thioacetal is converted to an aldehyde to initiate the intended elimination for CO release. As described above, acetals and thioacetals can be geminal diesters/dithioesters in certain instances. Such compounds can be cleaved by enzymes such as esterases under physiological conditions, triggering the aldehyde formation and leaving group elimination.

V. Pharmaceutical Formulations

In a related aspect, the invention provides pharmaceutical compositions containing a compound (a compound of Formula I, Formula Ia, Formula Ib and/or Formula Ic) of the invention and a pharmaceutically acceptable carrier or excipient, including but not limited to, purified water, buffer, or other pharmaceutically acceptable solvent. The carbon monoxide releasing compounds can also be formulated in a liposome or micelle. The amount of compound to be administered can be readily determined based on the amount of carbon monoxide to be generated.

The compounds can be administered orally, topically, parenterally, by inhalation or spray or rectally in dosage unit formulations. The term "administration by injection" includes intravenous, intramuscular, subcutaneous and parenteral injections, as well as use of infusion techniques. One or more compounds can be present in association with one or more non-toxic pharmaceutically acceptable carriers and if desired other active ingredients.

Parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes. The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride. More details on non-aqueous liquid formulations are disclosed below.

Solutions and dispersions of the carbon monoxide releasing compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Compositions intended for oral use can be prepared according to any suitable method known to the art for the manufacture of pharmaceutical compositions. Suitable oral dosage forms include tablets, capsules, solutions, suspensions, syrups, and lozenges. Such compositions can contain one or more agents selected from diluents, sweetening agents, flavoring agents, coloring agents and preserving agents in order to provide palatable preparations. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium carbonate, calcium sulfate, lactose, sucrose, mannitol, sorbitol, cellulose, microcrystalline cellulose, kaolin, sodium chloride, sodium phosphate, sodium carbonate, dry starch, hydrolyzed starches, pregelatinized starch, silicon dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrating and granulating agents are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross-linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Compositions for oral use can also be formulated as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the carbon monoxide releasing compounds in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents can be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the compounds in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example *arachis* oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Pharmaceutical compositions of the invention can also be in the form of oil-in-water emulsions. The oily phase can be a vegetable oil, for example olive oil or *arachis* oil, or a mineral oil, for example liquid paraffin or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

VI. Methods of Treatment

The compounds (also referred to as carbon monoxide releasing compounds) and methods of the invention have applications in any therapeutic approach in which carbon monoxide requirements are addressed. The requirement may be due to deficiency of carbon monoxide in a subject. The compounds and methods can also be used to treat patients having normal levels of endogenous carbon monoxide but who would benefit from an increase in carbon monoxide. The invention therefore relates to methods for treating and preventing diseases that are mediated at least in part by endogenous carbon monoxide.

Accordingly, another aspect of the invention affords a method of providing carbon monoxide to a subject in need thereof. In certain embodiments, the method includes administering a compound of the invention, or a pharmaceutical composition containing a composition of the invention, to a subject under conditions sufficient to form carbon monoxide. In some embodiments, the method includes administering a compound according to Formula I to the subject. In some embodiments, the carbon monoxide releasing compounds are used for the treatment of a condition selected from a cardiovascular condition, an ophthalmic condition, a neurological condition, a urological condition, diabetes, inflammation, bacterial infection, hypertension, hypothermia, diabetes, asthma, gastric injury, irritable bowel syndrome, kidney dysfunction, sepsis, ischemia, respiratory distress syndrome, autoimmune disorders, thrombosis and cancer. The carbon monoxide releasing compounds can also be used for wound healing, organ preservation, and used to reduce rejection in organ transplantation (e.g., organ protection). In other embodiments, the compounds of the present invention can also be used to prevent, minimize, or reverse toxicity associated with the administration of various therapeutic agents, such as doxorubicin. As such, the compounds of the invention can be administered alone as a monotherapy or in combination with other active agents.

In some embodiments, the carbon monoxide releasing compounds are used for treatment of a cardiovascular condition. In some embodiments, the cardiovascular condition is selected from myocardial infarction, heart failure, heart attack, heart stroke, cardiomyopathy, myocardial fibrosis, pulmonary arterial hypertension (PAH), and angina pectoris.

In some embodiments, the carbon monoxide releasing compounds are used for treatment of cancers. In some embodiments, the cancer is selected from lung, breast, prostate, brain, bone, bladder, cervical, gastric, oral, ovarian, testicular, liver, rectal, retinal, urethral, uterine and vaginal cancer.

The cancer can be a carcinoma, a sarcoma, an adenocarcinoma, a lymphoma, a leukemia, and a solid and lymphoid cancer. Examples of different types of cancer include, but are not limited to, lung cancer (e.g., non-small cell lung cancer or NSCLC), ovarian cancer, prostate cancer, colorectal cancer, liver cancer (e.g., hepatocarcinoma), renal cancer (e.g., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma, head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma.

In some embodiments, the carbon monoxide releasing compounds are used for treatment of inflammatory disorders, including but not limited to, arthritis (e.g., rheumatoid arthritis and collagen-induced arthritis), inflammatory bowel disease (IBD), ulcerative colitis, Crohn's disease, psoriasis, uveitis, mid-ear inflammation, and osteoarthritis. In some embodiments, the compounds are used for treatment of Alzheimer's disease. In some embodiments, the compounds are used for treatment of Parkinson's disease.

The specific dose level selected for any particular patient will depend upon a variety of factors, including the activity of the specific compound employed, the age, body weight, general health, sex, diet, time of administration, route of administration, and rate of excretion, drug combination and the severity of the condition undergoing therapy.

Carbon monoxide releasing compounds can be administered at any suitable dose in the methods of the invention. In general, a carbon monoxide releasing compound is administered at a dose ranging from about 0.1 milligrams to about 1000 milligrams per kilogram of a subject's body weight (i.e., about 0.1-1000 mg/kg). The dose of the carbon monoxide releasing compound can be, for example, about 0.1-1000 mg/kg, or about 1-500 mg/kg, or about 25-250 mg/kg, or about 50-100 mg/kg. The dose of the carbon monoxide releasing compound can be, for example, about 10-20 mg/kg, or 5-25 mg/kg, or 1-50 mg/kg, or 0.1-100 mg/kg. The dose of the compound can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The dose of the carbon monoxide releasing compound can be administered at a dose below about 1, below about 2, below about 3, below about 4, below about 5, below about 10, below about 15, below about 20, below about 25, below about 30, below about 35, below about 40, below about 45, below about 50, below about 55, below about 60, below about 65, below about 70, below about 75, below about 85, below about 90, below about 95, below about 100, below about 150, below about 200, below about 250, below about 300, below about 350, below about 400, below about 450, below about 500, below about 550, below about 600, below about 650, below about 700, below about 750, below about 800, below about 850, below about 900, below about 950, or below about 1000 mg/kg.

In some embodiments, the dose of the compound is sufficient to release carbon monoxide in an amount such that no more than about 20% of the hemoglobin in a blood sample obtained from the subject is present as carboxyhemoglobin (HbCO). In some embodiments, the dose of the compound is sufficient to release carbon monoxide in an amount such that no more than about 15% of the hemoglobin in a blood sample obtained from the subject is present as HbCO. In some embodiments, the dose of the compound is sufficient to release carbon monoxide in an amount such that the amount of HbCO in a blood sample taken from the subject ranges from about 5% to about 15% (e.g., from about 5-12%) based on the total amount of hemoglobin in the sample. Sampling and HbCO quantification can be conducted over periods of time ranging from minutes to hours, or longer, following compound administration, and HbCO concentrations can be determined using known quantitative methods and devices (as described, for example, in U.S. Pat. Nos. 6,397,093; 5,491,341; and 4,997,769). Dosage can be adjusted such that the peak HbCO concentration does not exceed a certain level (e.g., 15%).

The dosages can be varied depending upon the needs of the patient, the particular formulation being administered, and other factors. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to address the carbon monoxide requirement.

Administration of a compound of the present invention can be conducted for a period of time which will vary depending upon the nature of the particular carbon monoxide requirement, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the carbon monoxide requirement. The dosage of the carbon monoxide releasing compound can either be increased in the event the patient does not respond significantly to a particular dosage level, or the dose can be decreased if an alleviation of the symptoms of the carbon monoxide requirement is observed, or if the carbon monoxide requirement has been ablated, or if unacceptable side effects are seen with a particular dosage.

A therapeutically effective amount of carbon monoxide releasing compound can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the carbon monoxide requirement decreases, the dosage may be maintained or kept at lower than maximum amount. If the requirement increases, the first dosage regimen can be resumed until an improvement is seen, and the second dosing regimen can be implemented again. This cycle can be repeated multiple times as necessary.

VII. Examples

Example 1. Synthesis of pH-Sensitive CO Releasing Compounds pH-sensitive CO prodrugs 1-6 (Scheme 4) were designed and synthesized. An aldehyde group was incorporated into the compounds for its strong electron withdrawing ability. Despite being very good leaving groups, halides were avoided to minimize their alkylation capacity and issues related to hydrogen halides. As a result, substituted phenols were chosen to achieve a balance between leaving ability and reactivity.

As shown in Scheme 4, CO prodrugs 1-6 were readily synthesized in 4 steps. Specifically, compounds 1.4-6.4, which were obtained according to a reported procedure, were reduced using DIBAL to yield the corresponding alcohol 1.3-6.3. The hydroxyl group in compounds 1.3-6.3 was protected with MOMCl to form 1.2-6.2 before the DA reaction. Compounds 1.1-6.1 were successfully obtained primarily as an endo product, as confirmed by heteronuclear multiple-bond correlation spectroscopy (O=C—C—C-Ha), after the DA reaction and deprotection of MOM group. The final CO prodrugs 1-6 were obtained upon oxidation of the hydroxyl group in compounds 1.1-6.1 using PCC in reflux $CH_2Cl_2$.

No beta-elimination was observed in the process, indicating the desirable stability of CO prodrugs 1-5 in organic solvent. The stability of compound 1 in organic solvents (e.g., $CDCl_3$) at 37° C. was also tested, and no beta-elimination products were observed even after one week of incubation.

All reagents and solvents were of reagent grade. Column chromatography was carried out using flash silica gel (Sorbent 230-400 mesh) and P-2 Gel (Bio-Gel, particle size range 45-90 μm). TLC analyses were conducted on silica gel plates (Sorbent Silica G UV254). NMR spectra were recorded at 400 MHz for $^1H$ and 100 MHz for $^{13}C$ on an Avance Bruker instrument. Chemical shifts (δ values) and coupling constants (J values) are given in ppm and hertz, respectively, using the respective solvent ($^1H$ NMR, $^{13}C$ NMR) or TMS as the internal reference.

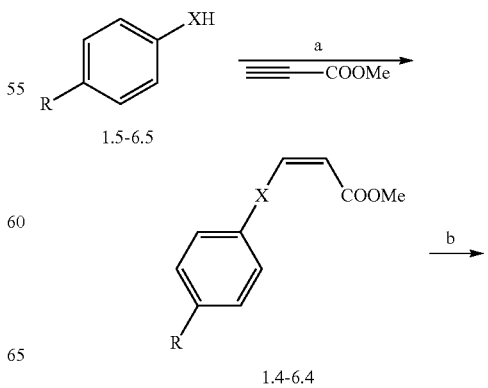

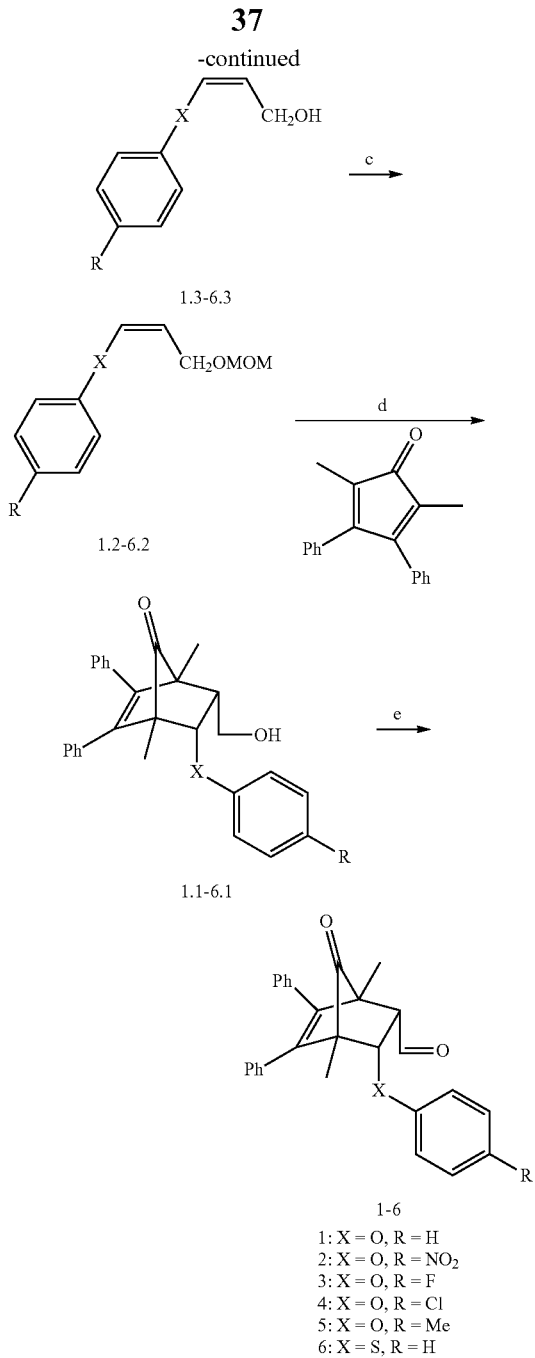

Reagents and conditions: a) K₂CO₃, H₂O, r.t., overnight, 40-92%; b) DIBAL, CH₂Cl₂, -78° C., 1-2 h, 75%-80%; c) DIPEA, MOMCl, CH₂Cl₂, r.t., 3 h, 85-90%; d) xylene, 170° C., 12 h; then HCl, MeOH, reflux, 1 h, 50-60%; e) CH₂Cl₂, PCC, reflux, 30 min-1 h, 60-73%.

General procedure for the synthesis of compounds 1.4-6.4. To a solution of substituted phenol/thiophenol (1.5-6.5; 1 equiv.) and K₂CO₃ (1.1 equiv.) in water (30 mL), was added methyl propionate (1 equiv.) dropwise at room temperature. The resulting mixture was stirred at room temperature overnight, and then extracted with ethyl acetate (3×40 mL). The combined organic layers was washed with 5% of NaOH and brine successively, and dried over anhydrous Na₂SO₄. After filtration and concentration, the obtained residue was purified on a silica gel column to afford the title compounds.

1.4 (colorless oil, yield: 90%): $^1$H NMR (CDCl₃): δ 7.31 (t, J=8.0 Hz, 2H), 7.10 (t, J=8.0 Hz, 1H), 7.06 (d, J=8.0 Hz, 1H), 6.98 (d, J=6.9 Hz, 1H), 5.20 (d, J=6.9 Hz, 1H), 3.80 (s, 3H).

2.4 (white solid, without purification, yield: 40%): $^1$H NMR (CDCl₃) δ 8.31 (d, J=8.0 Hz, 2H), 7.25 (d, J=8.0 Hz, 2H), 6.93 (d, J=6.9 Hz, 1H), 5.39 (d, J=6.9 Hz, 1H), 3.79 (s, 3H). $^{13}$C NMR (CDCl₃): δ 164.4, 160.9, 150.9, 144.3, 126.0, 117.5, 102.9, 51.5. HRMS (ESI)$^+$ calculated for C₁₀H₉NO₅Na [M+Na]$^+$: m/z 246.0378, found 246.0367.

3.4 (colorless oil, yield: 92%): $^1$H NMR (CDCl₃): δ 7.12-7.00 (m, 4H), 6.82 (d, J=6.9 Hz, 1H), 5.19 (d, J=7.0 Hz, 1H), 3.77 (s, 3H). $^{13}$C NMR (CDCl₃): δ 165.4, 154.6, 119.2, 119.1, 116.6, 116.3, 116.2, 116.2, 115.8, 115.6, 99.6, 51.3. HRMS (ESI)$^+$ calculated for C₁₀H₉FO₃Na [M+Na]$^+$: m/z 219.0433, found 219.0430.

4.4 (colorless oil, yield: 80%): $^1$H NMR (CDCl₃): δ 7.33 (d, J=8.8 Hz, 2H), 7.06 (d, J=8.8 Hz, 2H), 6.82 (d, J=6.8 Hz, 1H), 5.21 (d, J=6.8 Hz, 1H), 3.76 (s, 3H). $^{13}$C NMR (CDCl₃): δ 164.9, 155.6, 153.6, 130.0, 129.9, 119.0, 100.4, 51.3. HRMS (ESI)$^+$ calculated for C₁₀H₉C₁₀O₃Na [M+Na]$^+$: m/z 235.0138, found 235.0128.

5.4 (colorless oil, yield: 85%): $^1$H NMR (CDCl₃) δ 7.04-7.02 (m, 2H), 6.89-6.86 (m, 2H), 6.75 (d, J=7.2 Hz, 1H), 5.03 (d, J=6.8 Hz, 1H), 3.62 (s, 3H), 2.21 (s, 3H). $^{13}$C NMR (CDCl₃) δ 164.8, 154.9, 154.5, 134.0, 130.0, 117.1, 98.7, 50.7, 20.3. HRMS (ESI)$^+$ calculated for C₁₁₁H₁₂O₃Na [M+Na]$^+$: m/z 215.0684, found 215.0679.

6.4 (colorless oil, yield: 90%): δ 7.54-7.46 (m, 2H), 7.43-7.34 (m, 3H), 7.31 (d, J=10.0 Hz, 1H), 5.95 (d, J=10.0 Hz, 1H), 3.81 (s, 3H).

General procedure for the synthesis of compounds 1.3-6.3. To a solution of 1.4-6.4 (1 equiv.) in dry CH₂Cl₂ (50 mL) was added DIBAL (2.8 equiv.) dropwise under N₂ at −78° C. The resulting reaction mixture was stirred for another 1 h at −78° C. before being was poured into saturated Rochelle salt solution (50 mL) carefully. The resulting mixture was stirred for another 30 min at room temperature. The organic layer was separated, and the aqueous layer was extracted with CH₂Cl₂ (2×40 mL). The combined organic layer was washed with brine, and dried over anhydrous Na₂SO₄. After filtration and concentration, the obtained residue was purified on a silica gel column to afford the title compound.

1.3 (colorless oil, yield: 75%). $^1$H NMR (CDCl₃): δ 7.35 (t, J=7.9 Hz, 2H), 7.10 (t, J=7.3 Hz, 1H), 7.03 (d, J=8.0 Hz, 2H), 6.51 (d, J=6.1 Hz, 1H), 5.11 (dd, J=13.2, 6.6 Hz, 1H), 4.41 (dd, J=6.8, 1.0 Hz, 2H). $^{13}$C NMR (CDCl₃): δ 157.1, 142.5, 129.7, 123.2, 116.5, 111.1, 56.3. HRMS (ESI)$^+$ calculated for C₁₀H₉O₂Na [M+Na]$^+$: m/z 173.0578, found 173.0571.

2.3 (colorless oil, yield: 78%): $^1$H NMR (CDCl₃): δ 8.22 (d, J=8.0 Hz, 2H), 7.09 (d, J=8.0 Hz, 2H), 6.53 (d, J=6.1 Hz, 1H), 5.29 (q, J=8.0 Hz, 1H), 4.40 (t, J=5.5 Hz, 2H), 1.94 (t, J=5.4 Hz, 1H). $^{13}$C NMR (CDCl₃): δ 161.5, 143.04, 140.1, 126.0, 116.1, 114.5, 56.0. HRMS (ESI)$^+$ calculated for C₉H9NO₄Na [M+Na]$^+$: m/z 218.0419, found 218.0429.

3.3 (colorless oil, yield: 80%): $^1$H NMR (CDCl₃): δ 7.07-6.84 (m, 4H), 6.39 (d, J=6.1 Hz, 1H), 5.07 (q, J=6.8 Hz, 1H), 4.37 (t, J=5.6 Hz, 2H), 2.31 (s, 1H). $^{13}$C NMR (CDCl₃) δ 159.9, 157.5, 153.2, 142.7, 117.9, 117.8, 116.3, 116.0, 111.1, 56.0. HRMS (ESI)$^+$ calculated for C₉H₉FO₂Na [M+Na]$^+$: m/z 191.0484, found 191.0491.

4.3 (colorless oil, yield: 76%): $^1$H NMR (CDCl₃): δ 7.28 (t, J=9.2 Hz, 2H), 6.95 (d, J=9.2 Hz, 2H), 6.43 (d, J=6.0 Hz, 1H), 5.12 (q, J=6.8 Hz, 1H), 4.38 (t, J=5.6 Hz, 2H), 1.81 (t, J=5.6 Hz, 1H). $^{13}$C NMR (CDCl₃): δ 155.6, 142.1, 129.7, 128.2, 117.8, 111.7, 56.2. HRMS (ESI)$^+$ calculated for C$_9$H$_9$ClO$_2$Na [M+Na]$^+$: m/z 207.0189, found 207.0195.

5.3 (colorless oil, yield: 80%): $^1$H NMR (CDCl$_3$) δ 7.12-7.10 (m, 2H), 6.91-6.89 (m, 2H), 6.42 (d, 1H), 5.09-5.04 (m, 1H), 4.42-4.40 (m, 2H), 3.33-3.00 (brs, 1H), 2.32 (s, 3H). $^{13}$C NMR (CDCl$_3$) δ 155.0, 142.4, 132.4, 130.0, 116.3, 110.6, 55.8, 20.5. HRMS (ESI)$^+$ calculated for C$_{10}$H$_{12}$O$_2$Na [M+Na]$^+$: m/z 187.0735, found 187.0733.

6.3 (colorless oil, yield: 80%): $^1$H NMR (CDCl$_3$): δ 7.41-7.27 (m, 5H), 6.38 (d, J=9.5 Hz, 1H), 6.00 (m, 1H), 4.39 (t, J=5.4 Hz, 2H), 1.87 (t, J=5.6 Hz, 1H).

General procedure for the synthesis of compounds 1.2-6.2. To a solution of 1.3-6.3 (1 equiv.) and DIPEA (1.6 equiv.) in dry CH$_2$Cl$_2$ (30 mL) was added MOMCl (1.5 equiv.) dropwise at room temperature, and the resulting solution was stirred for another 3 h at room temperature. Then the reaction mixture was washed with water and brine, and was dried over anhydrous Na$_2$SO$_4$. After filtration and concentration, the obtained residue was purified on a silica gel column to afford the title compound as colorless oil.

1.2 (colorless oil, yield: 90%): $^1$H NMR (CDCl$_3$): δ 7.38-7.30 (m, 2H), 7.10 (t, J=8.0 Hz, 1H), 7.02 (d, J=8.0 Hz, 2H), 6.55 (dt, J=6.1, 1.3 Hz, 1H), 5.05 (dd, J=13.2, 6.9 Hz, 1H), 4.71 (s, 2H), 4.34 (dd, J=7.0, 1.1 Hz, 2H), 3.42 (s, 3H). $^{13}$C NMR (CDCl$_3$): δ 157.2, 143.1, 129.7, 123.1, 116.6, 108.2, 95.9, 60.5, 55.3.

2.2 (colorless oil, yield: 85%): $^1$H NMR (CDCl$_3$): δ 8.24 (d, J=8.0 Hz, 2H), 7.10 (d, J=8.0 Hz, 2H), 6.58 (dd, J=6.1, 0.9 Hz, 1H), 5.26 (q, J=6.3 Hz, 1H), 4.67 (s, 2H), 4.32 (d, J=6.8 Hz, 2H), 3.39 (d, J=2.0 Hz, 3H). $^{13}$C NMR (CDCl$_3$): δ 161.5, 143.1, 140.7, 126.0, 116.2, 112.0, 96.0, 60.2, 55.3. HRMS (ESI)$^+$ calculated for C$_{11}$H$_{13}$NO$_5$Na [M+Na]$^+$: m/z 262.0691, found 262.0701.

3.2 (colorless oil, yield: 87%): $^1$H NMR (CDCl$_3$): δ 7.08-6.87 (m, 4H), 6.45 (dt, J=6.4, 1.2 Hz, 1H), 5.08-4.97 (m, 1H), 4.69 (s, 2H), 4.31 (dd, J=7.2, 1.2 Hz, 2H), 3.40 (s, 3H). $^{13}$C NMR (CDCl$_3$): δ 159.8, 157.5, 153.3, 143.4, 117.9, 117.8, 116.2, 116.0, 108.3, 95.9, 60.3, 55.2. HRMS (ESI)$^+$ calculated for C$_{11}$H$_{13}$FO$_3$Na [M+Na]$^+$: m/z 235.0746, found 235.0747.

4.2 (colorless oil, yield: 90%): $^1$H NMR (CDCl$_3$): δ 7.28 (d, J=6.8 Hz, 2H), 6.95 (d, J=6.8 Hz, 2H), 6.47 (d, J=6.4 Hz, 1H), 5.08 (q, J=7.2 Hz, 1H), 4.69 (s, 2H), 4.31 (d, J=6.8 Hz, 2H), 3.40 (s, 3H). $^{13}$C NMR (CDCl$_3$): δ 155.7, 142.7, 129.6, 128.1, 117.8, 109.0, 95.9, 60.3, 55.3. HRMS (ESI)$^+$ calculated for C$_{11}$H$_{13}$ClO$_3$Na [M+Na]$^+$: m/z 251.0451, found 251.0461.

5.2 (colorless oil, yield: 88%): $^1$H NMR (CDCl$_3$) δ 7.11-7.10 (m, 2H), 6.91-6.89 (m, 2H), 6.49 (dt, J=6.4, 1.2 Hz, 1H), 5.02-4.97 (m, 1H), 4.69 (s, 2H), 4.34-4.32 (m, 2H), 3.40 (s, 3H), 2.31 (s, 3H). $^{13}$C NMR (CDCl$_3$) δ 155.1, 143.5, 132.4, 130.0, 116.4, 107.5, 95.8, 60.4, 55.1, 20.5. HRMS (ESI)$^+$ calculated for C$_{12}$H$_{16}$O$_3$Na [M+Na]$^+$: m/z 231.0997, found 231.1001.

6.2 (colorless oil, yield: 90%): $^1$H NMR (CDCl$_3$) δ 7.39 (m, 4H), 6.45 (d, J=9.5 Hz, 1H), 5.98-5.93 (m, 1H), 4.71 (s, 2H), 4.31 (dd, J=6.3, 1.2 Hz, 1H), 3.43 (s, 3H).

General procedure for the synthesis of compounds 1.1-6.1. A solution of 1.2-6.2 (6 equiv.) and dienone compound 3 (1 equiv.) in xylene (2 mL) was heated to 170-180° C. in a sealed tube for 12 h. Then the reaction mixture was concentrated under vacuum, and the obtained residue was purified on a silica gel column (hexane/ether=10:1) to afford a yellowish oil, which was dissolved in MeOH (5 mL) containing 1 mL of HCl aqueous solution (37%). The resulting solution was heated under reflux for 1 h. Then the reaction mixture was concentrated, and the obtained residue was taken up with ethyl acetate (40 mL). The organic layer was then washed with brine, and was dried over anhydrous Na$_2$SO$_4$. After filtration and concentration, the obtained residue was purified on a silica gel column to afford the title compound.

1.1 (white solid, yield: 50%): $^1$H NMR (CDCl$_3$): δ 7.38-7.31 (m, 2H), 7.25-7.21 (m, 8H), 7.15-7.12 (m, 2H), 7.04-7.01 (m, 3H), 5.08 (d, J=8.5 Hz, 1H), 4.01-3.96 (m, 1H), 3.88-3.82 (m, 1H), 2.78-2.66 (m, 1H), 1.47 (s, 3H), 1.32 (s, 3H). $^{13}$C NMR (CDCl$_3$): δ 203.5, 159.1, 141.4, 134.8, 130.0, 129.9, 129.7, 128.2, 127.9, 127.2, 127.2, 121.9, 115.6, 81.9, 60.0, 57.1, 52.7, 12.1, 11.0. HRMS (ESI)$^+$ calculated for C$_{28}$H$_{26}$O$_3$Na [M+Na]$^+$: m/z 433.1780, found 433.1767.

2.1 (yellowish solid, yield: 51%): $^1$H NMR (CDCl$_3$): δ 8.23 (d, J=8.0 Hz, 2H), 7.28-7.22 (m, 6H), 7.19-7.05 (m, 6H), 5.17 (d, J=8.0 Hz, 1H), 3.95-3.82 (m, 2H), 2.80 (q, J=8.0 Hz, 1H), 1.48 (s, 3H), 1.34 (s, 3H). $^{13}$C NMR (CDCl$_3$): δ 202.5, 164.1, 142.1, 141.8, 141.0, 134.6, 134.5, 129.9, 129.6, 128.3, 128.0, 127.5, 127.4, 126.1, 115.5, 82.7, 59.9, 59.6, 57.2, 52.3, 12.1, 11.0. HRMS (ESI)$^+$ calculated for C$_{28}$H$_{25}$NO$_5$Na [M+Na]$^+$: m/z 478.1630, found 478.1630.

3.1 (white solid, yield: 60%): $^1$H NMR (CDCl$_3$): δ 7.27-7.16 (m, 8H), 7.16-7.09 (m, 2H), 7.02-6.91 (m, 4H), 4.98 (d, J=8.4 Hz, 1H), 4.02-3.97 (m, 1H), 3.92-3.79 (m, 1H), 2.77-2.71 (m, 1H), 1.45 (s, 3H), 1.31 (s, 3H). $^{13}$C NMR (CDCl$_3$): δ 203.3, 159.0, 156.6, 155.3, 155.3, 141.5, 141.1, 134.9, 134.7, 130.0, 129.7, 128.2, 127.9, 127.3, 127.2, 117.0, 116.9, 116.4, 116.1, 83.2, 60.0, 60.0, 57.0, 52.6, 12.0, 11.1. HRMS (ESI)$^+$ calculated for C$_{28}$H$_{25}$FO$_3$Na [M+Na]$^+$: m/z 451.1685, found 451.1695.

4.1 (white solid, yield: 55%): $^1$H NMR (CDCl$_3$): δ 7.28-7.20 (m, 8H), 7.20-7.15 (m, 2H), 7.15-7.10 (m, 2H), 6.98-6.87 (m, 2H), 5.01 (d, J=8.4 Hz, 1H), 3.99-3.93 (m, 1H), 3.89-3.83 (m, 1H), 2.77-2.71 (m, 1H), 1.46 (s, 3H), 1.31 (s, 3H). $^{13}$C NMR (CDCl$_3$): δ 203.2, 157.7, 141.5, 141.2, 134.8, 134.7, 130.8, 130.0, 129.7, 129.7, 128.2, 127.9, 127.3, 127.3, 126.8, 119.4, 117.0, 82.6, 60.0, 59.9, 57.1, 52.5, 12.1, 11.0. HRMS (ESI) calculated for C$_{28}$H$_{25}$ClO$_3$Na [M+Na]$^+$: m/z 467.1390, found 467.1374.

5.1 (white solid, yield: 54%): $^1$H NMR (CDCl$_3$) δ 7.26-7.19 (m, 8H), 7.13-7.09 (m, 4H), 6.91 (m, 2H), 5.02 (d, J=8.0 Hz, 1H), 4.01-3.79 (m, 2H), 2.73-2.71 (m, 1H), 2.30 (s, 3H), 2.28 (s, 1H), 1.44 (s, 3H), 1.30 (s, 3H). $^{13}$C NMR (CDCl$_3$) δ 203.8, 157.1, 141.5, 141.4, 135.0, 131.4, 130.4, 130.1, 129.8, 128.2, 128.0, 127.3, 127.2, 115.5, 82.2, 60.1, 57.1, 52.8, 20.6, 12.2, 11.1.

6.1 (colorless oil, yield: 55%): $^1$H NMR (CDCl$_3$) δ 7.44-7.42 (m, 2H), 7.34-7.31 (m, 2H), 7.27-7.20 (m, 9H), 7.22 (m, 2H), 7.10-7.07 (m, 2H), 4.08-4.02 (m, 1H), 3.95-3.89 (m, 2H), 2.84-2.79 (m, 1H), 2.21 (dd, J=8.6, 4.4 Hz, 1H), 1.43 (s, 3H), 1.37 (s, 3H). $^{13}$C NMR (CDCl$_3$): δ 203.2, 142.8, 142.4, 136.6, 134.7, 134.6, 131.7, 130.4, 130.0, 129.7, 129.5, 129.4, 129.3, 129.2, 128.2, 127.9, 127.3, 127.3, 127.0, 62.3, 59.2, 57.0, 56.6, 50.8, 11.8, 11.5.

General procedure for the synthesis of 1-6. A mixture of 1.1-6.1 (1 equiv.) and PCC (4 equiv.) in CH$_2$Cl$_2$ (20 mL) was heated under reflux for 30 min. Then the reaction mixture was filtered through a short (Ø=2 cm, L=2 cm) silica gel column under reduced pressure, and the obtained filtrate was dried directly to afford the title compound as white solid.

1 (white solid, yield: 60%): $^1$H NMR (CDCl$_3$): δ 9.63 (d, J=4.8 Hz, 1H), 7.34-7.27 (m, 5H), 7.24-7.21 (m, 5H), 7.08-6.99 (m, 3H), 6.98-6.89 (m, 2H), 5.13 (d, J=8.1 Hz, 1H), 3.14 (dd, J=8.1, 4.8 Hz, 1H), 1.43 (s, 3H), 1.41 (s, 3H). $^{13}$C NMR (CDCl$_3$): δ 200.3, 200.1, 157.2, 142.4, 140.1, 134.4, 134.1, 130.0, 129.7, 128.3, 128.0, 127.6, 127.6, 122.4, 115.4, 82.1, 60.9, 59.8, 58.1, 11.5, 10.5. HRMS (ESI)$^+$ calculated for $C_{28}H_{24}O_3Na$ [M+Na]$^+$: m/z 431.1623, found 431.1620.

2 (white solid, yield: 65%): $^1$H NMR (CDCl$_3$): δ 9.62 (d, J=4.8 Hz, 1H), 8.24 (d, J=8.0 Hz, 2H), 7.32-7.28 (m, 4H), 7.27-7.18 (m, 4H), 7.10-6.89 (m, 4H), 5.23 (d, J=8.0 Hz, 1H), 3.23 (dd, J=8.0, 4.8 Hz, 1H), 1.45 (s, 3H), 1.44 (s, 3H). $^{13}$C NMR (CDCl$_3$): δ 199.1, 199.1, 162.0, 142.7, 141.8, 140.7, 136.1, 134.0, 133.7, 131.3, 129.8, 129.7, 128.5, 128.2, 127.9, 126.2, 115.4, 83.1, 60.8, 59.9, 58.0, 11.5, 10.6. HRMS (ESI) calculated for $C_{28}H_{23}NO_5Na$ [M+Na]$^+$: m/z 476.1474, found 476.1479.

3 (white solid, yield: 73%): $^1$H NMR (CDCl$_3$): δ 9.66 (d, J=5.2 Hz, 1H), 7.28-7.19 (m, 7H), 7.04-6.98 (m, 5H), 6.88 (dd, J=9.2, 4.2 Hz, 2H), 5.06 (d, J=8.0 Hz, 1H), 3.14 (dd, J=8.0, 4.8 Hz, 1H), 1.43 (s, 3H), 1.42 (s, 3H). $^{13}$C NMR (CDCl$_3$): δ 200.1, 200.0, 159.3, 156.9, 153.5, 142.2, 140.3, 134.3, 134.0, 129.9, 129.7, 128.4, 128.1, 127.7, 127.6, 116.7, 116.7, 116.6, 116.3, 83.3, 61.0, 59.9, 58.0, 11.5, 10.6. HRMS (ESI) calculated for $C_{28}H_{23}FO_3Na$ [M+Na]$^+$: m/z 449.1529, found 449.1529.

4 (white solid, yield: 70%): $^1$H NMR (CDCl$_3$): δ 9.64 (d, J=4.8 Hz, 1H), 7.30-7.20 (m, 10H), 7.04-7.02 (m, 2H), 6.88 (d, J=8.8 Hz, 2H), 5.09 (d, J=8.0 Hz, 1H), 3.15 (dd, J=8.4, 4.8 Hz, 1H), 1.43 (s, 3H), 1.42 (s, 3H). $^{13}$C NMR (CDCl$_3$): δ 199.9, 199.9, 155.9, 142.2, 140.3, 134.3, 134.0, 129.9, 129.9, 129.7, 128.4, 128.1, 127.69, 127.7, 127.5, 116.7, 82.8, 60.9, 59.8, 58.0, 11.5, 10.6. HRMS (ESI)$^+$ calculated for $C_{28}H_{23}Cl_{10}O_3Na$ [M+Na]$^+$: m/z 465.1233, found 465.1248.

5 (white solid, yield: 63%): $^1$H NMR (CDCl$_3$): δ 9.63 (d, J=4.9 Hz, 1H), 7.28-7.21 (m, 8H), 7.11 (d, J=8.2 Hz, 2H), 7.04-7.01 (m, 2H), 6.84 (d, J=8.2 Hz, 2H), 5.09 (d, J=8.4 Hz, 1H), 3.13 (dd, J=8.1, 4.9 Hz, 1H), 2.31 (s, 3H), 1.43 (s, 3H), 1.41 (s, 3H). $^{13}$C NMR (CDCl$_3$): δ 200.4, 200.2, 155.1, 142.4, 140.0, 134.4, 134.1, 131.8, 130.4, 130.0, 129.7, 128.3, 128.0, 127.6, 127.5, 115.2, 82.3, 60.9, 59.8, 58.1, 20.5, 11.5, 10.5. HRMS (ESI)$^+$ calculated for $C_{29}H_{26}O_3Na$ [M+Na]$^+$: m/z 445.1780, found 445.1788.

6 (white solid, yield: 68%): $^1$H NMR (CDCl$_3$): δ 9.95 (d, J=5.0 Hz, 1H), 7.34-7.21 (m, 13H), 7.03-7.01 (m, 2H), 4.01 (d, J=9.6 Hz, 1H), 3.15 (dd, J=9.6, 5.1 Hz, 1H), 1.49 (s, 3H), 1.38 (s, 3H). $^{13}$C NMR (CDCl$_3$): δ 201.4, 200.1, 142.9, 141.6, 134.95, 134.1, 130.6, 130.3, 129.8, 129.4, 128.3, 128.1, 127.7, 127.6, 127.4, 58.5, 58.5, 57.2, 55.6, 11.5, 11.0.

Example 2. Preparation of pH-Insensitive Control Compounds

Scheme 5

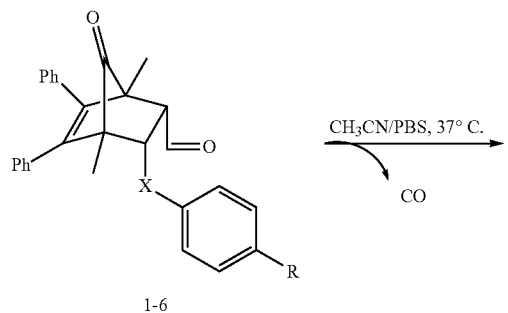

1-6

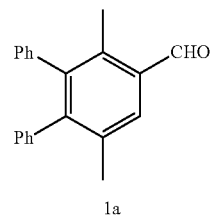

1a

A solution of 1, 2, 3, 4, 5, or 6 (10 mg) in CH$_3$CN/PBS (10 mL, 2:1) was incubated at 37° C. overnight. Then the reaction mixture was extracted with ethyl acetate (3×30 mL). The combine organic layer was washed with 5% NaOH and brine, and was dried over anhydrous Na$_2$SO$_4$. After filtration and concentration, the obtained residue was purified on a silica gel column to afford compound 1a as a white solid (yield: 90%). $^1$H NMR (CDCl$_3$): δ 10.42 (s, 1H), 7.79 (s, 1H), 7.19-7.11 (m, 6H), 6.95-6.92 (m, 4H), 2.40 (s, 3H), 2.16 (s, 3H). $^{13}$C NMR (CDCl$_3$): δ 192.9, 147.3, 143.5, 139.9, 139.6, 136.3, 134.3, 133.3, 131.8, 130.1, 129.2, 127.7, 127.6, 126.4, 126.3, 20.7, 16.3. HRMS (ESI)$^+$ calculated for $C_{21}H_{18}ONa$ [M+Na]$^+$: m/z 309.1255, found 309.1243.

Scheme 6

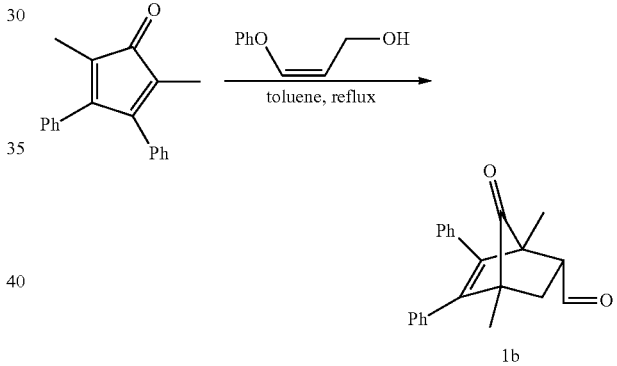

1b

A solution of 2,5-dimethyl-3,4-diphenylcyclopenta-2,4-dien-1-one and 3-phenoxyprop-2-en-1-ol in toluene was heated under reflux for 2 h. Then the reaction mixture was dried directly under vacuum, and the obtained residue was purified on a silica gel column to afford compound 1b as a white solid. $^1$H NMR (CDCl$_3$) δ 9.78 (d, J=1.7 Hz, 1H), 7.27-7.14 (m, 6H), 7.11-6.97 (m, 2H), 6.94-6.79 (m, 2H), 3.05-3.01 (m, 1H), 2.47 (dd, J=12.5, 5.1 Hz, 1H), 1.99 (dd, J=12.5, 9.3 Hz, 1H), 1.57 (s, 3H), 1.33 (s, 3H). $^{13}$C NMR (CDCl$_3$) δ 204.0, 200.8, 144.7, 139.2, 133.9, 133.8, 129.8, 129.0, 128.2, 128.1, 127.5, 127.4, 100.0, 55.8, 54.8, 52.8, 31.7, 12.1, 11.8. HRMS (ESI)$^+$ calculated for $C_{22}H_{20}O_2Na$ [M+Na]$^+$: m/z 339.1361, found 339.1375.

Example 3. Synthesis of pH-Sensitive CO Releasing Compounds

CO prodrugs with the leaving group being a phenylsulfonyl group were synthesized according to Scheme 7. Regents and conditions: a) H$_3$BO$_3$, NBu$_4$HSO$_4$, THF/H$_2$O, r.t.; b) DIBAL, CH$_2$Cl$_2$, −78° C.; c) Dess-Martin periodinane (DMP), CH$_2$Cl$_2$, 0° C.; d) toluene, reflux.

43

Scheme 7

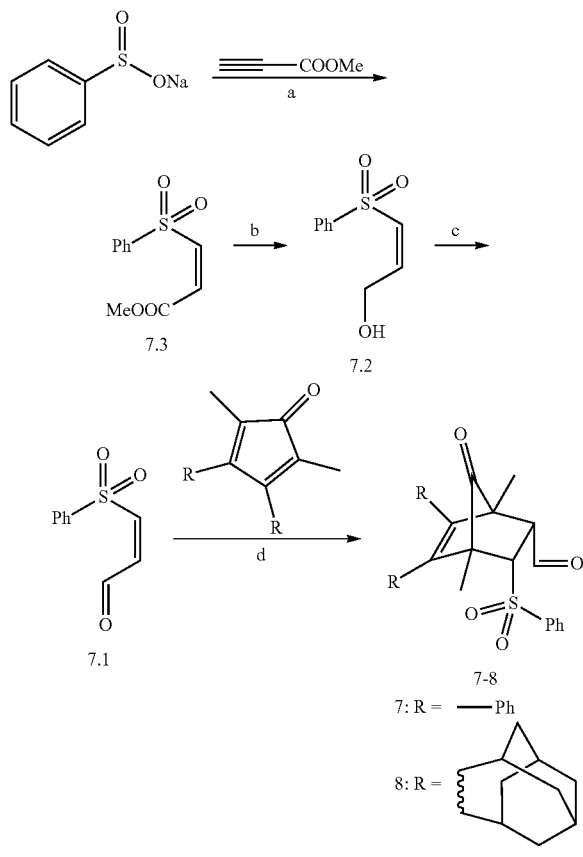

Preparation of compound 7.3. A solution of sodium salt of benzenesulfonic acid (4.56 g, 27.8 mmol), $H_3BO_3$ (2.58 g, 41.7 mmol), $NBu_4HSO_4$ (1.4 g, 4.2 mmol) and methyl propiolate (2.45 g, 29.2 mmol) in $THF/H_2O$ (50/20 mL) was stirred at room temperature for 48 h. Then the reaction mixture was extracted with ethyl acetate (3×40 mL), and the combined organic layer was washed with water and brine successively, and was dried over anhydrous $Na_2SO_4$. After filtration and concentration, the obtained residue was purified on a silica gel column to afford the final product as a colorless oil, which was solidified after overnight at room temperature (2.5 g, yield: 40%). $^1H$ NMR ($CDCl_3$) δ 8.02 (d, J=7.9 Hz, 2H), 7.69 (t, J=7.5 Hz, 1H), 7.60 (t, J=7.5 Hz, 2H), 6.56 (q, J=11.3 Hz, 2H), 3.93 (s, 3H).

Preparation of compound 7.2. Compound 7.2 was obtained as a colorless oil in 60% yield according to the general procedure used to make 1.3-6.3. $^1H$ NMR ($CDCl_3$) δ 8.03-7.81 (m, 2H), 7.65 (d, J=7.5 Hz, 1H), 7.58 (t, J=7.6 Hz, 2H), 6.53-6.39 (m, 1H), 6.29 (dt, J=11.5, 2.0 Hz, 1H), 4.77 (dd, J=5.5, 2.0 Hz, 2H).

Preparation of compound 7.1. To a solution of compound 7.2 (200 mg, 1.01 mmol) in $CH_2Cl_2$ (10 mL) was added DMP portion-wise (642 mg, 1.52 mmol) at 0° C., and the resulting mixture was stirred at 0° C. for another 10 min, and was then filtered through a short length (2 cm) of silica gel column. The filtrate was washed with $NaHCO_3$ solution, and was dried over anhydrous $Na_2SO_4$. After filtration and concentration, the obtained residue was used for the next step without further purification (148 mg, yield: 75%). $^1H$ NMR ($CDCl_3$) δ 10.80 (d, J=6.9 Hz, 1H), 8.00-7.90 (m, 2H), 7.75-7.67 (m, 1H), 7.61 (t, J=7.7 Hz, 2H), 7.04 (d, J=11.6 Hz, 1H), 6.30 (dd, J=11.5, 6.9 Hz, 1H).

General procedure for the synthesis of 7 and 8. A solution of compound 7.1 (300 mg, 1.53 mmol) and dienone (2,5-dimethyl-3,4-diphenylcyclopenta-2,4-dien-1-one or (4r,6R,8S)-1,3-dimethyl-5,6,7,8,9,10-hexahydro-4,8:6,10-dimethanocyclopenta[9]annulen-2(4H)-one; 0.77 mmol) in toluene was heated under reflux for 3 h. Then the reaction mixture was dried directly, and the obtained residue was purified on a silica gel column to afford the final compound as a white solid.

7 (yield: 70%) $^1H$ NMR ($CDCl_3$) δ 10.13 (d, J=5.3 Hz, 1H), 7.77-7.72 (m, 2H), 7.72-7.65 (m, 1H), 7.55 (t, J=7.8 Hz, 2H), 7.40-7.37 (m, 2H), 7.28-7.21 (m, 6H), 7.10-7.04 (m, 2H), 4.15 (d, J=10.3 Hz, 1H), 3.03 (dd, J=10.3, 5.3 Hz, 1H), 1.44 (s, 3H), 1.34 (s, 3H).

8 (yield: 75%): $^1H$ NMR ($CDCl_3$) δ 10.13 (d, J=5.3 Hz, 1H), 7.74 (dd, J=8.4, 1.2 Hz, 2H), 7.71-7.65 (m, 1H), 7.54 (t, J=7.8 Hz, 3H), 7.40-7.38 (m, 2H), 7.27-7.22 (m, 6H), 7.11-7.03 (m, 2H), 4.16 (d, J=10.3 Hz, 1H), 3.03 (dd, J=10.3, 5.3 Hz, 1H), 1.44 (s, 3H), 1.34 (s, 3H).

Example 4. Synthesis of an Oxidation-Sensitive CO Releasing Compound

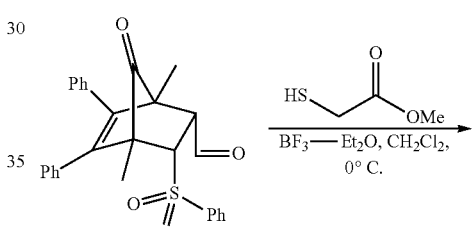

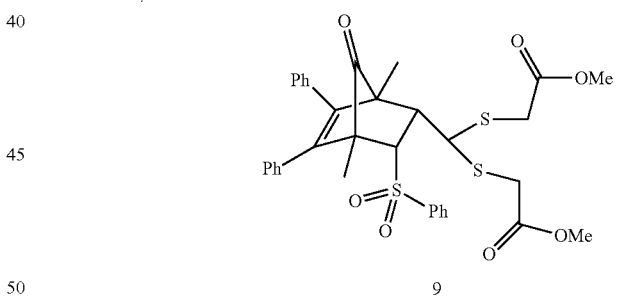

To a solution of 7 (100 mg, 0.22 mmol) and methyl thioacetate (51 mg, 0.48 mmol) in $CH_2Cl_2$ (5 mL) was added $BF_3$-$Et_2O$ (62 mg, 0.44 mmol) dropwise at 0° C. Then the reaction mixture was warmed to room temperature, and was stirred overnight. The reaction mixture was washed with $NaHCO_3$, and the organic layer was separated, and dried over $Na_2SO_4$. After filtration and concentration, the obtained residue was purified on a silica gel column to afford the final product as a white solid (71 mg, yield: 50%). 1H NMR ($CDCl_3$) δ 7.70 (d, J=7.4 Hz, 2H), 7.60 (t, J=7.5 Hz, 1H), 7.42 (t, J=7.8 Hz, 2H), 7.25-7.21 (m, 6H), 7.18-7.16 (m, 2H), 7.13-7.11 (m, 2H), 4.65 (d, J=2.3 Hz, 1H), 4.27 (d, J=6.6 Hz, 1H), 3.85 (s, 3H), 3.79 (s, 3H), 3.63-3.57 (m, 1H), 3.57-3.44 (m, 3H), 3.36 (d, J=16.2 Hz, 1H), 1.63 (s, 3H), 1.50 (s, 3H).

Example 5. Carbon Monoxide Release from pH-Sensitive Compounds

CO-Myoglobin assay. For the CO-myoglobin assay, a solution of myoglobin (0.5 mg/ml) in PBS (10 mL, pH=7.4) was degassed by bubbling with nitrogen for at least 20 min. To this degassed solution was added a solution of 3 (0.45 mg) in DMSO (1 mL), and the resulting solution was incubated at 37° C. for 2 h. Then a solution of sodium dithionite (1 mL, 22 mg/mL) was added to yield a reddish solution, which was cooled down to 0° C. with an ice bath, and was stirred for another 1 h. Afterwards, the UV-vis spectra of the resulting pinkish red solution were taken to confirm CO release.

Figure 2:
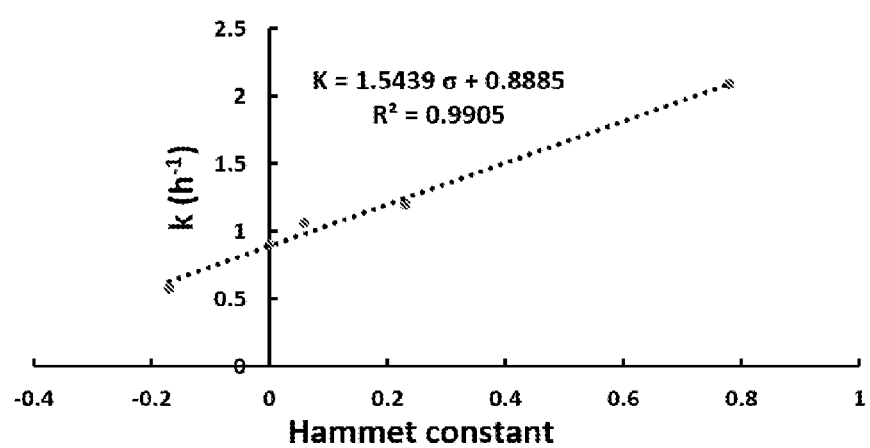
FIG. 2 shows the correlation of CO release rate (k) to Hammet constant (σ) for CO releasing molecules.

All compounds readily underwent beta-elimination in a mixed aqueous solution (Table 1) with concomitant release of CO. The CO release was confirmed by the thoroughly elucidation of the structure of by-product 7 and a widely-accepted CO-myoglobin assay (FIG. 1). As shown in Table 1, by varying the leaving groups, the CO release half-life can be readily tuned from 20 min (2) to 1.2 h (3). Generally, the more electron-withdrawing the R group is, the faster the CO release is. More appealingly, the observed CO release rate constant (Table 1) showed a very good correlation to the Hammet constant of the R groups (FIG. 2, $R^2=0.99$), which is invaluable for quantitatively predicting the half-lives/release rates of newly synthesized CO prodrugs.

TABLE 1

CO release kinetics of compounds 1-6

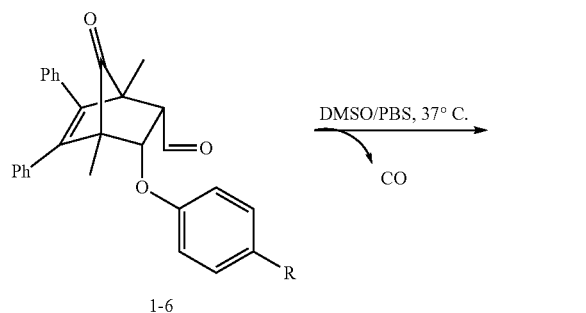

| CO prodrugs | X | R | Hammet constant[a] | k (h$^{-1}$)[b] | $t_{1/2}$ (h)[c] |
|---|---|---|---|---|---|
| 1 | O | H | 0 | 0.9 | 0.77 |
| 2 | O | NO$_2$ | 0.78 | 2.09[d] | 0.33 |
| 3 | O | F | 0.06 | 1.07 | 0.65 |
| 4 | O | Cl | 0.23 | 1.2 | 0.58 |
| 5 | O | Me | −0.17 | 0.58 | 1.2 |
| 6 | S | H | — | 1.33 | 0.52 |

[a]The Hammet constant of R group at para position was extracted from Hansch et al. (*Chem. Rev.* 1991, 91, 165-195);
[b]CO release rate constant was determined in 30% of DMSO in PBS (pH = 7.4) at 37° C. by using HPLC;
[c]CO release half-life was calculated according to $t_{1/2} = 0.693/k$;
[d]The CO release kinetics of 2 was determined by monitoring the formation of 4-nitrophenol using UV absorbance at 400 nm.

Example 6. Study of CO Release Kinetics from pH-Sensitive Compounds

The CO release kinetics of 1-6 were studied in 30% DMSO in PBS (pH=7.4) at 37° C. by monitoring the consumption of CO prodrugs and the formation of compound 1a using HPLC. For prodrug 2, the kinetics were determined by monitoring the formation of 4-nitrophenol using UV spectroscopy, which has a specific absorbance at 400 nm. The HPLC eluent used is acetonitrile/H$_2$O containing 0.05% trifluoroacetic acid (v/v). Two columns were used: Waters C18, 3.5 μm, 4.6×100 mm (for 1, 3 and 5), and Shimadzu C18, 3 μm, 4.6×50 mm (for 4). Each experiment was triplicated.

Compound 3 was chosen to study the pH effects on CO release kinetics by analyzing the disappearance of the CO prodrugs using HPLC (The same HPLC conditions aforementioned were used). Specifically, a solution of 3 in 30% of DMSO in different pH buffer was incubated at 37° C., and the solution was taken for HPLC analysis at intervals. The buffer with different pH values (traceable to SRM of NIST and PTB) were purchased form Aldrich. The simulated gastric fluid without Pepsin was prepared in house. Specifically, 200 mg of NaCl and 0.7 mL of HCl (37%, aq.) was dissolved in 80 ml of DI water, and was transferred into a 100 mL of volumetric flask. Additional DI water was added to make a final volume of 100 mL.

Figure 3:
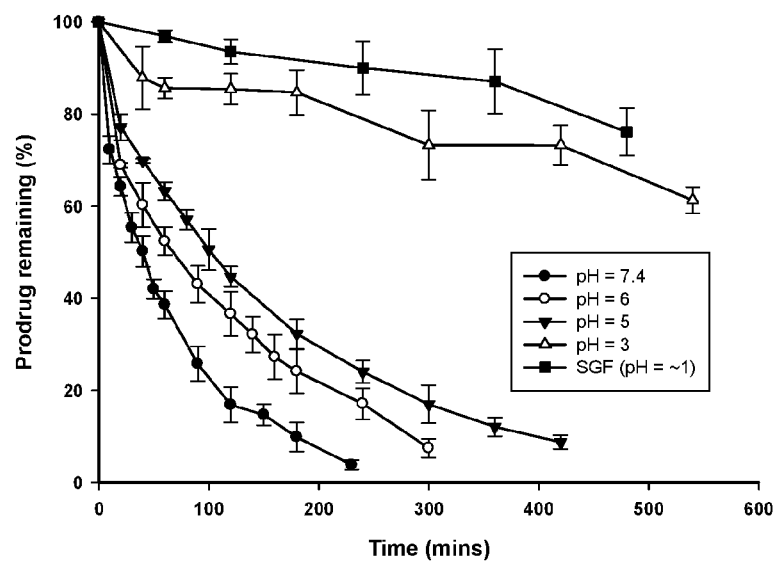
FIG. 3 shows the CO release profiles of compound 3 in different pH buffer at 37° C. SGF: Simulated gastric fluid without Pepsin containing 0.2% of NaCl (w/v) and 0.7% of HCl (v/v).

The CO release from 3 was found to be dependent on the pH of the buffer solution, and was extremely sluggish in acidic buffer solution (pH=3) with a half-life of over 9 h. However, when the pH reached 5, the CO release rate was significantly increased with a half-life of 1.7 h, which was slower when compared to the half-life ($t_{1/2}$=0.65 h) in PBS (pH=7.4). CO release of 3 in simulated gastric fluid (SGF) without Pepsin (pH=~1) was also tested and, advantageously for lower GI tract targeted CO delivery, around 80% of the prodrug remained intact after 8 h of incubation at 37° C. (FIG. 3).

Example 7. Cytotoxicity Study of pH-Sensitive Compounds

Figure 4:
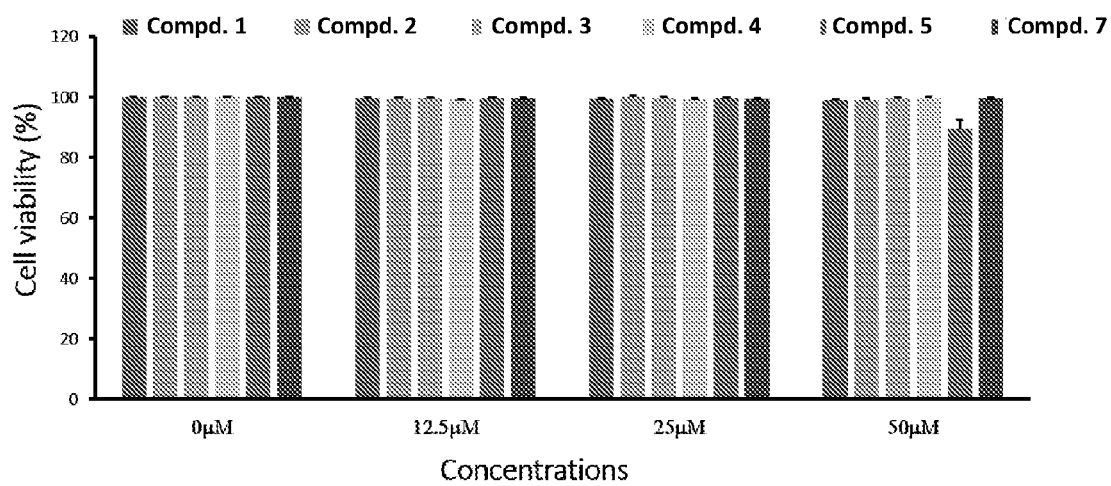
FIG. 4 shows the cytotoxicity of compounds 1-5 and 7 to Raw 264.7 cells
Figure 5:
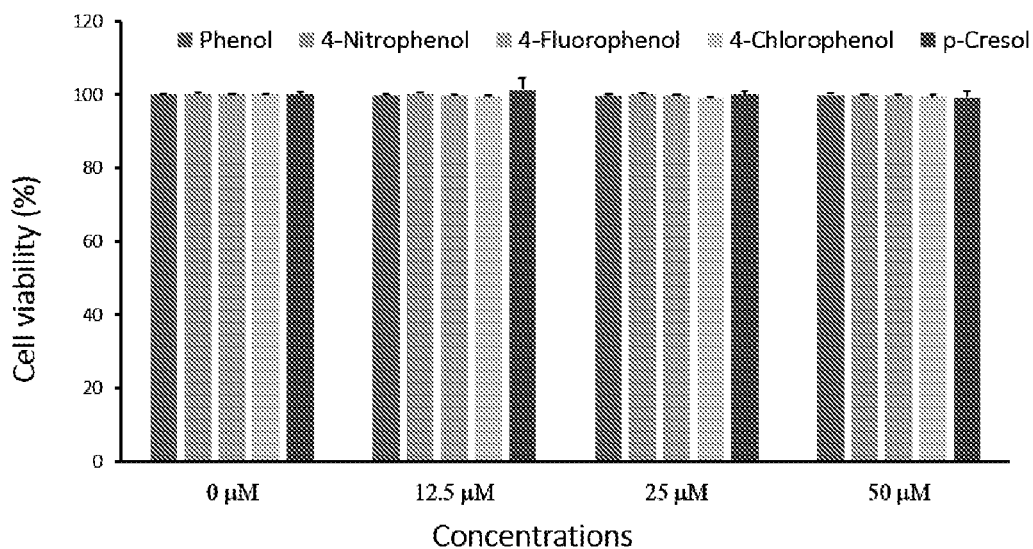
FIG. 5 shows the cytotoxicity of various substituted phenols to Raw 264.7 cells

All CO prodrugs were initially screened for their cytotoxicity against Raw 264.7 cells. Raw 264.7 cells were seeded in 96-well plates and cultured in Dulbecco's modified Eagle's medium (DMEM) supplemented with 10% fetal bovine serum (FBS) and 1% penicillin/streptomycin at 37° C. under 5% CO$_2$ for 24 h. Then RAW 264.7 cells were incubated in DMEM containing 1% DMSO and compounds (0-50 μM) for 24 hours. Then 10 μL of Cell Counting Kit-8 solution was added to each well and incubated for another three hours at 37° C. The absorbance at 570 nm was measured by using a microplate reader. The cell viability was measured, and the results showed that no cytotoxicity was observed for all CO prodrugs along with their respective inactive products (7 and substituted phenols) at concentrations up to 50 μM after 24 h of incubation (FIG. 4-5).

3 and 5 were then chosen for Elisa assay for CO's anti-inflammatory effects, as indicated by TNF-α suppression. RAW 264.7 cells were seeded in 48-well plates one day before the experiment. LPS was used to initiate the inflammatory response in RAW 264.7 cells. RAW 264.7 cells were pre-treated with different concentrations of 3, 5, or their respective inactive control compounds for 4 hours. There after, LPS was added into the cell culture media to make a final concentration of 1 μg/mL. The cells were then incubated at 37° C. for another 1 h, and the cell culture supernatant was collected afterwards. Cell culture without LPS treatment was used as the control. The concentrations of TNF-α in the cell culture supernatant were determined by a commercial ELISA kit (ELISA Ready-SET-Go! ®-eBioscience).

Figure 6:
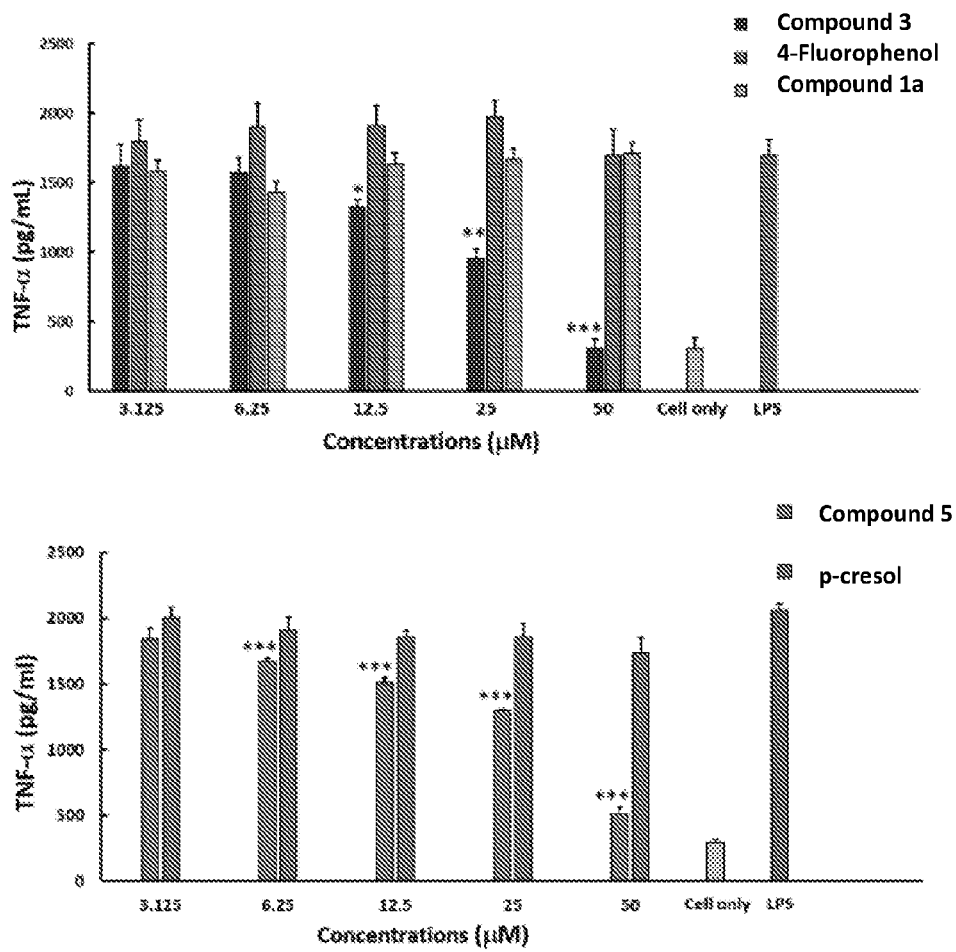
FIG. 6 shows the anti-inflammatory effects of compounds 3 and 5 in Raw 264.7 cells. The mean of each concentration of compound 3 (top panel) and compound 5 (bottom panel) treated group was compared with LPS-only group by two-sample t test. *: p<0.05; : p<0.01; *: p<0.001.

As shown in FIG. 6, both 3 and 5 dose-dependently inhibited LPS-induced secretion of TNF-α, and no similar effects were observed for their respective inactive products, suggesting that the observed TNF-α suppression effects were attributed to the CO release from 3 and 5.

the ones treated with COP-1 only, indicating ready intracellular CO release from 3 and 5.

Example 9. Synthesis of Oxidation-Sensitive CO Releasing Compounds

CO prodrugs 10-11 having phenylselenyl groups were designed and synthesized for selective CO release in response to ROS (Scheme 8). The phenylselenyl group was chosen to achieve a balance between stability and triggered CO release.

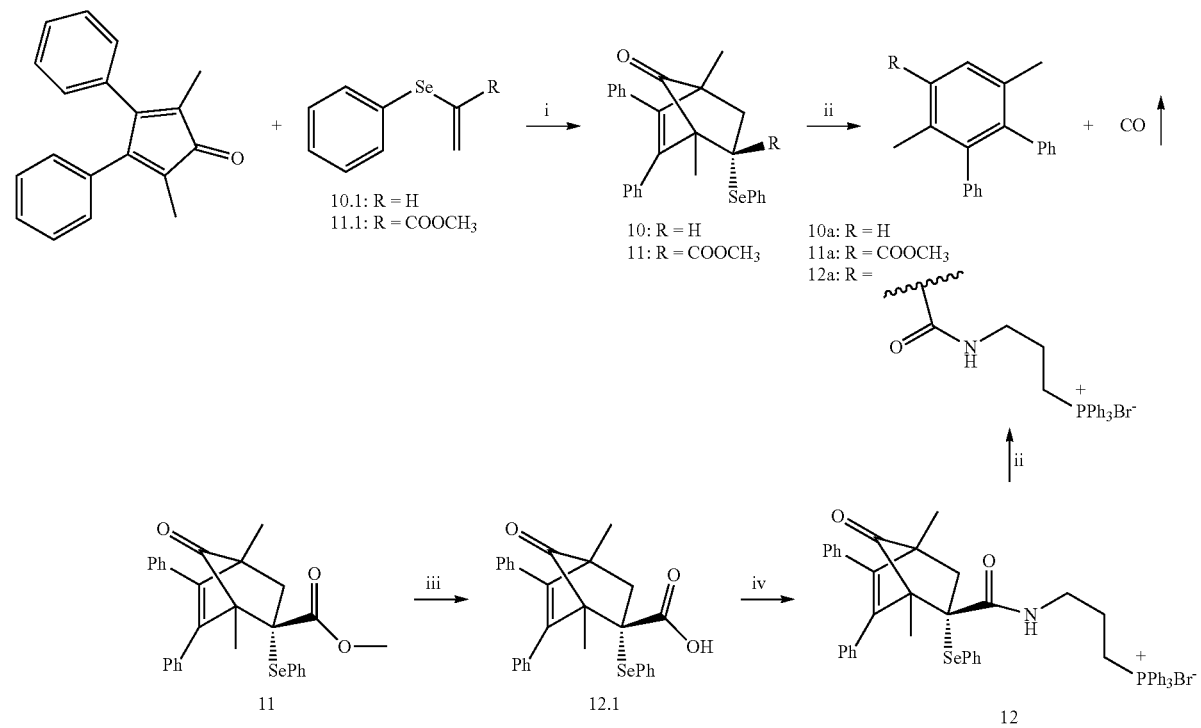

Scheme 8.

Reagents and conditions: (i) toluene, reflux, 12 h; (ii) NaClO (100 mM) in DMSO/PBS(1:5), 37° C.; (iii) LiOH, DMSO/H₂O (5:1), r.t, 12 h; (iv) 1) (COCl)₂, DMF (cat.), DCM, 5 min; 2) (3-aminopropyl)triphenylphosphonium bromide, Et₃N, MS (4Å), DCM, r.t, 1 h.

Figure 7:
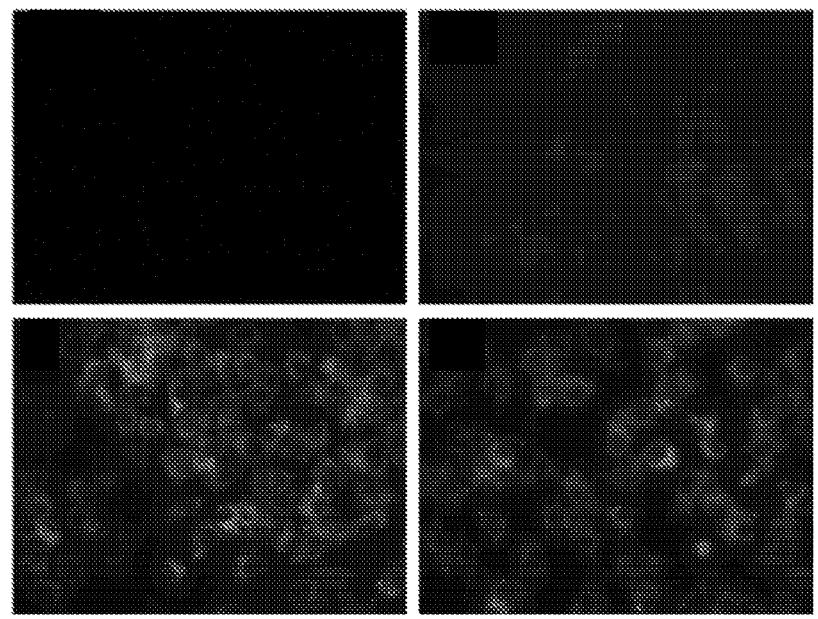
FIG. 7 shows the intracellular CO release from compounds 3 and 5. Top left panel: Cells only. Top right panel: COP-1 (1 µM) only. Bottom left panel: COP-1 (1 µM)+ compound 3 (25 µM). Bottom right panel: COP-1 (1 µM)+ compound 5 (25 µM).

Example 8. Fluorescent Cell Imaging of CO Release from pH-Sensitive Compounds In order to further confirm intracellular CO release from these CO prodrugs, 3 and 5 were chosen for cell image studies using a reported CO fluorescent probe COP-1. RAW 264.7 cells were seeded in the 6-well plate one day before the imaging experiment. Compounds were dissolved in DMSO as stock solution. Final concentration of 1 μM of COP-1 and 25 μM of 3/5 were added into the cell culture. After adding the compounds, the cells were incubated under 37° C. for 5 hours. The cell samples were then fixed for imaging study under FITC channel (excitation: 490 nm, emission: 525 nm) using a Zeiss fluorescent microscope. As shown in FIG. 7, the cells co-treated with COP-1 and 3 or 5 showed much enhanced green fluorescence compared to As shown in Scheme 8, the synthesis of 10 and 11 was readily achieved using a one-step Diels Alder reaction between compound 1a/b and 2. Since mitochondria is established to be a major action site of CO, and it is also the major organelle responsible for ROS generation, compound 12 with a mitochondrion-targeting moiety, triphenylphosphonium (TPP), was therefore synthesized for mitochondrion-targeted CO delivery.

General Procedure A for the synthesis of 10 and 11. A solution of 2, 5-dimethyl-3,4-diphenylcyclopenta-2, 4-dien-1-one (1, 1.0 mmol) and phenyl(vinyl)selane 10.1 or methyl 2-(phenylselanyl)acrylate 11.1 (1.0 mmol) in toluene (10 mL) was heated under reflux for 12 h. Then the reaction mixture was concentrated under vacuum, and the residue was directly purified on a silica gel column to afford the desired product.

1,4-dimethyl-2,3-diphenyl-5-(phenylselanyl)bicyclo[2.2.1]hept-2-en-7-one (10): yellow oil, yield 53%. ¹H NMR (CDCl$_3$): δ 7.59-7.48 (m, 2H), 7.31-7.21 (m, 10H), 7.14-6.97 (m, 3H), 3.78 (dd, J=9.3, 5.3 Hz, 1H), 2.59 (dd, J=13.0, 9.4 Hz, 1H), 2.08 (dd, J=13.0, 5.3 Hz, 1H), 1.30 (d, J=13.8 Hz, 6H). $^{13}$C NMR (CDCl$_3$): δ 204.2, 144.8, 142.1, 134.6, 134.5, 134.0, 133.8, 130.6, 130.1, 129.3, 129.2, 129.1, 129.0, 128.1, 127.8, 127.5, 127.4, 127.1, 58.4, 53.2, 46.4, 41.8, 12.0, 11.8. HRMS (ESI)$^+$ calcd for C$_{27}$H$_{24}$NaOSe [M+Na]$^+$ 525.0885, found: 467.0899.

Methyl-1,4-dimethyl-7-oxo-5,6-diphenyl-2-(phenylselanyl)bicyclo[2.2.1]hept-5-ene-2-carboxylate (11): white solid, yield 67%. $^1$H NMR (CDCl$_3$): δ 7.58-7.52 (m, 2H), 7.44-7.37 (m, 1H), 7.34 (t, J=7.3 Hz, 2H), 7.22-7.10 (m, 6H), 6.92 (ddd, J=9.6, 5.7, 2.2 Hz, 4H), 3.34 (s, 3H), 3.00 (d, J=13.6 Hz, 1H), 2.11 (d, J=13.6 Hz, 1H), 1.74 (s, 3H), 1.20 (s, 3H). $^{13}$C NMR (CDCl$_3$): δ 203.4, 172.7, 147.4, 139.8, 137.2, 134.2, 133.7, 129.6, 129.3, 129.2, 128.8, 128.0, 127.8, 127.5, 127.2, 60.1, 55.0, 52.2, 51.8, 43.9, 11.6, 11.3. HRMS (ESI)$^+$ calcd for C$_{29}$H$_{26}$NaO$_3$Se [M+Na]$^+$525.0939, found: 525.0941.

Synthesis of 1,4-dimethyl-7-oxo-5,6-diphenyl-2-(phenylselanyl)bicyclo[2.2.1]hept-5-ene-2-carboxylic acid (12.1). To a solution of 11 (1.0 mmol, 500 mg) in 5 ml of DMSO/H$_2$O (5:1) was added lithium hydroxide (2 mmol, 48 mg). The resulting mixture was stirred at room temperature for 12 h, and then was poured into 20 mL of ice/water. The pH of the mixture was adjusted to around 2 with 10% of HCl (aq.), and the solution was then extracted with ethyl acetate (3×30 mL). The combined organic phase was washed with brine (10 mL), dried over anhydrous Na$_2$SO$_4$ and evaporated under reduced pressure. The resulting crude product was purified on a silica gel column to afford compound 12.1 as pale yellow solid (440 mg, 90% yield). $^1$H NMR (CDCl$_3$): δ 7.58 (d, J=7.5 Hz, 2H), 7.40 (t, J=7.2 Hz, 1H), 7.32 (d, J=7.6 Hz, 2H), 7.17 (d, J=3.9 Hz, 3H), 7.06-6.84 (m, 7H), 2.85 (d, J=13.6 Hz, 1H), 2.10 (d, J=13.6 Hz, 1H), 1.72 (s, 3H), 1.20 (s, 3H). $^{13}$C NMR (CDCl$_3$): δ 202.7, 177.4, 147.6, 140.1, 137.1, 134.1, 133.6, 129.6, 129.5, 129.3, 128.8, 128.0, 127.9, 127.7, 127.6, 127.3, 60.0, 54.8, 52.3, 43.6, 11.7, 10.7. HRMS calcd for C$_{28}$H$_{23}$O$_3$Se [M−H]$^-$ 487.0818; found 487.0824.

Synthesis of (3-(1,4-dimethyl-7-oxo-5,6-diphenyl-2-(phenylselanyl)bicyclo [2.2.1]hept-5-ene-2-carboxamido)propyl)triphenylphosphonium (12). To a solution of compound 12.1 (0.06 mmol, 30 mg) in anhydrous DCM (4 mL), oxalyl chloride (0.09 mmol, 11 mg) was added at room temperature under the protection of Argon, followed by the addition of one drop of DMF. The resulting solution was stirred at room temperature for 10 min, and then the solvent was directly evaporated in vacuum to afford the corresponding acyl chloride as a pale yellow solid, which was used for the next acylation reaction without further purification. A solution of (3-aminopropyl)triphenylphosphonium bromide (0.09 mmol, 43 mg) and Et$_3$N (30 mg, 0.3 mmol) in anhydrous DCM (2 ml) was dried with molecular sieves (4 A) (20 mg) for 2 h at room temperature under Argon, and then was cannulated to acyl chloride very slowly at 0° C. in 5 min. The mixture was stirred at room temperature for another 1 h and the solvent was evaporated away under reduced pressure. The resulting crude product was purified on a silica gel column to afford the final product as white solid (35 mg, 73% yield). $^1$H NMR (CDCl$_3$): δ 8.50 (s, 1H), 7.75 (br, 3H), 7.67-7.51 (m, 12H), 7.41 (d, J=7.4 Hz, 2H), 7.13-7.02 (m, 8H), 6.94 (s, 5H), 3.93-4.07 (m, 1H), 3.50-3.70 (m, 2H), 3.30-2.55 (m, 1H), 3.29-3.39 (m, 1H), 2.39 (d, J=34.8 Hz, 1H), 2.17 (d, J=13.2 Hz, 1H), 1.75-1.95 (m, 1H), 1.71 (s, 3H), 1.14 (s, 3H). $^{13}$C NMR (CDCl$_3$): δ 203.2, 171.9, 146.4, 139.5, 135.0, 135.0, 134.2, 134.0, 133.6, 133.5, 130.5, 130.4, 129.8, 129.7, 129.1, 129.1, 127.9, 127.7, 127.6, 127.2, 127.0, 118.6, 117.8, 61.3, 57.3, 52.6, 43.9, 40.1, 39.9, 21.8, 20.2, 19.6, 11.9, 11.3. HRMS calcd for C$_{49}$H$_{45}$NO$_2$PSeBr [M−Br]$^+$790.2348; found 790.2368.

General procedure B for the synthesis of 10a-12a. To a solution of compound 10, 11, or 12 (0.3 mmol) in DMSO/PBS (10/1, 1 mL) was added an aqueous solution of NaClO (1M, 0.1 mL), and the resulting solution was stirred at 37° C. until the total consumption of starting material as indicated by TLC. The reaction mixture was then quenched with water (20 mL) and extracted with CH$_2$Cl$_2$ (3×50 ml). The combined organic phase was dried over anhydrous Na$_2$SO$_4$, and was concentrated under reduced pressure. The resulting residue was purified on a silica gel column to afford the title compound.

Methyl 3',6'-dimethyl-[1,1':2',1''-terphenyl]-4'-carboxylate (10): white solid, yield 97%. $^1$H NMR (CDCl$_3$): δ 7.76 (s, 1H), 7.20-7.02 (m, 6H), 6.93 (t, J=7.4 Hz, 4H), 3.96 (s, 3H), 2.27 (s, 3H), 2.11 (s, 3H). $^{13}$C NMR (CDCl$_3$): δ 169.0, 145.0, 143.1, 140.4, 140.2, 134.6, 133.5, 130.3, 130.1, 129.9, 129.5, 127.5, 126.2, 126.2, 52.0, 20.7, 18.7. HRMS calcd for C$_{22}$H$_{20}$O$_2$ [M+H]$^+$ 317.1536; found 317.1541.

3',6'-Dimethyl-1,1':2',1''-terphenyl (11): white solid, yield 91%. H NMR (CDCl$_3$): δ 7.26 (s, 2H), 7.21-7.15 (m, 4H), 7.10-7.14 (m, 2H), 7.00-7.03 (m, 4H), 2.15 (s, 6H). $^{13}$C NMR (CDCl$_3$): δ 141.4, 140.8, 133.5, 130.0, 128.8, 127.4, 125.9, 20.9. HRMS calcd for C$_{20}$H$_{19}$ [M+H]f 259.1481; found 259.1477.

(3-(3',6'-Dimethyl-[1,1':2',1''-terphenyl]-4'-carboxamido)propyl)triphenylphosphonium bromide (12): white solid, yield 89%. $^1$H NMR (CDCl$_3$): δ 9.00 (t, J=5.9 Hz, 1H), 7.79-7.84 (m, 8H), 7.67-7.72 (m, 6H), 7.48 (s, 1H), 7.17-7.02 (m, 6H), 6.91-6.99 (m, 4H), 3.94-4.02 (m, 2H), 3.83 (d, J=5.1 Hz, 2H), 2.09 (d, J=2.1 Hz, 5H), 1.99-2.07 (m, 2H). $^{13}$C NMR (CDCl$_3$): δ 171.6, 142.8, 142.3, 140.8, 140.7, 135.9, 135.1, 135.1, 133.5, 133.4, 131.0, 130.6, 130.5, 130.2, 129.8, 128.0, 127.3, 125.9, 125.8, 118.8, 117.9, 45.8, 39.4, 39.2, 22.8, 22.8, 20.7, 18.3. HRMS calcd for C$_{42}$H$_{39}$NOP$^+$Br$^-$ [M−Br]$^+$ 604.2764; found 604.2771.

A control compound 11b (X=CH$_2$), which would undergo selenoxide elimination without CO release, was also prepared, as shown in Scheme 9. Reagents and conditions: i) toluene, reflux, 12 h; ii) NaClO, DMSO/PBS, 37° C.

Scheme 9

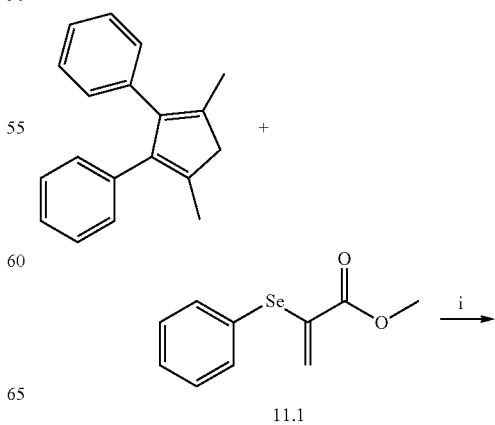

11.1

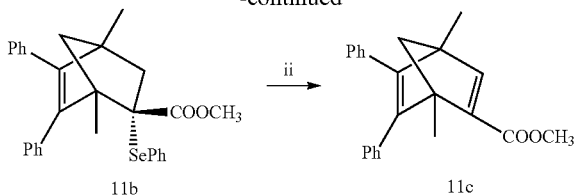

Synthesis of methyl 1,4-dimethyl-5,6-diphenyl-2-(phenylselanyl)bicyclo-[2.2.1]hept-5-ene-2-carboxylate (11b): To a solution of (3,5-dimethylcyclopenta-2,5-diene-1,2-diyl)dibenzene (1.0 mmol, 245 mg) in toluene (10 mL), was added compound 11.1 (1.0 mmol, 242 mg). The mixture was heated under reflux for 12 h, after which the reaction mixture was concentrated under vacuum, and the residue was directly purified on a silica gel column to afford the desired product as colorless oil (235 mg, yield: 48%). $^1$H NMR (CDCl$_3$): δ 7.57-7.61 (m, 2H), 7.29-7.38 (m, 3H), 7.17-7.05 (m, 6H), 6.86-6.94 (m, 4H), 3.03 (s, 3H), 2.97-2.91 (m, 1H), 2.35 (d, J=8.6 Hz, 1H), 2.22 (d, J=13.1 Hz, 1H), 1.85 (dd, J=8.6, 3.1 Hz, 1H), 1.78 (s, 3H), 1.18 (s, 3H). $^{13}$C NMR (CDCl$_3$): δ 173.6, 151.0, 142.1, 136.8, 136.3, 135.6, 130.1, 129.2, 128.9, 128.7, 128.1, 127.7, 127.4, 126.4, 62.5, 61.5, 60.1, 51.0, 50.8, 48.9, 18.2, 17.7. HRMS calcd for C$_{29}$H$_{29}$O$_2$Se [M+H]$^+$ 489.1327; found 489.1364.

Compound 11c was obtained according to the general procedure B.

Methyl 1,4-dimethyl-5,6-diphenylbicyclo[2.2.1]hepta-2,5-diene-2-carboxylate (11c): colorless oil, yield: 93%. $^1$H NMR (CDCl$_3$): δ 7.63 (s, 1H), 7.10-7.25 (m, 7H), 6.96-6.90 (m, 2H), 3.81 (s, 3H), 2.38 (d, J=6.5 Hz, 1H), 2.29 (d, J=6.5 Hz, 1H), 1.60 (s, 3H), 1.41 (s, 3H). $^{13}$C NMR (CDCl$_3$): δ 165.6, 161.2, 155.1, 152.2, 150.2, 136.6, 135.8, 128.3, 128.3, 127.9, 127.8, 126.6, 126.4, 80.6, 60.5, 59.4, 51.3, 16.6, 16.2. HRMS calcd for C$_{23}$H$_{22}$NaO$_2$ [M+Na]$^+$ 353.1512; found 353.1522.

Example 10. CO Release from Oxidation-Sensitive Compounds

The CO release profiles in the absence/presence of ROS was studied using HPLC to monitor the consumption of 10/11 and the formation of 10a/11a. Various ROS solutions were prepared according to literature procedures. A solution of 11 (400 μL, 1 mM in acetonitrile (ACN) was added to 20 mL of PBS (pH 7.4, 10 mM). After stirring at room temperature for 5 min, the freshly prepared ROS stock solution was added to make a final concentration of 500 μM (1 mM for H$_2$O$_2$, 60 μM for NaClO). Additional ACN was added to make the final solution contain 10% of ACN. The resulting mixture was incubated at 37° C. for 30 min. CO release was monitored by the formation of 11a using HPLC. The experiment was triplicated, and the results are reported as mean±SD (n=3).

Figure 8:
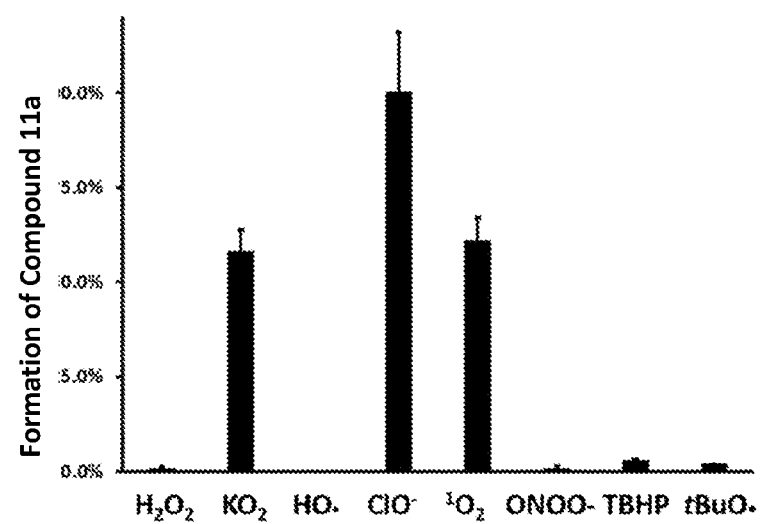
FIG. 8 shows the sensitivity of compound 11 to various ROS at 37° C.
Figure 9:
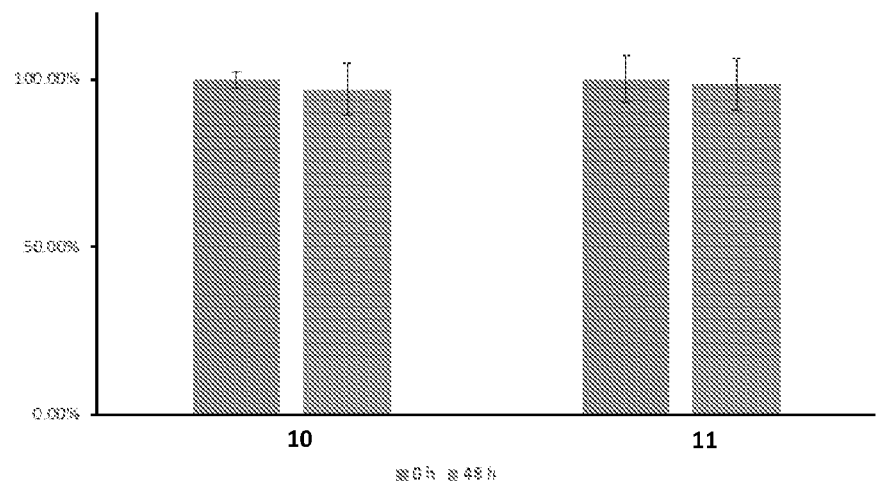
FIG. 9 shows the stability of compound 10 and compound 11 in the absence of ROS.

Initially, 11 was employed to screen its sensitivity towards various ROS. As shown in FIG. 8, 11 is very sensitive to hypochlorite (ClO$^-$), singlet oxygen ($^1$O$_2$) and O$_2^-$, with hypochlorite being the most reactive trigger. For example, the transformation from 11 to 11a completed in 30 min in the presence of hypochlorite (40 μM) at 37° C., and no formation of 11a was observed in the absence of hypochlorite even after 48 h of incubation (FIG. 9). The stability was tested by adding a solution of 11/12 (800 μL, 500 μM in acetonitrile) was added to 20 mL of PBS (pH 7.4, 10 mM) in a vial. Additional acetonitrile was added to make the final concentration of ACN 10% for all solutions. The resulting solution was incubated at 37° C. for 48 h. The solution was then analyzed using HPLC. All the experiments were triplicated, and the results are reported as mean±SD (n=3). As shown in FIG. 9, both 11 and 12 are very stable even after 48 hours of incubation in the absence of ROS.

Figure 10:
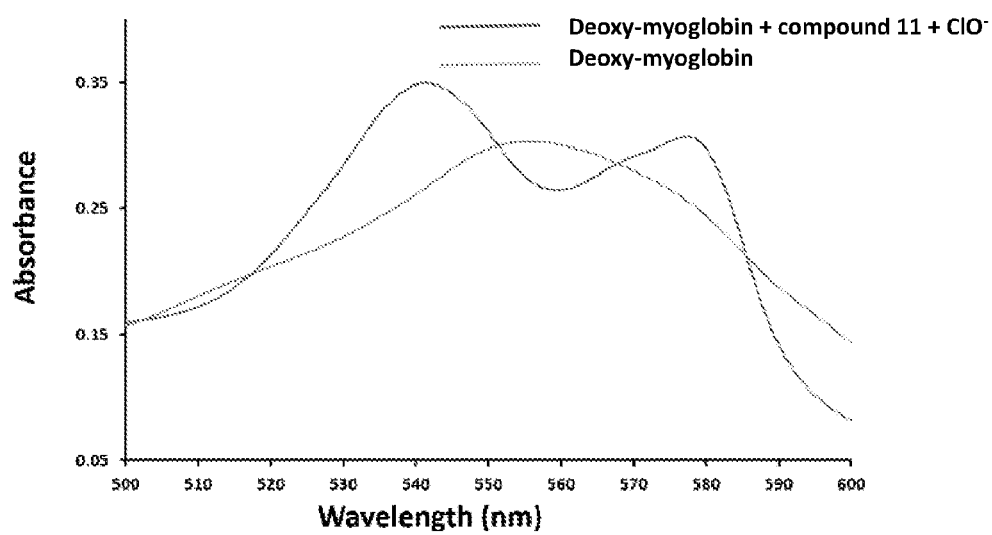
FIG. 10 shows the results of a CO myoglobin assay. Orange curve: absorbance for deoxy-Mb. Blue curve: deoxy-Mb co-treated with compound 11 and NaClO.

Other ROS, such as hydrogen peroxide (H$_2$O$_2$, 1 mM), hydroxyl radical (HO·, 500 μM), tert-butyl hydroperoxide (TBHP, 500 μM) and tert-butoxy radical (tBuO·, 500 μM) only yield less than 5% transformation within 30 min. CO release in the presence of hypochlorite was further confirmed by a widely-accepted CO-myoglobin assay (FIG. 10).

Example 11. Study of Release Kinetics from Oxidation-Sensitive Compounds

Hypochlorite is one of the major ROS generated by immune cells in response to bacterial infection or other inflammations, and it has also been employed as a stimulus to trigger the release of payload from a drug delivery system. In the experiments described here, it was also the most effective in triggering CO release. Therefore, hypochlorite was employed to study the CO release kinetics of 10/11.

A solution of 10/11 (20 μM) and NaClO (40 or 60 μM) in 10% of ACN in PBS (pH=7.4) was sealed and incubated at 37° C. At each defined time point, 500 μL of the reaction mixture was taken out and added into a vial containing Na$_2$SO$_3$ (100 μL, 250 mM) to quench the reaction. The resulting solution was then analyzed by HPLC (column: Waters C18 3.5 μM, 4.6×100 mm, injection loop volume: 20 μL). CO release was determined by monitoring the formation of the product and the consumption of the reaction intermediate as in the case of 10 or prodrug 11. The mobile phase was acetonitrile ACN/H$_2$O (containing 0.05% trifluoroacetic acid). Detailed conditions are summarized in Table 2.

TABLE 2

| The HPLC condition used for analysis | | |
|---|---|---|
| | 10 | 11 |
| Eluent conditions | 0~5 min, 60%~80% ACN; 5~10 min, 80%~95% ACN; 10-13 min, 95%~60% ACN. | 0~8 min, 30%~80% ACN; 8~15 min, 80~95% ACN; 15-18 min, 95%~30% ACN. |
| t$_R$ (min) | Prodrug: 7.5 ± 0.2; Intermediate: 4.2 ± 0.1; 4.9 ± 0.1; Product: 10.5 ± 0.1 | Prodrug: 13.8 ± 0.1; Product: 13.0 ± 0.1 |

Figure 11A:
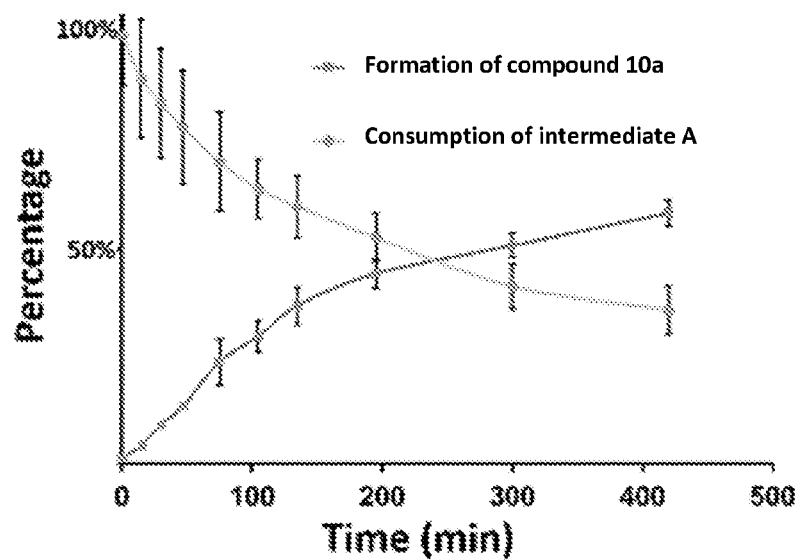
FIG. 11A shows the CO release kinetics of compound 10 in response to hypochlorite, as indicated by both the consumption of compound 10 (and intermediate A) and the formation of 10a. CO release kinetics of compound 10 in the presence of 40 µM ClO⁻ in 10% of acetonitrile in PBS (pH 7.4) at 37° C.
Figure 11B:
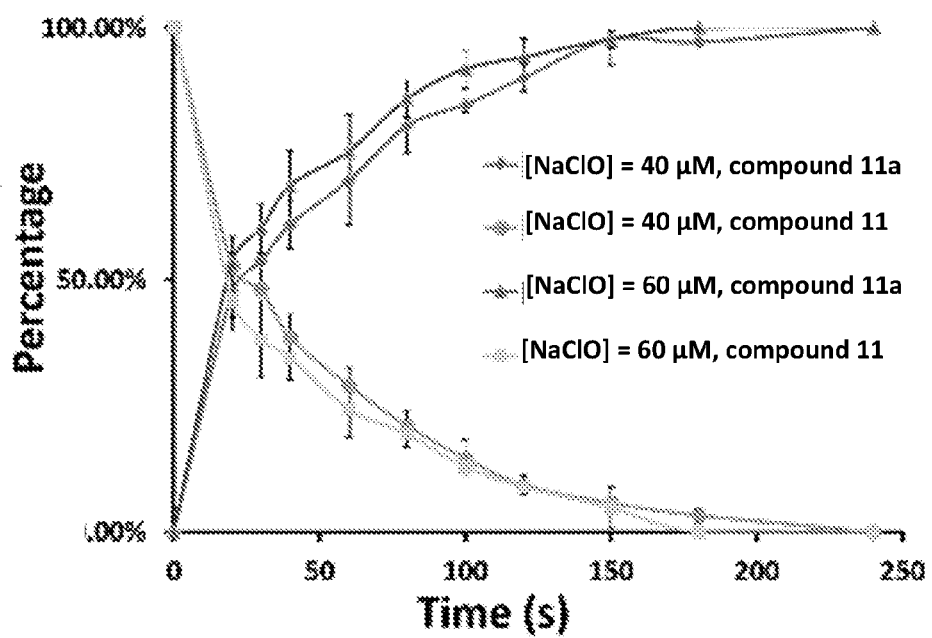
FIG. 11B shows the CO release kinetics of compound 11 in response to hypochlorite, as indicated by both the consumption of compound 11 and the formation of 11a. CO release kinetics of compound 11 in the presence of 40 µM and 60 µM ClO⁻ in 10% of acetonitrile in PBS (pH 7.4) at 37° C.

As shown in FIG. 11, both 10 and 11 could undergo selenoxide elimination to form 10a/11a for CO release in the presence of hypochlorite (40 and 60 μM) at 37° C. In the case of 10 (FIG. 11A), the oxidation step is quite fast (e.g., finished in 30 seconds with an initial hypochlorite concentration of 40 μM), and the accumulation of intermediate A (a mixture of diastereomer, see Scheme 10) was observed. However, the selenoxide elimination is quite sluggish with a half-life of around 4 h. In contrast, the oxidation step is the rate limitation step for 11, and intermediate A was not observed under the HPLC conditions used, indicating a spontaneous selenoxide elimination step. Nevertheless, 11 presented much faster CO release kinetics with a half-life of only around 30 seconds in the presence of 40 μM hypochlorite, as compared to 4 h for 10 under the same conditions.

Scheme 10

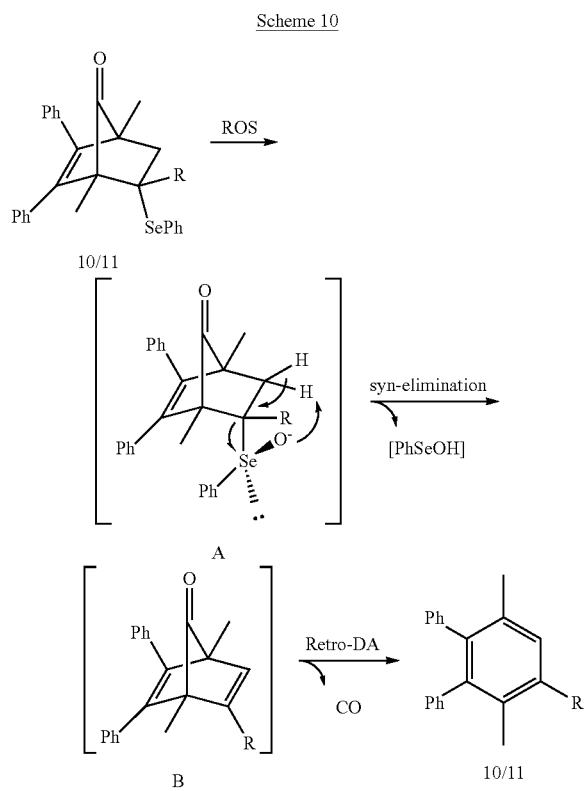

Example 12. Release of CO from Oxidation-Sensitive Compounds in Response to Elevated Intracellular ROS Levels Having confirmed that 10/11 could specifically release CO in response to ROS in vitro, the ability of such CO prodrugs to release CO in response to elevated intracellular ROS levels was studied. Towards this end, 11 was tested for its intracellular CO under various cellular conditions. Toward this end, two types of comparative studies were conducted. First, it is commonly believed that cancer cells have elevated levels of ROS because of its rapid metabolism. Thus, CO release in Hela (cancerous cells) and H9C2 cells (normal cells) was compared. Second, inflammatory responses are known to be associated with elevated levels of ROS. Therefore, a macrophage cell line (Raw264.7) was used with and without LPS stimulation, which is known to trigger inflammatory responses. CO production was monitored by a known fluorescent probe COP-1.

Hela or H9C2 cells were seeded in 6-well plates one day before the imaging experiment. Compound 11 was dissolved in DMSO as stock solution. Final concentrations of 1 µM for COP-1 and 50 µM for 1 were added into the cell culture. The sample without 11 was used as the negative control. After adding the compound, the cells were incubated at 37° C. for 5 hours. The cells were then fixed and taken for fluorescent images under the FITC channel (excitation: 490 nm, emission: 525 nm) using a Zeiss fluorescent microscope.

Raw264.7 cells were seed in 96-well plates and cultured in DMEM supplemented with 10% FBS and 1% penicillin/streptomycin at 37° C. under 5% $CO_2$ for 24 h. The cells were then treated with LPS (1 µg/mL) for 5 h. Then, ROS probe 2',7'-dichlorofluorescein diacetate (10 µM) was added, and incubation continued for another 1 h. The cells were subsequently used for fluorescence scanning (excitation: 485 nm; emission: 535 nm) using Perkin Elmer 1420 multi-label counter. Cells without LPS stimulation were used as controls. LPS was indeed found to induce ROS generation in Raw 264.7 cells.

For imaging studies of 11 in transformed macrophage cells, RAW 264.7 cells were seeded in 6-well plates one day before the imaging experiment. Compounds were dissolved in DMSO as stock solution. Final concentration of 1 µM COP-1, 50 µM of 11 and 1 µg/mL of LPS were added into the cell culture. The cells without 11 was used as the negative control. After adding the compound, the cells were incubated at 37° C. for 5 hours. The cells were then fixed and taken for fluorescent images under the FITC channel (excitation: 490 nm, emission: 525 nm) using a Zeiss fluorescent microscope.

Figure 12:
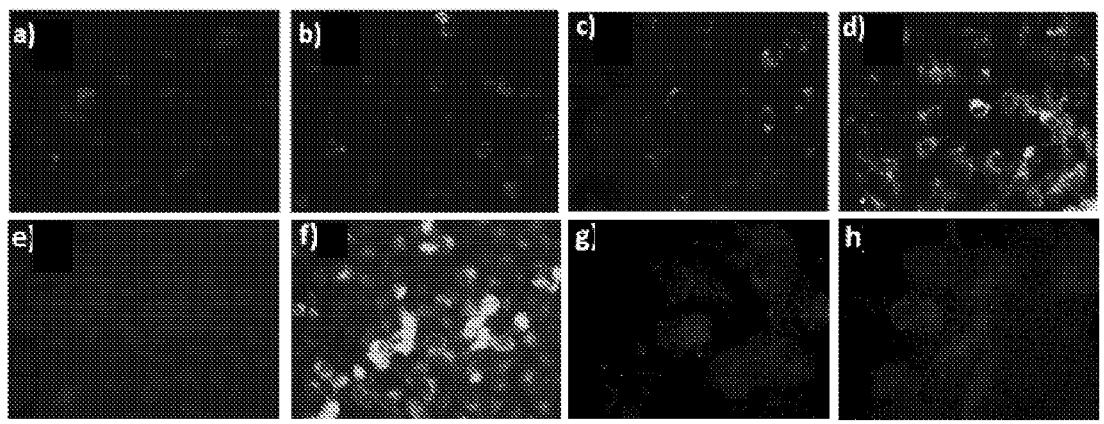
FIG. 12 shows fluorescent imaging studies of CO release of compound 11 in different type of cells. Top row, first panel: COP-1 only (1 µM); Raw264.7 cells. Top row, second panel: LPS (1 µg/mL)+COP-1 (1 µM); Raw264.7 cells. Top row, third panel: compound 11 (50 µM)+COP-1 (1 µM); Raw264.7 cells. Top row, fourth panel: compound 11 (50 µM)+COP-1 (1 µM)+LPS (1 µg/mL); Raw264.7 cells. Bottom row, first panel: e) COP-1 only (1 µM); Hela cells. Bottom row, second panel: COP-1 (1 µM)+compound 11 (50 µM); Hela cells. Bottom row, third panel: COP-1 only (1 µM); H9C$_2$ cells. Bottom row, fourth panel COP-1 (1 µM)+ compound 11 (50 µM); H9C$_2$ cells.

Raw 264.7 cells co-treated with 11, COP-1 and LPS (1 µg/mL) showed significantly enhanced green fluorescence (FIG. 12d) compared to the control cells treated with COP-1 and 11 without the stimulation of LPS (FIG. 12c). Similarly, Hela cells co-treated with 11 and COP-1 also showed much enhanced green fluorescence (FIG. 12f) compared with H9C2 cells under the same conditions (FIG. 12g-h). To firmly establish the connection between CO release and elevated levels of ROS, the ROS levels in these cell lines was determined using a widely employed ROS probe. The experiments with ROS probe 2',7'-dichlorofluorescein diacetate, described above, confirmed that LPS challenged Raw264.7 or Hela cells indeed possessed much higher ROS levels as compared to Raw264.7 cells without LPS or H9C2 cells, respectively. Altogether, these results firmly established the capacity of 11 in selective delivery of CO to disease sites with elevated ROS levels.

Example 13. Sensitization of Cancer Cells to Doxorubicin Treatment with Oxidation-Sensitive CO Releasing Compounds Having confirmed that 11 could selectively deliver CO in response to elevated intracellular ROS level, further studies focused on whether such CO prodrugs could recapitulate CO's synergistic effects with Dox in killing cancer cells. Towards this end, Hela cells and H9C2 cells were co-treated with 11/12 and Dox for 24 h. Then the cells were subjected to crystal violet assay for cytotoxicity evaluation. The cells treated with 11/12, or Dox only were used as controls. Additionally, the cells co-treated with Dox and compound 10a/11a/11b were employed as additional controls as well.

Hela cells and H9C2 cells were seeded in 96-well plates and cultured in DMEM supplemented with 10% FBS and 1% penicillin/streptomycin at 37° C. under 5% $CO_2$ for 24 h. The cells were either incubated with doxorubicin (1% DMSO DMEM solution, 0 to 4 µM) or a mixture of doxorubicin and indicated compounds (1% DMSO DMEM solution, 0 to 4 µM for doxorubicin) for 24 h. After removal of the medium, the plate was washed with 150 µL/well of PBS and the cell was fixed with 4% paraformaldehyde for 1 h at room temperature. The solution in the well was then removed and 100 µL of 0.5% crystal violet staining solution was added to each well. After incubation for 15 min at room temperature, the plate was washed with 200 µL of DI water for each well twice, followed by the addition of 100 µL/well of acetic acid solution (33%) to dissolve the dye. Absorbance at 615 nm was then measured by using a Perkin Elmer 1420 multi-label counter. Cell viability was measured and the results were normalized to the vehicle group. The experiment was triplicated and the results are expressed as mean±SD (n=3).

Figure 13A:
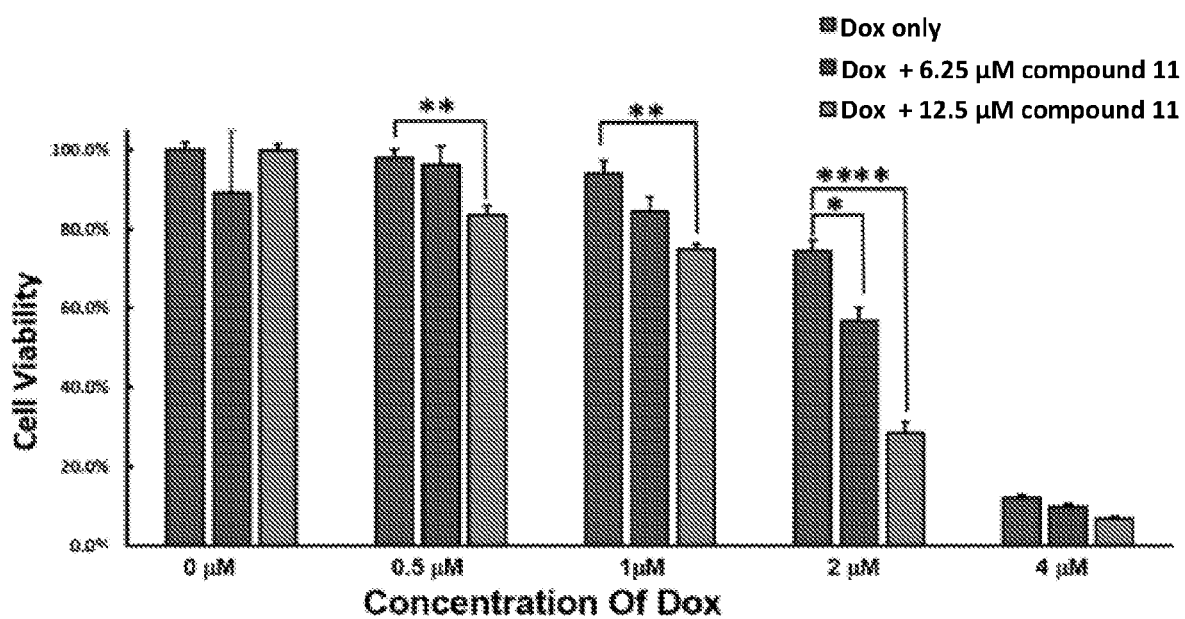
FIG. 13A shows the synergistic effects of compound 11 and doxorubicin (Dox) in killing Hela cells. The mean of each group co-treated with both compounds was compared with Dox-only group (left column in each concentration group) by a two-sample t test. *: p<0.05; : p<0.01; **: p<0.0001.
Figure 13B:
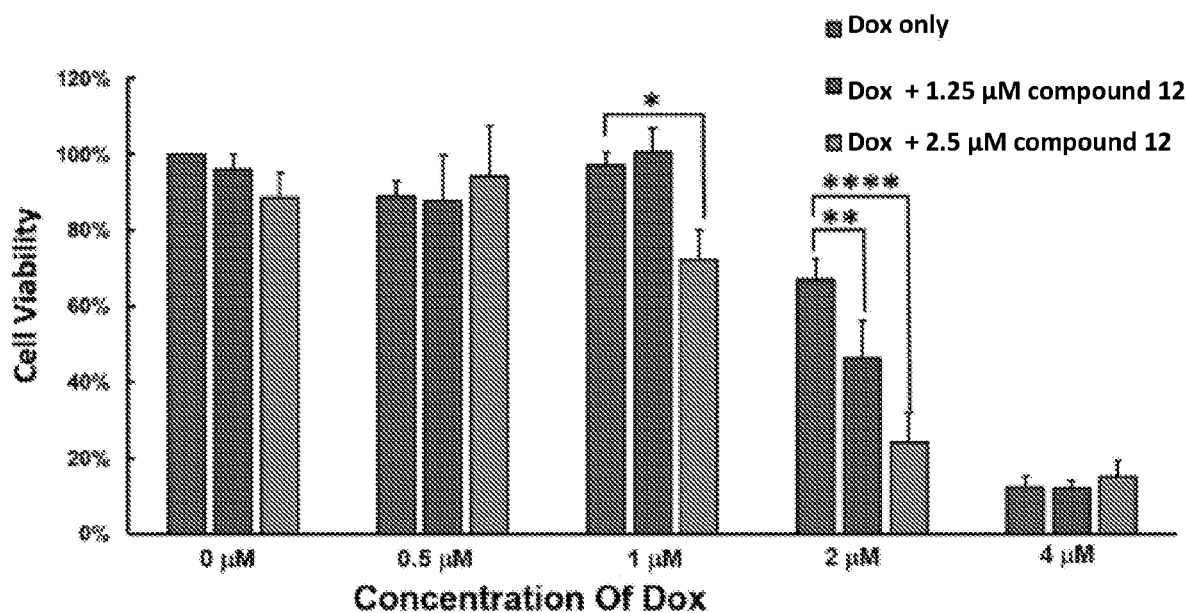
FIG. 13B shows the synergistic effects of compound 12 and doxorubicin (Dox) in killing Hela cells. The mean of each group co-treated with both compounds was compared with Dox-only group (left column in each concentration group) by a two-sample t test. *: p<0.05; : p<0.01; **: p<0.0001.

The results are summarized in FIG. 13. Both 11 and 12 inhibited the proliferation of Hela cells synergistically with Dox. For example, after 24 h of exposure with 2 μM of Dox, the cell viability only decreased to around 80%, and yet this number went down to around 20% when Dox was used in combination with 11 (12.5 μM) or 12 (2.5 μM). As controls, no decrease in cell viability was observed upon treatment with 11/12 only (FIG. 13, the red and green column in the 0-μM group). In addition, no synergistic effects were observed between Dox and the control compound 11 b or the inactive compound 10a/11a after CO release. Taken together, it can be confirmed that the observed synergistic effects were indeed attributed to the CO release from 11/12. Meanwhile, 12 with the ability to target mitochondria was effective at a much lower concentration (2.5 μM) needed for the synergistic effects with Dox than 11. Such results indicate the benefits by targeting such an organelle.

Cell imaging studies (FIG. 13) confirmed that 11 showed negligible CO release in H9C2 cells. Therefore, as expected, no synergistic effects were observed between Dox and 11 in killing H9C2 cells. 11/12 were further assayed for their cytotoxicity against H9C2 cells. It turned out that 12 with a mitochondrion-targeting moiety showed toxicity after 24 h of incubation at 5 μM, which is above the concentration used for the study of synergistic effect. However, no decrease in cell viability was observed for 11 at concentrations of up to 100 μM, indicating a desirable safety profiles for CO prodrugs with such a scaffold.

Example 14. Synthesis of Esterase-Sensitive CO Releasing Compounds

Esterase-sensitive CO releasing compounds were prepared as shown in Scheme 11. Reagents and conditions: (i) Diisobutylaluminium hydride (DIBAL), DCM, −78° C. to r.t., 6 h; (ii) 1) Dess-Martin periodinane (DMP), DCM, r.t, 1 h; 2) 2,5-dimethyl-3,4-diphenylcyclopenta-2,4-dien-1-one, toluene, reflux, 5 h; (iii) Anhydrides, $RuCl_3$, r.t., 12 h; (iv) 30% DMSO/PBS, porcine liver esterase (10 U/mL), 37° C.

Scheme 11.

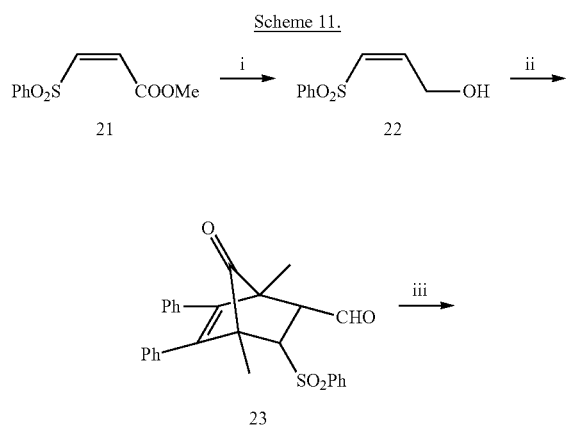

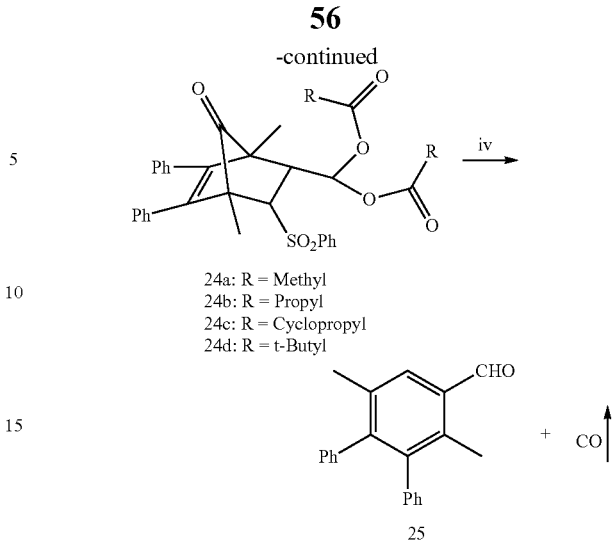

24a: R = Methyl
24b: R = Propyl
24c: R = Cyclopropyl
24d: R = t-Butyl

Synthesis of (Z)-3-(phenylsulfonyl)prop-2-en-1-ol (22). To a solution of methyl (Z)-3-(phenylsulfonyl)acrylate (21, 2.0 mmol, 452 mg) in DCM (15 mL) at −78° C., was slowly added DIBAL solution in DCM (1M, 6 ml). The resulting mixture was warmed to room temperature and stirred for another 6 h. Thereafter, the reaction was quenched with ice water (20 mL) and extracted with $CH_2Cl_2$ (3×30 ml). The combined organic phase was dried over anhydrous $Na_2SO_4$, and concentrated under reduced pressure. The resulting residue was purified on a silica gel column (hexane:EtOAc=2:1) to afford the desired compound 22 as colorless oil in 43% yield (170 mg). $^1$H NMR ($CDCl_3$) δ 7.95-7.87 (m, 2H), 7.70-7.65 (m, 1H), 7.64-7.49 (m, 2H), 6.54-6.41 (m, 1H), 6.27-6.31 (m, 1H), 4.77 (dd, J=5.5, 2.0 Hz, 2H), 2.43 (s, 1H). $^{13}$C NMR ($CDCl_3$) δ 146.2, 140.6, 133.8, 129.7, 129.5, 127.4, 58.5. HRMS calcd for $C_9H_{10}O_3SNa$ [M+Na]$^+$ 221.0244; found 221.0248.

Synthesis of (1S,4S)-1,4-dimethyl-7-oxo-5,6-diphenyl-3-(phenylsulfonyl)bicyclo-[2.2.1]hept-5-ene-2-carbaldehyde (23). To a solution of compound 22 (1.0 mmol, 198 mg) in DCM (5 mL) at r.t., was added DMP (1.5 mmol, 640 mg) and the mixture was stirred for another 1 h. The solution was then directly concentrated under reduced pressure and purified on a silica gel column (hexane:EtOAc=10:1) to afford the crude product 3-(phenyl sulfonyl)acrylaldehyde, which was mixed with 2,5-dimethyl-3,4-diphenylcyclopenta-2,4-dien-1-one (0.8 mmol, 208 mg) in toluene (10 mL). The resulting mixture was heated under reflux for 5 h, after which the reaction mixture was concentrated under vacuum, and the obtained residue was purified on a silica gel column (hexane:EtOAc=5:1) to afford the desired product as colorless oil (270 mg, yield: 60% over two steps). $^1$H NMR ($CDCl_3$) δ 10.13 (d, J=5.3 Hz, 1H), 7.77-7.71 (m, 2H), 7.67 (d, J=7.5 Hz, 1H), 7.54 (t, J=7.8 Hz, 2H), 7.37-7.41 (m, 2H), 7.31-7.20 (m, 6H), 7.10-7.03 (m, 2H), 4.17 (d, J=10.3 Hz, 1H), 3.04 (dd, J=10.3, 5.3 Hz, 1H), 1.44 (s, 3H), 1.35 (s, 3H). $^{13}$C NMR ($CDCl_3$) δ 198.9, 196.2, 157.6, 141.9, 140.2, 139.7, 139.6, 134.5, 133.8, 133.5, 130.7, 129.8, 129.5, 128.5, 128.2, 127.9, 127.8, 70.9, 59.0, 57.6, 57.1, 12.4, 11.3. HRMS calcd for $C_{28}H_{24}O_4SNa$ [M+Na]$^+$479.1293; found 479.1283.

General procedure for the synthesis of 24a-d. Compound 23 (0.1 mmol, 45 mg) and $RuCl_3$ (0.01 mmol, 2 mg) were added to the corresponding anhydride (0.1 ml), and the mixture was stirred at r.t. for 12 h. The reaction was then quenched with water (10 mL) and was extracted with EtOAc (3×20 ml). The combined organic phase was dried over anhydrous $Na_2SO_4$, and concentrated under reduced pressure. The obtained residue was purified on a silica gel column to afford the title compound.

((1S,4S)-1,4-Dimethyl-7-oxo-5,6-diphenyl-3-(phenylsulfonyl)bicyclo [2.2.1]hept-5-en-2-yl)methylene diacetate (24a). The title compound was synthesized according to general procedure with compound 23 (0.1 mmol, 45 mg) and acetic anhydride (0.1 mL). $^1$H NMR ($CDCl_3$) δ 7.77 (d, J=2.7 Hz, 1H), 7.63 (d, J=8.4 Hz, 2H), 7.47 (t, J=7.9 Hz, 2H), 7.34-7.28 (m, 7H), 7.23-7.17 (m, 3H), 4.12 (d, J=11.0 Hz, 1H), 3.24 (dd, J=11.0, 2.7 Hz, 1H), 2.13 (s, 3H), 2.05 (s, 3H), 1.47 (s, 3H), 1.02 (s, 3H). $^{13}$C NMR ($CDCl_3$) δ 196.4, 168.8, 168.6, 142.9, 141.3, 138.7, 134.7, 134.0, 134.0, 130.7, 129.3, 128.4, 127.7, 127.7, 127.5, 127.3, 88.8, 69.8, 56.8, 55.9, 50.7, 20.9, 20.9, 13.3, 13.0. HRMS calcd for $C_{32}H_{30}O_7SNa$ [M+Na]$^+$ 581.1610; found 581.1635.

((1S,4S)-1,4-Dimethyl-7-oxo-5,6-diphenyl-3-(phenylsulfonyl)bicyclo [2.2.1]hept-5-en-2-yl)methylene dibutyrate (24b). The title compound was synthesized according to general procedure with compound 23 (0.1 mmol, 45 mg) and butyric anhydride (0.1 mL). $^1$H NMR ($CDCl_3$) δ 7.70 (d, J=7.7 Hz, 2H), 7.63 (t, J=7.5 Hz, 1H), 7.47 (t, J=7.8 Hz, 2H), 7.28-7.17 (m, 8H), 7.16-7.07 (m, 2H), 6.66 (s, 1H), 3.80 (d, J=5.6 Hz, 1H), 3.14 (d, J=5.1 Hz, 1H), 2.27 (t, J=7.4 Hz, 2H), 2.19 (t, J=7.4 Hz, 2H), 1.58-1.66 (m, 4H), 1.32 (s, 3H), 1.26 (s, 3H), 0.92-1.97 (m, 6H). $^{13}$C NMR ($CDCl_3$) δ 198.1, 171.7, 170.7, 142.8, 139.8, 139.4, 134.0, 133.9, 133.6, 130.6, 129.4, 129.3, 128.7, 128.2, 127.7, 127.6, 127.4, 88.0, 67.6, 56.2, 54.7, 47.1, 35.5, 35.5, 17.9, 17.8, 13.5, 13.4, 12.7, 10.2. HRMS calcd for $C_{36}H_{38}O_7SNa$ [M+Na]$^+$ 637.2236; found 637.2265.

((1S,4S)-1,4-Dimethyl-7-oxo-5,6-diphenyl-3-(phenylsulfonyl)bicyclo [2.2.1]hept-5-en-2-yl)methylene dicyclopropanecarboxylate (24c). The title compound was synthesized according to general procedure with compound 23 (0.1 mmol, 45 mg) and cyclopropanecarboxylic anhydride (0.1 mL). $^1$H NMR ($CDCl_3$) δ 7.72 (d, J=2.6 Hz, 1H), 7.67-7.63 (m, 2H), 7.60 (t, J=7.5 Hz, 1H), 7.46 (t, J=7.8 Hz, 2H), 7.40-7.31 (m, 4H), 7.25-7.29 (m, 3H), 7.18-7.22 (m, 3H), 4.12 (d, J=11.0 Hz, 1H), 3.23 (dd, J=11.0, 2.6 Hz, 1H), 1.68-1.60 (m, 1H), 1.53 (s, 3H), 1.36-1.42 (m, 1H), 1.12-1.03 (m, 5H), 1.04-0.77 (m, 6H). $^{13}$C NMR ($CDCl_3$) δ 196.8, 172.6, 172.5, 143.0, 141.4, 138.8, 134.7, 134.2, 133.9, 130.9, 130.8, 129.2, 128.3, 127.7, 127.6 127.4, 127.3, 88.8, 69.9, 57.0, 56.0, 50.8, 13.3, 13.0, 12.8, 12.6, 9.4, 9.2, 9.1, 8.6. HRMS calcd for $C_{36}H_{34}O_7SNa$ [M+Na]$^+$633.1923; found 633.1951.

((1S,4S)-1,4-Dimethyl-7-oxo-5,6-diphenyl-3-(phenylsulfonyl)bicyclo [2.2.1]hept-5-en-2-yl)methylene bis(2,2-dimethylpropanoate) (24d). The title compound was synthesized according to general procedure with compound 23 (0.1 mmol, 45 mg) and pivalic anhydride (0.1 mL). H NMR ($CDCl_3$) δ 7.78 (d, J=7.5 Hz, 2H), 7.67 (t, J=7.5 Hz, 1H), 7.53 (t, J=7.8 Hz, 2H), 7.24-7.28 (m, 5H), 7.18-7.23 (m, 3H), 7.11-7.16 (m, 2H), 6.32 (s, 1H), 3.61 (d, J=6.4 Hz, 1H), 2.98-3.04 (m, 1H), 1.44 (s, 3H), 1.30 (s, 3H), 1.18 (s, 9H), 1.16 (s, 9H) $^{13}$C NMR ($CDCl_3$) a 198.2, 176.8, 175.4, 142.8, 138.9, 134.3, 133.9, 133.6, 130.6, 129.5, 129.4, 128.7, 128.2, 127.7, 127.6, 127.4, 89.3, 67.7, 56.0, 54.5, 48.0, 39.0, 38.6, 29.7, 27.0, 26.8, 12.6, 10.9. HRMS calcd for $C_{36}H_{34}O_7SNa$ [M+Na]$^+$ 665.2549; found 665.2545.

3',6'-Dimethyl-[1,1':2',1''-terphenyl]-4'-carbaldehyde (25). Solutions of 24a, 24b, and 24c (6 mg) and porcine liver esterase (15 mg) in 30% DMSO/PBS (50 mL) was incubated at 37° C. for 48 h. Then EtOH (60 mL) was added, and the solution was centrifuged to remove the esterase. The obtained solution was concentrated under vacuum, and the residue was acidified with HCl (10%), followed by extraction with ethyl acetate (3×30 mL). The combined organic layer was dried over anhydrous $Na_2SO_4$. After filtration and concentration, the residue was purified on a silica gel column (hexane:EtOAc=10:1) to afford the compound 25 as a white solid. $^1$H NMR ($CDCl_3$) δ 10.42 (s, 1H), 7.79 (s, 1H), 7.11-7.19 (m, 6H), 6.98-6.85 (m, 4H), 2.40 (s, 3H), 2.15 (s, 3H). $^{13}$C NMR ($CDCl_3$) δ 192.9, 147.3, 143.4, 139.9, 139.6, 136.3, 134.3, 133.3, 131.8, 130.1, 129.2, 127.6, 127.6, 126.4, 126.4, 20.7, 16.3. HRMS calcd for $C_{21}H_{18}ONa$ [M+Na]$^+$309.1255; found 309.1248.

Example 15. Study of CO Release Kinetics from Esterase-Sensitive Compounds

A solution of 24a-d (20 μM) and porcine liver esterase (3 U/mL) in 5% of DMSO in PBS (pH=7.4) was sealed and incubated at 37° C. At each defined time point, 250 μL of the reaction mixture was taken out and added into a vial containing 500 μL ethanol. The mixture was incubated in an acetone dry ice bath (−78° C.) for 5 min, and centrifuged for 9 min (14.5×1000 rp) to precipitate the esterase out. The resulting supernatant was then analyzed by HPLC (column: Waters C18 3.5 μM, 4.6×100 mm, injection loop volume: 20 μL). CO release was determined by monitoring the formation of the product 25. The mobile phase was acetonitrile $CH_3CN/H_2O$ (containing 0.05% trifluoroacetic acid). Detailed conditions are summarized in Table 3.

Figure 14:
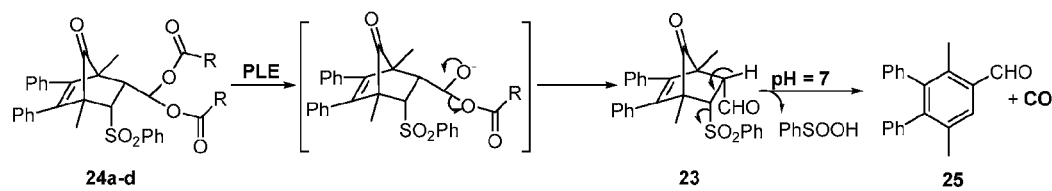
FIG. 14 shows the carbon monoxide release kinetics observed for compounds 24a-c in the presence of pig liver esterase (3 U/mL) in 5% of DMSO in PBS at 37° C.
Figure 14:
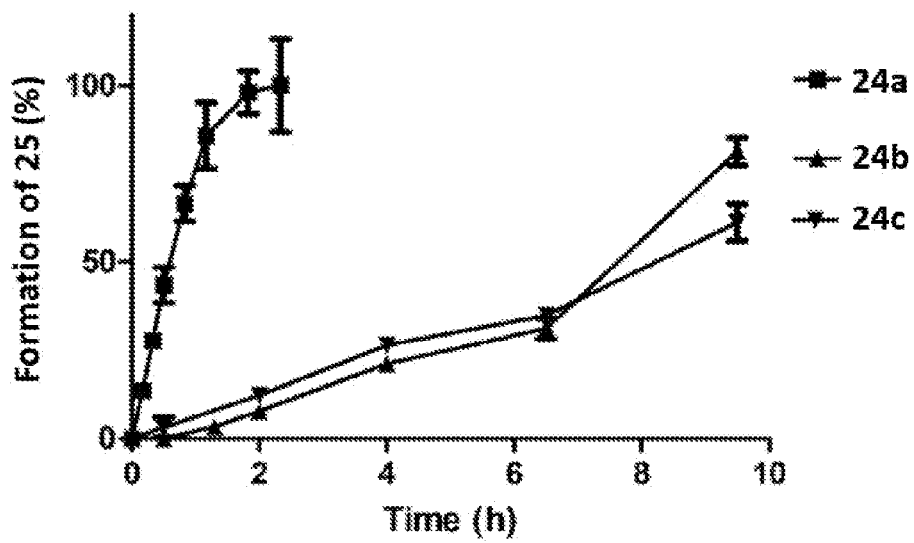

Results of the experiments are shown in FIG. 14. Compounds 24a-c released CO in the presence of porcine liver esterase (PLE) in PBS buffer with release half-life values ranging from 30 min to 8 h. The acetal group in 24a was so sensitive to the PLE that the prodrug was totally consumed within 2 min to form compound 23, which underwent beta-elimination to afford compound 25 concomitantly. With the increasing steric bulk of the R group, the esterase-mediated hydrolysis was significantly decreased and became the rate-limiting step with no build-up of compound 23 throughout the experiment. Especially for compound 24d, no hydrolysis was observed in the presence of PLE even after 24 h of incubation.

TABLE 3

| HPLC conditions and retention times. | | | | | |
|---|---|---|---|---|---|
| Eluent conditions | 0~8 min, 85%~95% ACN; 8-10 min, 95%~85% | | | | |
| Compound | 23 | 24a | 24b | 24c | 24d |
| $t_R$ (min) | Prodrug: 3.2 ± 0.2; Product: 4.6 ± 0.2 | Prodrug: 3.4 ± 0.2; Intermediate: 3.2 ± 0.2; Product: 4.6 ± 0.2 | Prodrug: 5.6 ± 0.2; Intermediate: 2.9 ± 0.2, 3.3 ± 0.2; Product: 4.6 ± 0.2 | Prodrug: 3.8 ± 0.2; Product: 4.6 ± 0.2 | Prodrug: 7.5 ± 0.2 |

Figure 15:
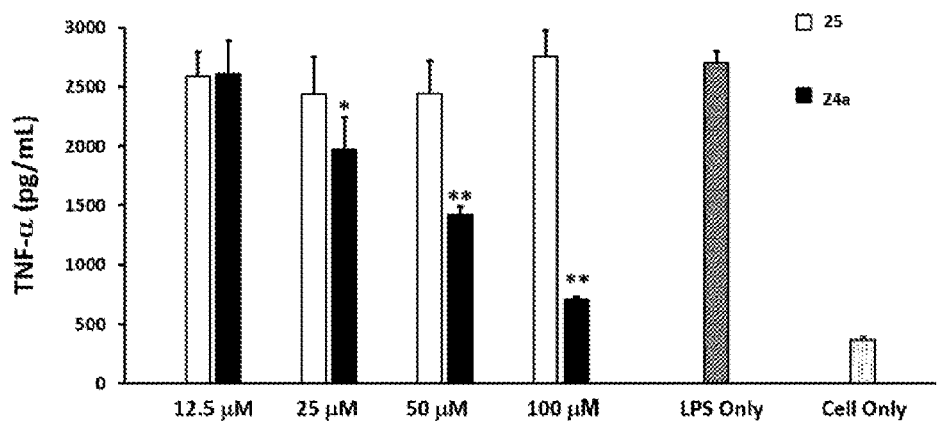
FIG. 15 shows the Anti-inflammatory effects of 24a in LPS challenged Raw264.7 cells. The mean of each concentration of 4a and 5 treated group was compared with LPS-only group by two-sample t-test. *: p<0.05; **: p<0.01.

Example 16. Anti-Inflammatory Effects of Esterase-Sensitive CO-Releasing Compound in Cell Culture RAW 264.7 cells were seeded in 48-well plates one day prior to initiation of the inflammatory response using lipopolysaccharide LPS. The cells were pre-treated with different concentrations of compound 24a for 4 hours. Thereafter, 1

μg/mL LPS was added into the cell culture media. For assay of cytokine TNF-α, the cell culture supernatant was sampled 1 hour after LPS treatment. Cell culture without LPS treatment was used as the control. The concentrations of TNF-α in the cell culture supernatant were measurement by a commercial ELISA kit (ELISA Ready-SET-Go! ®-eBioscience). The results are summarized in FIG. 15.

Example 17. Synthesis of pH-Sensitive CO Releasing Compounds

Compound 29 was synthesized and shown in Scheme 12. Reagents and conditions: i) toluene, reflux, 4 h; ii) DMSO/PBS, 37° C., 8 h.

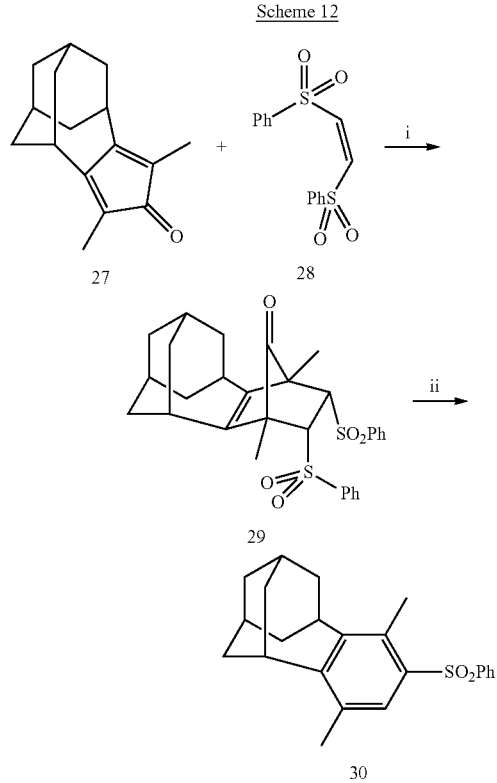

A solution of 27 (123 mg, 0.5 mmol) and 28 (500 mg, 1.6 mmol) in toluene (5 mL) was heated under reflux for 4 h, and the reaction mixture was dried directly. The resulting residue was purified on a silica gel column to afford the desired compound 29 as a white solid (150 mg, 56%). $^1$H NMR (CDCl$_3$) δ 7.94 (d, J=7.5 Hz, 4H), 7.60 (t, J=7.4 Hz, 2H), 7.51 (t, J=7.7 Hz, 4H), 4.21 (s, 2H), 2.69 (t, J=5.1 Hz, 2H), 2.58 (d, J=13.3 Hz, 2H), 2.26 (s, 1H), 2.11 (br, 1H), 1.91-1.74 (m, 6H), 1.51-1.48 (m, 2H), 1.30-1.16 (m, 8H).

A solution of compound 29 (10 mg) in DMSO/PBS (5 mL/5 mL) was incubated at 37° C. for 8 h. Then the reaction mixture was extracted with ethyl acetate (3×30 mL). The organic layer was dried over anhydrous Na$_2$SO$_4$. After concentration, the residue was purified on a silica gel column to yield compound 30 (6 mg, 90%) as a white solid. $^1$H NMR (CDCl$_3$) δ 7.88-7.86 (m, 2H), 7.62-7.55 (m, 1H), 7.56-7.47 (m, 2H), 3.41 (q, J=6.1 Hz, 2H), 2.36 (s, 3H), 2.31 (s, 3H), 2.11 (s, 2H), 2.07-1.91 (m, 4H), 1.86-1.57 (m, 6H). $^{13}$C NMR (CDCl$_3$) δ 153.1, 149.7, 142.4, 135.9, 132.7, 132.6, 131.6, 129.2, 128.9, 127.3, 35.6, 34.0, 33.9, 32.8, 28.0, 21.4, 16.7.

Compound 33 was synthesized according to Scheme 13. Reagents and conditions: i) m-CPBA, CH$_2$Cl$_2$, r.t. overnight; ii) xylene, 7, reflux, 12 h.

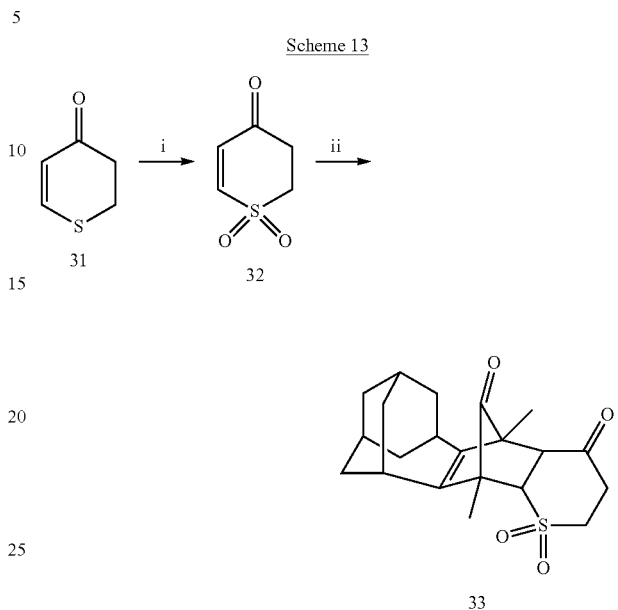

Compound 32: A solution of 31 (600 mg, 5.3 mmol) and m-CPBA (3.0 g, 13.1 mmol, 75%) in CH$_2$Cl$_2$ (40 mL) was stirred at room temperature overnight. Then the reaction mixture was filtered, and the filtrate was dried. The obtained residue was purified on a silica gel column to yield compound 32 (658 mg, 85%) as a white solid. $^1$H NMR (CDCl$_3$) δ 7.20 (d, J=11.2 Hz, 1H), 6.39 (d, J=11.2 Hz, 1H), 3.62 (t, J=9.7, 2H), 3.23 (t, J=9.7, 2H).

Compound 33: 33 was obtained (yield: 20%) as a white solid according to the procedure used to synthesize 29. H NMR (CDCl$_3$) δ 3.39-3.31 (m, 1H), 3.25-3.09 (m, 2H), 3.09-2.95 (m, 2H), 2.72-2.64 (m, 1H), 2.57 (t, J=6.0 Hz, 1H), 2.50 (t, J=6.0 Hz, 1H), 2.17 (br, 2H), 2.02-1.89 (m, 2H), 1.89-1.76 (m, 4H), 1.66-1.63 (m, 2H), 1.58 (br, 2H), 1.54 (s, 3H), 1.13 (s, 3H).

CO prodrug 42 was synthesized according to Scheme 15.

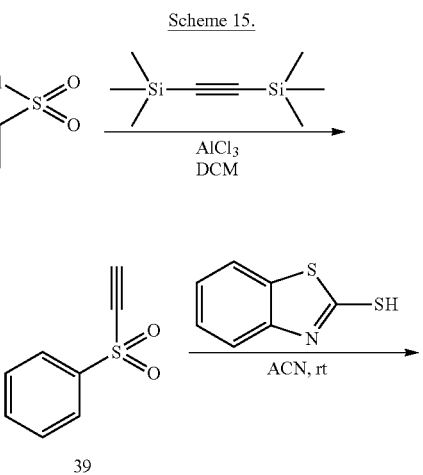

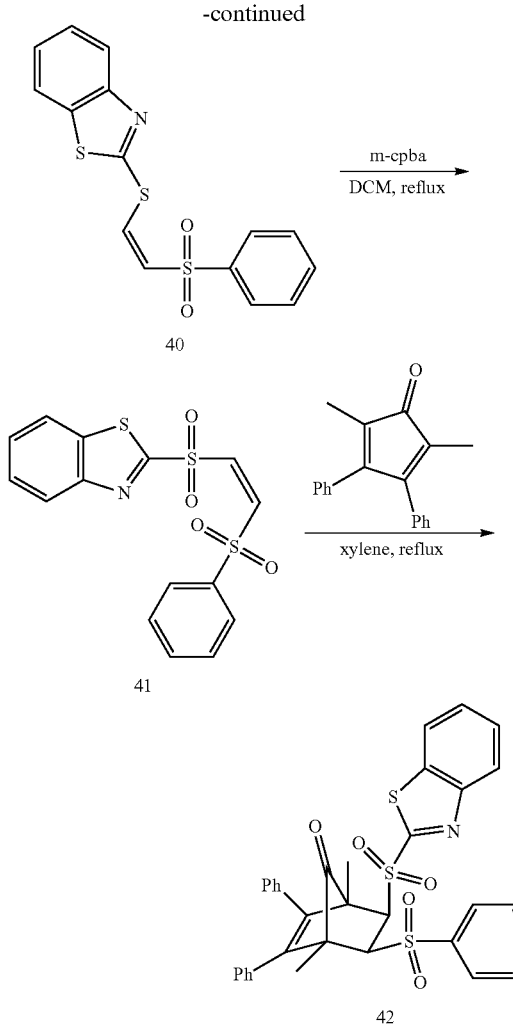

Compound 39: A mixture of benzenesulfonyl chloride (5.5 mL, 43 mmol) and AlCl₃ (5.7 g, 43 mmol) in dichloromethane was stirred at room temperature for 30 min. Then using a cannula, this solution was slowly added to an ice-cold solution of bis(trimethylsilyl)acetylene (6.6 g, 39 mmol). The reaction mixture was stirred at room temperature for 24 h. Quenching was done by adding the reaction mixture to 1N HCl in ice. Layers were separated, washing the aqueous layers with dichloromethane. The combined organic layers were washed with water, brine, dried over Na₂SO₄, and concentrated by rotary evaporation. Purification by silica gel column chromatography using 100:10 hexane:ethyl acetate to give a white solid (4.7 g). ¹H NMR (CDCl₃): δ=7.99-7.97 (m, 2H), 7.72-7.68 (m, 1H), 7.61-7.57 (m, 2H), 3.63 (s, 1H). ¹³C NMR (CDCl₃): δ=140.5, 134.8, 129.5, 127.5, 82.3, 79.9.

Compound 40: To a solution of 39 (230 mg, 1.4 mmol) in acetonitrile stirred at 0° C. was added benzo[d]thiazole-2-thiol (244 mg, 1.5 mmol). The reaction mixture was stirred for 1.5 h. At the completion of the reaction, the mixture was concentrated by rotary evaporation. Purification by silica column chromatography using pure dichloromethane gave a white solid (416 mg). ¹H NMR (CDCl₃): δ=8.48 (d, J=12.0 Hz, 1H), 8.00-7.98 (m, 2H), 7.92 (d, J=7.8 Hz, 1H), 7.8 (d, J=8.0 Hz, 1H), 7.68-7.63 (m, 1H), 7.58-7.55 (m, 2H), 7.49-7.45 (m, 1H), 7.39-7.35 (m, 1H), 6.52 (d, J=10.2 Hz, 1H). ¹³C NMR (CDCl₃): δ=162.4, 152.4, 140.6, 137.8, 135.6, 134.1, 129.5, 127.5, 126.8, 125.4, 125.1, 122.3, 121.6.

Compound 41: To a solution of 40 (250 mg, 0.8 mmol) in dichloromethane stirred at room temperature was added m-CPBA (388 mg, 2.3 mmol). The reaction mixture was stirred and heated to 40° C. for 12 h. At the completion of the reaction, the mixture was concentrated by rotary evaporation. Purification by silica column chromatography using pure dichloromethane gave a white solid (416 mg). ¹H NMR (CDCl₃): δ=8.17 (d, J=7.6 Hz, 1H), 8.03-8.01 (m, 3H), 7.71-7.54 (m, 5H), 7.34 (d, J=11.6 Hz, 1H), 7.02 (d, J=11.6 Hz, 1H). ¹³C NMR (CDCl₃): δ=166.6, 152.3, 142.2, 138.5, 138.4, 136.9, 135.0, 129.7, 129.0, 128.5, 127.9, 125.6, 122.6.

Compound 42: Compound 41 (140 mg, 0.4 mmol) and 2,5-dimethyl-3,4-diphenylcyclopenta-2,4-dien-1-one (50 mg, 0.2 mmol) were suspended in o-xylene and refluxed for 12 h. At the completion of the reaction, the mixture was concentrated by rotary evaporation. Purification by silica column chromatography using hexane:ethyl acetate 100:10 gave a white solid. ¹H NMR (CDCl₃): δ=8.22 (d, J=8.0 Hz, 1H), 8.13 (d, J=8.1 Hz, 1H), 8.01-7.91 (m, 3H), 7.72-7.49 (m, 4H), 7.24-7.18 (m, 10H), 5.59 (d, J=10.2 Hz, 1H), 4.48 (d, J=10.2 Hz, 1H), 1.60 (s, 3H), 1.10 (s, 3H).

Example 18. Synthesis and Activity of an Oxidation-Sensitive CO Releasing Compound ROS-sensitive CO prodrug 38 was synthesized as shown in Scheme 14. Conditions: i) K₂CO₃, H₂O, r.t., overnight; ii) DIBAL, CH₂Cl₂, −78° C., 1-2 h; iii) DIPEA, MOMCl, CH₂Cl₂, r.t., 3 h; iv) toluene, 160° C., 12 h; then HCl, MeOH, reflux, 1 h; v) CH₂Cl₂, PCC, reflux, 30 min.

Scheme 14

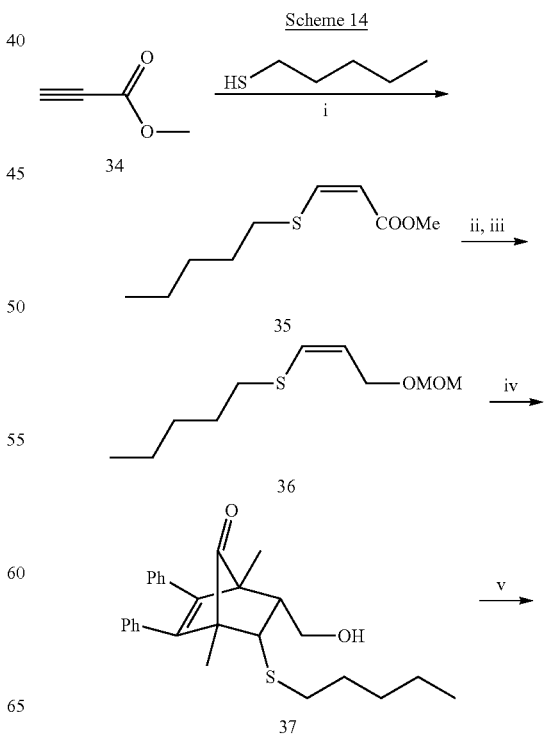

-continued

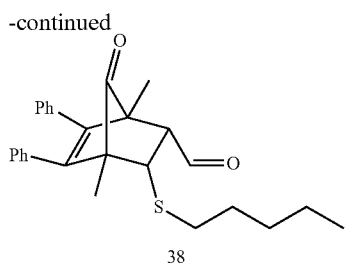

38

Compound 35: To a solution of pentanethiol (2.0 g, 19.2 mmol) and $K_2CO_3$ (2.9 g, 21.1 mmol) in water (50 mL), was added methyl propionate (1.9 g, 23 mmol) dropwise at room temperature. The resulting mixture was stirred at room temperature overnight, and then extracted with ethyl acetate (3×40 mL). The combined organic layer was washed with 5% of NaOH and brine successively, and dried over anhydrous $Na_2SO_4$. After filtration and concentration, the obtained residue was purified on a silica gel column to afford the title compound 35 (3.2 g, 90%) as a colorless oil. $^1$H NMR (CDCl$_3$) δ 7.11 (d, J=10.2 Hz, 1H), 5.86 (d, J=10.2 Hz, 1H), 3.75 (s, 3H), 2.77 (t, J=7.2 Hz, 2H), 1.77-1.65 (m, 2H), 1.49-1.28 (m, 4H), 0.92 (t, J=7.2 Hz, 3H).

Compound 36. To a solution of 34 (1.0 g, 5.3 mmol) in dry $CH_2Cl_2$ (50 mL) was added DIBAL (13.8 mL, 1N, 13.8 mmol) dropwise under $N_2$ at −78° C. The resulting reaction mixture was stirred for another 1 h at −78° C. before being poured into saturated Rochelle salt solution (50 mL) carefully. The resulting mixture was stirred for another 30 min at room temperature. The organic layer was separated, and the aqueous layer was extracted with $CH_2Cl_2$ (2×40 mL). The combined organic layer was washed with brine, and dried over anhydrous $Na_2SO_4$. After filtration and concentration, the obtained residue was dissolved in $CH_2Cl_2$ (30 mL), followed by the addition of DIPEA (1.0 g, 8 mmol) and MOMCl (672 mg, 8 mmol) at room temperature. The resulting solution was stirred for another 3 h at room temperature. Then the reaction mixture was washed with water and brine, and was dried over anhydrous $Na_2SO_4$. After filtration and concentration, the obtained residue was purified on a silica gel column to afford the title compound as colorless oil (730 mg, 67%). $^1$H NMR (CDCl$_3$) δ 6.19 (d, J=9.6 Hz, 1H), 5.72 (dt, J=9.6, 6.4 Hz, 1H), 4.66 (s, 2H), 4.19 (d, J=6.4 Hz, 2H), 3.40 (s, 3H), 2.72-2.64 (m, 2H), 1.70-1.59 (m, 2H), 1.44-1.27 (m, 4H), 0.91 (t, J=6.9 Hz, 3H).

Compound 37. A solution of 36 (400 mg, 1.9 mmol) and dienone compound 2,5-dimethyl-3,4-diphenylcyclopenta-2,4-dien-1-one (171 mg, 0.6 mmol) in xylene (2 mL) was heated to 170-180° C. in a sealed tube for 12 h. Then the reaction mixture was concentrated under vacuum, and the obtained residue was purified on a silica gel column (hexane/ether=10:1) to afford a yellowish oil, which was dissolved in MeOH (5 mL) containing 1 mL of HCl aqueous solution (37%). The resulting solution was heated under reflux for 1 h. Then the reaction mixture was concentrated, and the obtained residue was taken up with ethyl acetate (40 mL). The organic layer was then washed with brine, and was dried over anhydrous $Na_2SO_4$. After filtration and concentration, the obtained residue was purified on a silica gel column to afford the title compound (60 mg, 30%). $^1$H NMR (CDCl$_3$) δ 7.28-7.13 (m, 8H), 7.07-6.91 (m, 2H), 3.88 (dd, J=11.8, 9.5 Hz, 1H), 3.76 (dd, J=11.8, 4.3 Hz, 1H), 3.30 (d, J=9.6 Hz, 1H), 2.82-2.63 (m, 3H), 1.69-1.63 (m, 2H), 1.46-1.30 (m, 10H), 0.93 (t, J=7.1 Hz, 3H). $^{13}$C NMR (CDCl$_3$) δ 203.7, 142.7, 142.2, 134.8, 134.7, 130.4, 129.7, 128.1, 127.6, 127.2, 127.1, 61.8, 59.5, 56.0, 54.0, 51.1, 35.3, 31.0, 30.1, 22.3, 13.9, 11.5, 11.5.

Compound 38. A mixture of 37 (50 mg, 0.12 mmol) and PCC (51 mg, 0.24 mmol) in $CH_2Cl_2$ (20 mL) was heated under reflux for 30 min. Then the reaction mixture was filtered through a short (Ø=2 cm, L=2 cm) silica gel column under reduced pressure, and the obtained filtrate was dried directly to afford the title compound as white solid (43 mg, 86%). $^1$H NMR (CDCl$_3$) δ 9.86 (d, J=5.4 Hz, 1H), 7.29-7.15 (m, 8H), 7.03-6.94 (m, 2H), 3.49 (d, J=9.6 Hz, 1H), 3.04 (dd, J=9.6, 5.4 Hz, 1H), 2.58 (dd, J=13.6, 7.2 Hz, 2H), 1.67-1.51 (m, 3H), 1.44 (s, 3H), 1.41-1.32 (m, 6H), 0.91 (t, J=7.1 Hz, 3H). $^{13}$C NMR (CDCl$_3$) δ 202.1, 200.8, 143.4, 141.0, 134.3, 134.2, 130.3, 129.7, 128.3, 128.0, 127.6, 127.5, 58.7, 58.5, 57.1, 52.3, 33.8, 30.9, 29.2, 22.2, 13.9, 11.6, 10.8, 1.0.

Figure 16A:
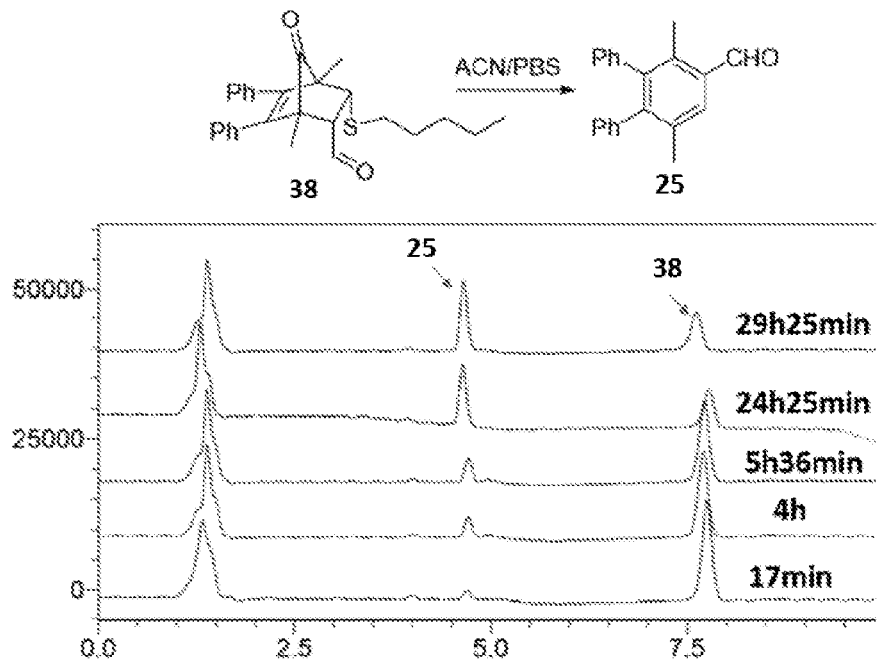
FIG. 16A shows the CO release profile observed for compound 38 in the absence of hydrogen peroxide.
Figure 16B:
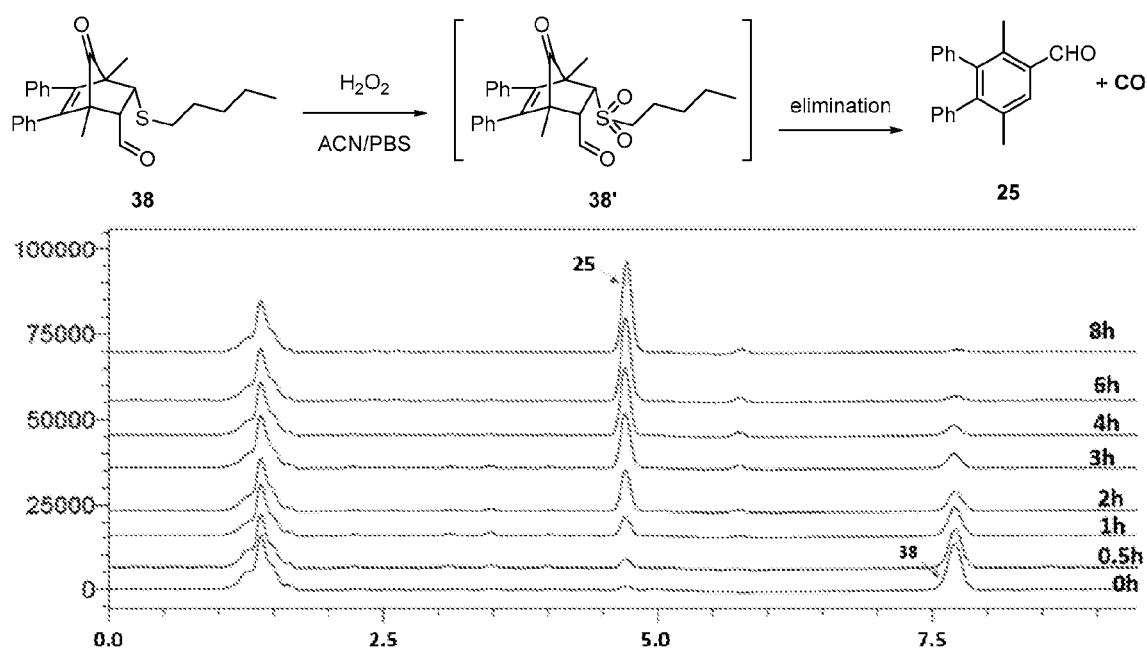
FIG. 16B shows the CO release profile observed for compound 38 in the presence of $H_2O_2$.

Solutions of 38 (20 μM) in 20% of DMSO/PBS was incubated with or without $H_2O_2$ (270 μM) at 37° C. Aliquots were taken for HPLC analysis to determine CO release kinetics by monitoring the formation of compound 25. HPLC was conducted using a Waters C18 column (3.5 LM, 4.6× 100 mm) equipped with a 20-μL injection loop and acetonitrile:water (85:15) as the mobile phase. The results are summarized in FIG. 16A and FIG. 16B.

The beta-elimination half-life observed for compound 38 was around 24 h. However, in the presence of $H_2O_2$ (270 μM), the half-life was significantly decreased to around 1.5 h, demonstrating specific CO release in response to reactive oxygen species.

VIII. Exemplary Embodiments

Exemplary embodiments provided in accordance with the presently disclosed subject matter include, but are not limited to, the claims and the following embodiments:

1. A compound comprising a cyclopentenone moiety and a reactive moiety, wherein exposure of compound to physiological conditions results in elimination of the reactive moiety and release of carbon monoxide.
2. The compound of embodiment 1, wherein the reactive moiety is a leaving group.
3. The compound of embodiment 2, wherein a change in pH upon exposure to physiological conditions results in elimination of the leaving group.
4. The compound of embodiment 2, wherein enzyme activity upon exposure to physiological conditions results in elimination of the leaving group.
5. The compound of embodiment 1, wherein the reactive moiety is a leaving group precursor.
6. The compound of embodiment 5, wherein exposure of the leaving group precursor to reactive oxygen species upon exposure to physiological conditions results in formation of a leaving group and elimination of the leaving group.
7. The compound of embodiment 1, having a structure according to Formula I:

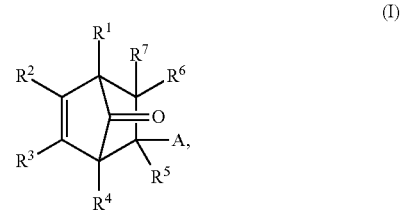

(I)

or a pharmaceutically acceptable salt thereof, wherein:

$R^1$, $R^2$, $R^3$, and $R^4$ are independently selected from the group consisting of H, $C_{1-8}$ alkyl, $C_{3-8}$ cycloalkyl, $C_{6-10}$ aryl, 3- to 8-membered heterocyclyl, 5- to 12-membered heteroaryl, and —C(O)$OR^8$;

$R^2$ and $R^3$ are optionally taken together to form a fused bicyclic moiety or a fused tricyclic moiety;

$R^5$ is selected from the group consisting of H, $C_{1-8}$ s alkyl, —CN, —C(O)$OR^9$, —C(O)$R^{10}$, —C(O)N($R^{11}$)$_2$, and a targeting moiety;

$R^6$ and $R^7$ are independently selected from the group consisting of H, $C_{1-8}$ alkyl, —CN, —C(O)$OR^9$, —C(O)$R^{10}$, —CH(O$R^{10}$)$_2$, —CH(S$R^{10}$)$_2$, —C(O)N($R^1$)$_2$, —S(O)$R^{12}$, and —S(O)$_2R^{12}$;

A is the reactive moiety, which is selected from the group consisting of —Se$R^{13}$, —OS(O)$_2R^{14}$, —S$R^{14}$, —S(O)$R^{14}$, —S(O)$_2R^{14}$, —O$R^{15}$, —OP(O)(O$R^{15}$)$_2$, —OC(O)$R^{16}$, —OC(O)N($R^{17}$)$_2$, —N$^+$($R^{17}$)$_3$, and halogen;

$R^8$ is selected from the group consisting of H and $C_{1-6}$ alkyl;

each $R^9$, $R^{10}$, $R^{11}$, and $R^{12}$ is independently selected from the group consisting of H, $C_{1-8}$ alkyl, $C_{2-8}$ acyl, $C_{6-10}$ aryl, and a targeting moiety;

each $R^{13}$, $R^{14}$, $R^{15}$, $R^{16}$, and $R^{17}$ are selected from the group consisting of $C_{1-8}$ alkyl, $C_{3-8}$ cycloalkyl, $C_{6-10}$ aryl, and 5- to 12-membered heteroaryl;

in $R^6$ or $R^7$, one of $R^9$, $R^{10}$, $R^{11}$, and $R^{12}$ is optionally taken together with one of $R^{13}$, $R^{14}$, $R^{15}$, $R^{16}$, and $R^{17}$ to form a monocyclic moiety;

each of $R^1$-$R^{17}$ is optionally and independently substituted with one or more substituents independently selected from the group consisting of halogen, $C_{1-4}$ alkyl, $C_{1-4}$ haloalkyl, —CN, —NO$_2$, —O$R^a$, —C(O)$R^b$, —C(O)O$R^a$, —OC(O)$R^b$, —N($R^a$)$_2$, —N$R^a$C(O)$R^b$, —C(O)N($R^a$)$_2$, —S(O)$R^b$, —S(O)$_2R^b$, —S(O)$_2$O$R^a$, —S(O)$_2$N($R^a$)$_2$, and —N$R^a$S(O)$_2R^b$;

each $R^a$ is independently selected from the group consisting of H, $C_{1-4}$ alkyl, a solubilizing moiety, and a targeting moiety; and each $R^b$ is independently selected from the group consisting of $C_{1-4}$ alkyl, a solubilizing moiety, and a targeting moiety.

8. The compound of embodiment 7, or a pharmaceutically acceptable salt thereof, wherein $R^2$ and $R^3$ are taken together to form a fused tricyclic moiety.

9. The compound of embodiment 8, or a pharmaceutically acceptable salt thereof, wherein the fused tricyclic moiety is a tricycloundecenediyl moiety.

10. The compound of embodiment 7, or a pharmaceutically acceptable salt thereof, wherein $R^2$ and $R^3$ are independently selected from the group consisting of $C_{3-8}$ cycloalkyl, $C_{6-10}$ aryl, 3- to 8-membered heterocyclyl, and 5- to 12-membered heteroaryl.

11. The compound of any one of embodiments 7-10, or a pharmaceutically acceptable salt thereof, having a structure according to Formula Ia:

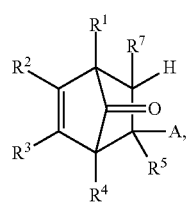

(Ia)

wherein A is selected from the group consisting of —Se$R^{13}$ and —S$R^{14}$

12. The compound of embodiment 11, or a pharmaceutically acceptable salt thereof, wherein A is in the cis configuration with respect to proton H.

13. The compound of embodiment 11, or a pharmaceutically acceptable salt thereof, wherein A is in the trans configuration with respect to proton H.

14. The compound of any one of embodiments 7-13, or a pharmaceutically acceptable salt thereof, wherein $R^{13}$ or $R^{14}$ is selected from the group consisting of $C_{1-8}$ alkyl and $C_{6-10}$ aryl.

15. The compound of any one of embodiments 7-13, or a pharmaceutically acceptable salt thereof, wherein $R^2$ and $R^3$ are phenyl, each of which is optionally and independently substituted.

16. The compound of any one of embodiments 7-15, or a pharmaceutically acceptable salt thereof, wherein $R^1$ and $R^4$ are independently selected from the group consisting of $C_{1-8}$ alkyl, $C_{6-10}$ aryl, and —C(O)$OR^8$.

17. The compound of any one of embodiments 7-16, or a pharmaceutically acceptable salt thereof, wherein $R^5$ is selected from the group consisting of H, —C(O)$OR^9$, and —C(O)N($R^{11}$)$_2$.

18. The compound of any one of embodiments 7-17, or a pharmaceutically acceptable salt thereof, wherein $R^9$ is H or methyl.

19. The compound of any one of embodiments 7-17, or a pharmaceutically acceptable salt thereof, wherein each $R^{11}$ is independently selected from the group consisting of H and a targeting moiety.

20. The compound of embodiment 19, or a pharmaceutically acceptable salt thereof, wherein the targeting moiety is a mitochondrial targeting moiety.

21. The compound of embodiment 20, or a pharmaceutically acceptable salt thereof, wherein the mitochondrial targeting moiety comprises a phosphonium group.

22. The compound of any one of embodiments 7-21, or a pharmaceutically acceptable salt thereof, wherein $R^7$ is H.

23. The compound of any one of embodiments 7-21, wherein $R^7$ is —C(O)$R^{10}$, and $R^{10}$ is H.

24. The compound of embodiment 7, which is selected from the group consisting of:

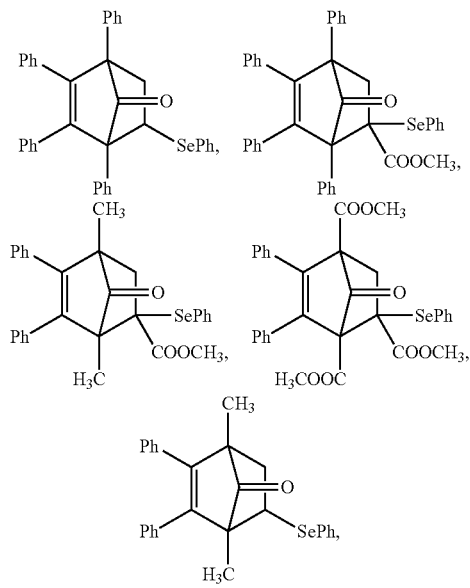

-continued

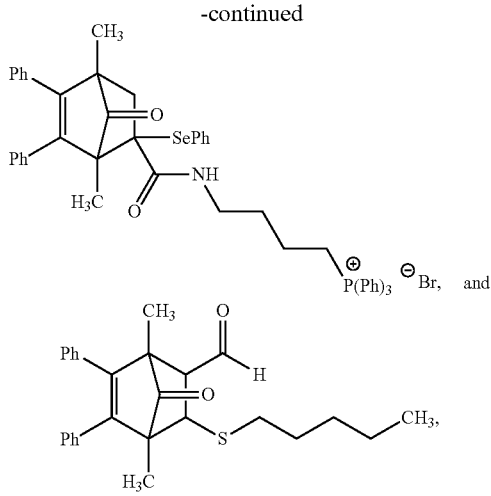

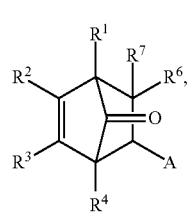

wherein Ph represents phenyl,
and pharmaceutically acceptable salts thereof.

25. The compound of any one of embodiments 7-11, or a pharmaceutically acceptable salt thereof, having a structure according to Formula Ib:

(Ib)

wherein A is selected from the group consisting of —$SR^{14}$, —$S(O)R^{14}$, —$S(O)_2R^{14}$, and —$OR^{15}$.

26. The compound of embodiment 25, or a pharmaceutically acceptable salt thereof, wherein $R^7$ is H which is in the trans configuration with respect to A.

27. The compound of embodiment 25 or embodiment 26, or a pharmaceutically acceptable salt thereof, wherein A is selected from the group consisting of —$S(O)R^{14}$, —$S(O)_2R^{14}$, and —$OR^5$.

28. The compound of any one of embodiments 7-10 and 25-27, or a pharmaceutically acceptable salt thereof, wherein $R^{14}$ or $R^{15}$ is selected from the group consisting of optionally substituted phenyl and optionally substituted 5- to 12-membered heteroaryl.

29. The compound of any one of embodiments 7-10 and 25-28, or a pharmaceutically acceptable salt thereof, wherein $R^6$ is —$C(O)R^{10}$ and $R^{10}$ is H.

30. The compound of any one of embodiments 7-10 and 25-29, wherein $R^6$ is —$C(O)R^{10}$, and $R^{10}$, is taken together with $R^{14}$ or $R^{15}$ to form a monocyclic moiety.

31. The compound of any one of embodiments 7-10 and 25-29, wherein $R^6$ is —$S(O)_2R^{12}$ and $R^{12}$ is $C_{6-10}$ aryl.

32. The compound of any one of embodiments 7 and 25-31, or a pharmaceutically acceptable salt thereof, wherein $R^2$ and $R^3$ are phenyl, each of which is optionally and independently substituted.

33. The compound of any one of embodiments 7-10 and 25-32, or a pharmaceutically acceptable salt thereof, wherein $R^1$ and $R^4$ are independently selected from the group consisting of $C_{1-8}$ alkyl, $C_{6-10}$ aryl, and —$C(O)OR^8$.

34. The compound of embodiment 7, which is selected from the group consisting of:

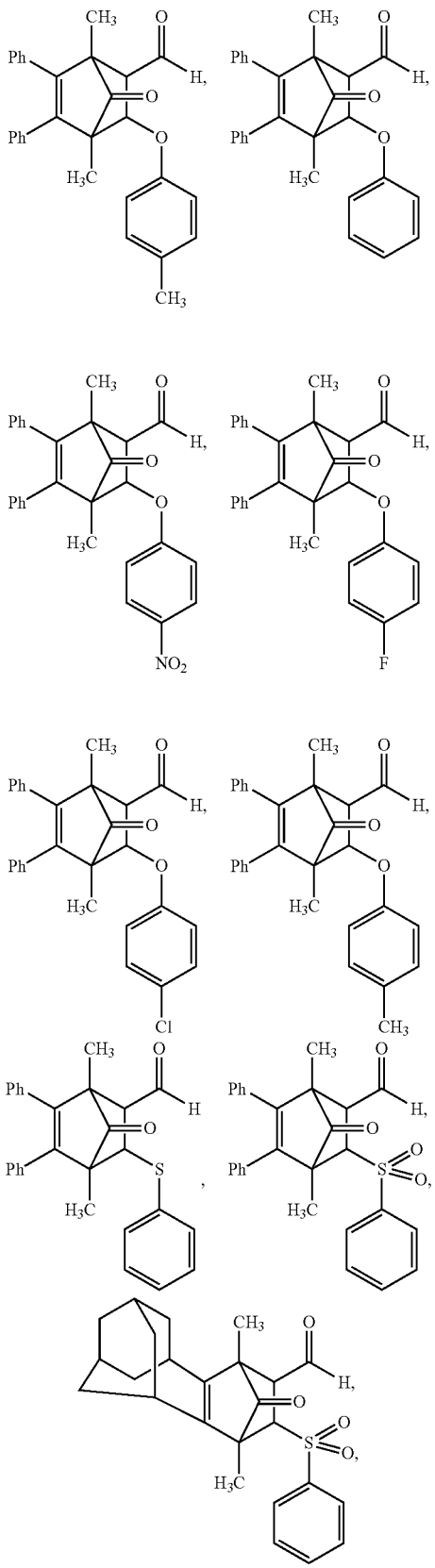

-continued

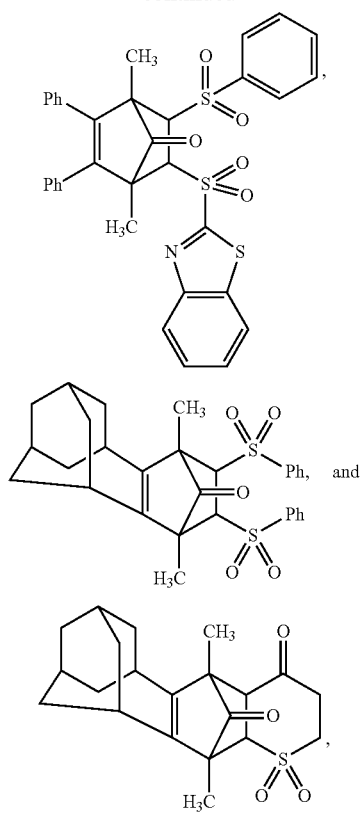

wherein Ph represents phenyl.

35. The compound of any one of embodiments 7-10, or a pharmaceutically acceptable salt thereof, having a structure according to Formula Ic:

(Ic)

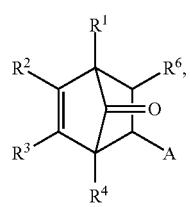

wherein

R$^6$ is selected from the group consisting of —CH(OR$^{10}$)$_2$ and —CH(SR$^{10}$)$_2$; and A is selected from the group consisting of —SR$^{14}$, —S(O)R$^{14}$, —S(O)$_2$R$^{14}$, and —OR.

36. The compound of embodiment 35, or a pharmaceutically acceptable salt thereof, wherein A is selected from the group consisting of —S(O)R$^{14}$, —S(O)$_2$R$^{14}$, and —OR$^{15}$.

37. The compound of embodiment 35 or embodiment 36, or a pharmaceutically acceptable salt thereof, wherein R$^{10}$ is C$_{1-8}$ alkyl which is optionally substituted with —C(O)OR$^a$.

38. The compound of any one of embodiments 35-37, which is:

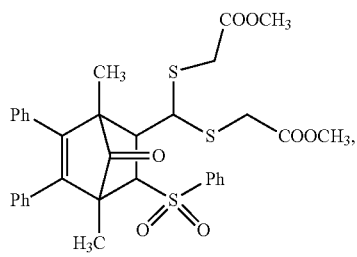

or a pharmaceutically acceptable salt thereof.

39. The compound of embodiment 35 or embodiment 36, or a pharmaceutically acceptable salt thereof, wherein R$^{10}$ is C$_{2-8}$ acyl.

40. The compound of any one of embodiments 35, 36, and 39, which is selected from the group consisting of:

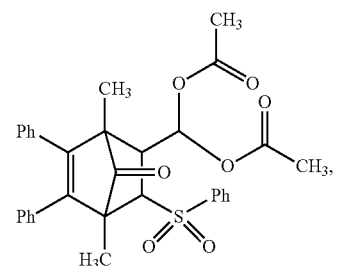

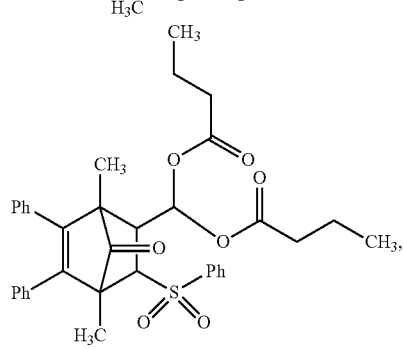

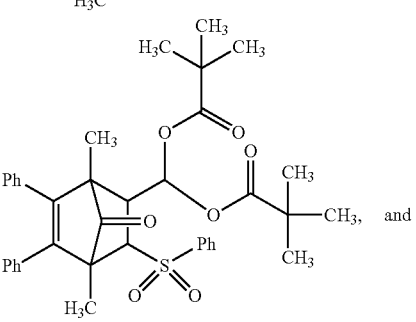

and

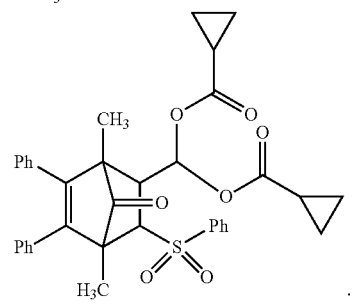

41. A pharmaceutical composition comprising a compound according to any one of embodiments 1-40 and a pharmaceutically acceptable excipient.

42. A method for delivering carbon monoxide to a subject in need thereof, the method comprising administering to the subject a compound according to any one of embodiments 1-40 or a pharmaceutical formulation according to embodiment 41.

43. A method for treating a disease or condition, the method comprising administering to a subject in need thereof an effective amount of a compound according to any one of embodiments 1-40 or an effective amount of a pharmaceutical formulation according to embodiment 41.

44. The method of embodiment 43, wherein the disease or condition is selected from the group consisting of inflammation, cancer, ulcerative colitis, organ transplantation, bacterial infection, and thrombosis.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A compound comprising a cyclopentenone moiety and a reactive moiety, wherein the compound has a structure according to Formula I:

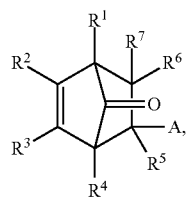

(I)

or a pharmaceutically acceptable salt thereof, wherein:
A is the reactive moiety, which is selected from the group consisting of $-S(O)_2R^{14}$, $-S(O)R^{14}$, $-SR^{14}$, $-SeR^{13}$, $-OS(O)_2R^{14}$, $-OR^{15}$, $-OP(O)(OR^{15})_2$, $-OC(O)R^{16}$, $-OC(O)N(R^{17})_2$, and $-N^+(R^{17})_3$;
$R^1$ and $R^4$ are independently selected from the group consisting of $C_{1-8}$ alkyl, $C_{3-8}$ cycloalkyl, $C_{6-10}$ aryl, 3- to 8-membered heterocyclyl, 5- to 12-membered heteroaryl, $-C(O)OR^8$, and hydrogen;
$R^2$ and $R^3$ are taken together to form a fused tricyclic moiety or a fused bicyclic moiety, or
$R^2$ and $R^3$ are independently selected from the group consisting of hydrogen, $C_{1-8}$ alkyl, $C_{3-8}$ cycloalkyl, $C_{6-10}$ aryl, 3- to 8-membered heterocyclyl, 5- to 12-membered heteroaryl, and $-C(O)OR^8$;
$R^5$ is selected from the group consisting of hydrogen, $C_{1-8}$ alkyl, $-CN$, $-C(O)OR^9$, $-C(O)R^{10}$, $-C(O)N(R^{11})_2$, and a targeting moiety;
$R^6$ is selected from the group consisting of $-S(O)_2R^{12}$, $-S(O)R^{12}$, $C_{1-8}$ alkyl, $-CN$, $-C(O)OR^9$, $-C(O)R^{10}$, $-CH(OR^{10})_2$, $-CH(SR^{10})_2$, $-C(O)N(R^{11})_2$, and hydrogen;

$R^7$ is selected from the group consisting of hydrogen, $C_{1-8}$ alkyl, $-CN$, $-C(O)OR^9$, $-C(O)R^{10}$, $-CH(OR^{10})_2$, $-CH(SR^{10})_2$, $-C(O)N(R^{11})_2$, $-S(O)R^{12}$, and $-S(O)_2R^{12}$;
$R^8$ is selected from the group consisting of hydrogen and $C_{1-6}$ alkyl;
each $R^9$, $R^{10}$, $R^{11}$, and $R^{12}$ is independently selected from the group consisting of hydrogen, $C_{1-8}$ alkyl, $C_{2-8}$ acyl, $C_{6-10}$ aryl, and a targeting moiety;
each $R^{13}$, $R^{15}$, $R^{16}$, and $R^{17}$ is independently selected from the group consisting of $C_{1-8}$ alkyl, $C_{3-8}$ cycloalkyl, $C_{6-10}$ aryl, and 5- to 12-membered heteroaryl;
$R^{14}$ is independently selected from the group consisting of $C_{6-10}$ aryl, $C_{1-8}$ alkyl, $C_{3-8}$ cycloalkyl, and 5- to 12-membered heteroaryl;
in $R^6$ or $R^7$, one of $R^9$, $R^{10}$, $R^{11}$, and $R^{12}$ is optionally taken together with one of $R^{13}$, $R^{14}$, $R^{15}$, $R^{16}$, and $R^{17}$ to form a monocyclic moiety;
each of $R^1$-$R^{17}$ is optionally and independently substituted with one or more substituents independently selected from the group consisting of halogen, $C_{1-4}$ alkyl, $C_{1-4}$ haloalkyl, $-CN$, $-NO_2$, $-OR^a$, $-C(O)R^b$, $-C(O)OR^a$, $-OC(O)R^b$, $-N(R^a)_2$, $-NR^aC(O)R^b$, $-C(O)N(R^a)_2$, $-S(O)R^b$, $-S(O)_2R^b$, $-S(O)_2OR^a$, $-S(O)_2N(R^a)_2$, and $-NR^aS(O)_2R^b$;
each $R^a$ is independently selected from the group consisting of hydrogen, $C_{1-4}$ alkyl, a solubilizing moiety, and a targeting moiety; and
each $R^b$ is independently selected from the group consisting of $C_{1-4}$ alkyl, a solubilizing moiety, and a targeting moiety,
wherein exposure of the compound to physiological conditions results in elimination of the reactive moiety and release of carbon monoxide.

2. The compound of claim 1, wherein the reactive moiety is a leaving group or a leaving group precursor.

3. The compound of claim 2, wherein a change in pH upon exposure to physiological conditions or enzyme activity upon exposure to physiological conditions results in elimination of the leaving group.

4. The compound of claim 2, wherein exposure of the leaving group precursor to reactive oxygen species upon exposure to physiological conditions results in formation of a leaving group and elimination of the leaving group.

5. The compound of claim 1, or a pharmaceutically acceptable salt thereof, wherein $R^2$ and $R^3$ are taken together to form a fused tricyclic moiety, or $R^2$ and $R^3$ are independently selected from the group consisting of $C_{3-8}$ cycloalkyl, $C_{6-10}$ aryl, 3- to 8-membered heterocyclyl, and 5- to 12-membered heteroaryl.

6. The compound of claim 1, or a pharmaceutically acceptable salt thereof, having a structure according to Formula Ib:

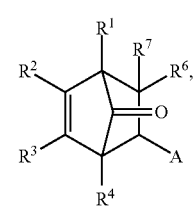

(Ib)

wherein A is a leaving group selected from the group consisting of —S(O)$_2$R$^{14}$, —S(O)R$^{14}$, —SR$^{14}$, and —OR$^{15}$;

R$^1$ and R$^4$ are independently selected from the group consisting of C$_{1-8}$ alkyl, C$_{6-10}$ aryl, and —C(O)OR$^8$;

R$^2$ and R$^3$ are taken together to form a fused tricyclic moiety, or R$^2$ and R$^3$ are phenyl, each of which is optionally and independently substituted;

R$^6$ is selected from the group consisting of —S(O)$_2$R$^{12}$ and —C(O)R$^{10}$;

R$^7$ is H;

R$^{10}$ is hydrogen, or R$^{10}$ is taken together with R$^{14}$ or R$^{15}$ to form a monocyclic moiety;

R$^{12}$ is C$_{6-10}$ aryl; and

R$^{14}$ or R$^{15}$ is selected from the group consisting of C$_{1-8}$ alkyl, unsubstituted phenyl, substituted phenyl, unsubstituted 5- to 12-membered heteroaryl, and substituted 5- to 12-membered heteroaryl.

7. The compound of claim 6, or a pharmaceutically acceptable salt thereof, wherein R$^7$ is in the trans configuration with respect to A.

8. The compound of claim 6, which is selected from the group consisting of:

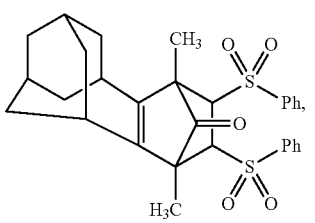

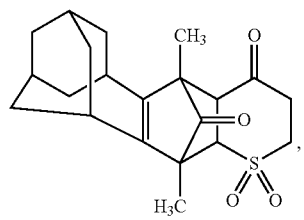

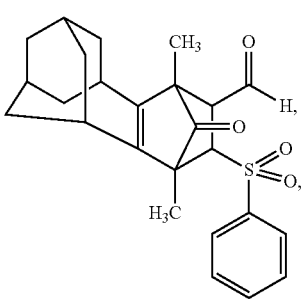

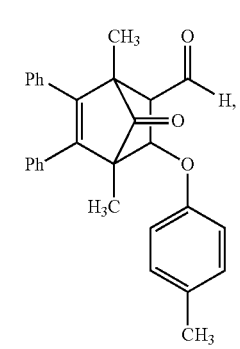

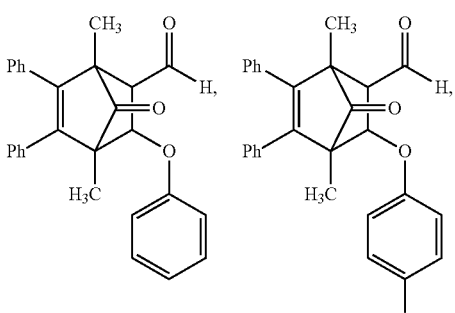

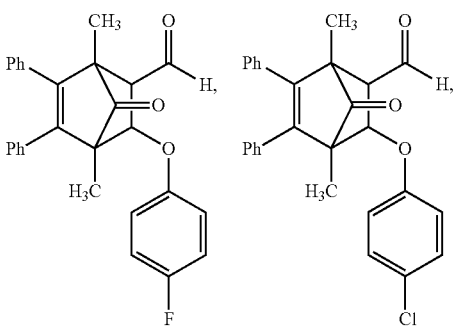

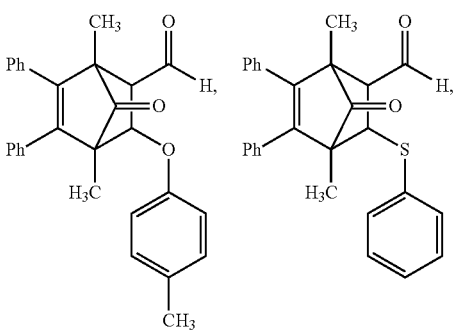

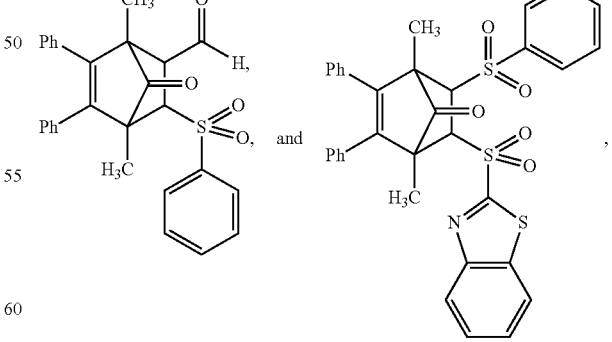

wherein Ph represents phenyl.

9. The compound of claim 1, or a pharmaceutically acceptable salt thereof, having a structure according to Formula Ia:

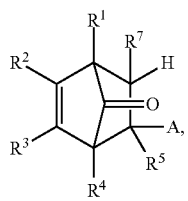

(Ia)

wherein A is selected from the group consisting of —SeR$^{13}$ and —SR$^{14}$;

R$^1$ and R$^4$ are independently selected from the group consisting of C$_{1-8}$ alkyl, C$_{6-10}$ aryl, and —C(O)OR$^8$;

R$^2$ and R$^3$ are phenyl, each of which is optionally and independently substituted;

R$^5$ is selected from the group consisting of hydrogen, —C(O)OR$^8$, and —C(O)N(R$^{11}$)$_2$;

R$^7$ selected from the group consisting of hydrogen and —C(O)R$^{10}$; and

R$^{10}$ is hydrogen.

10. The compound of claim 9, or a pharmaceutically acceptable salt thereof, wherein R$^{13}$ or R$^{14}$ is selected from the group consisting of C$_{1-8}$ alkyl and C$_{6-10}$ aryl.

11. The compound of claim 9, or a pharmaceutically acceptable salt thereof, wherein R$^9$ is hydrogen or methyl.

12. The compound of claim 9, or a pharmaceutically acceptable salt thereof, wherein each R$^{11}$ is independently selected from the group consisting of hydrogen and a targeting moiety.

13. The compound of claim 9, which is selected from the group consisting of:

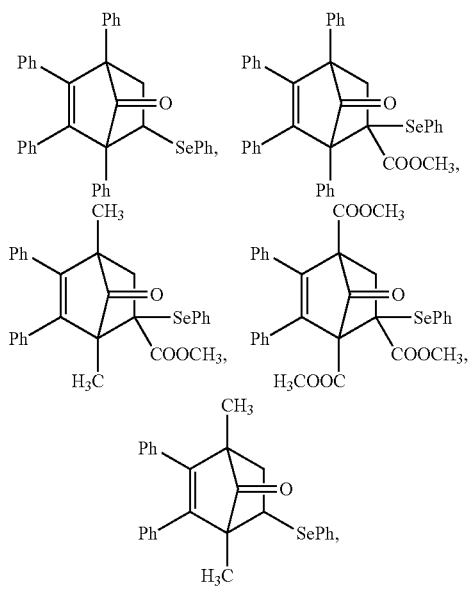

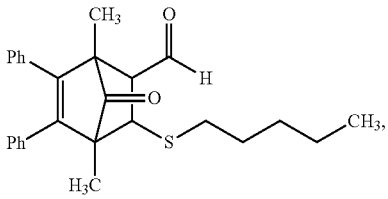

wherein Ph represents phenyl, and pharmaceutically acceptable salts thereof.

14. The compound of claim 1, or a pharmaceutically acceptable salt thereof, having a structure according to Formula Ic:

(Ic)

wherein

R$^6$ is selected from the group consisting of —CH(OR$^{10}$)$_2$ and —CH(SR$^{10}$)$_2$; and A is selected from the group consisting of —SR$^{14}$, —S(O)R$^{14}$, —S(O)$_2$R$^{14}$, and —OR$^{15}$.

15. The compound of claim 14, which is:

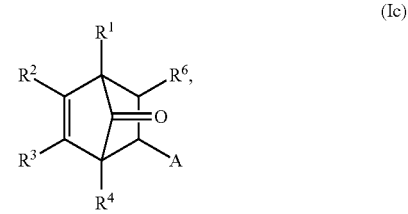

16. The compound of claim 14, which is selected from the group consisting of:

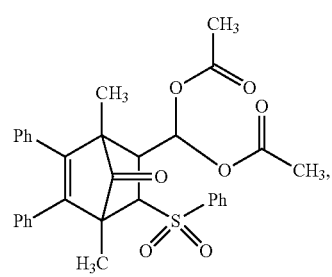

-continued

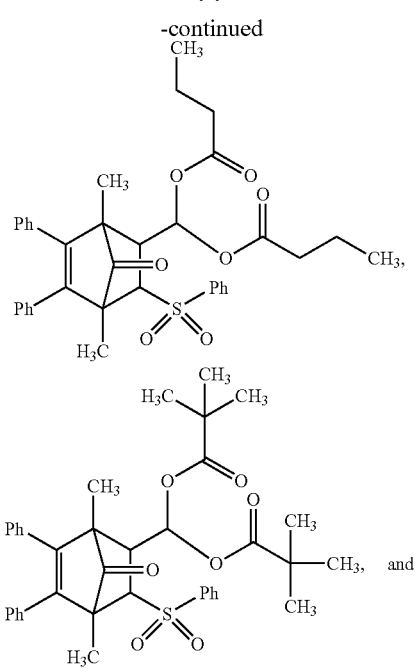

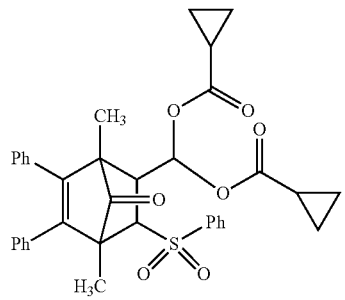

17. A pharmaceutical composition comprising a compound according to claim 1 and a pharmaceutically acceptable excipient.

18. A method for treating a disease or condition, the method comprising administering to a subject in need thereof an effective amount of a compound according to claim 1, wherein the disease or condition is selected from the group consisting of inflammation, ulcerative colitis, organ transplantation, bacterial infection, and thrombosis.

* * * * *

UNITED STATES PATENT AND TRADEMARK OFFICE
CERTIFICATE OF CORRECTION

PATENT NO. : 11,685,711 B2  
APPLICATION NO. : 16/637737  
DATED : June 27, 2023  
INVENTOR(S) : Ladie Kimberly c. De La Cruz et al.

Page 1 of 1

It is certified that error appears in the above-identified patent and that said Letters Patent is hereby corrected as shown below:

In the Claims

In Column 74, Lines 32-45, in Claim 8, delete " 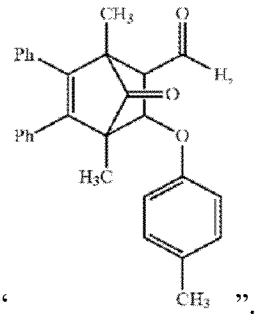 ".

In Column 75, Line 18, in Claim 9, delete "—C(O)OR$^8$," and insert -- —C(O)OR$^9$, --.

Signed and Sealed this  
Thirteenth Day of February, 2024

Katherine Kelly Vidal  
*Director of the United States Patent and Trademark Office*